(12) United States Patent
Herrera et al.

(10) Patent No.: US 7,919,093 B2
(45) Date of Patent: Apr. 5, 2011

(54) ROLES FOR DUAL ENDOTHELIN-1/ANGIOTENSIN II RECEPTOR (DEAR) IN HYPERTENSION AND ANGIOGENESIS

(75) Inventors: Victoria L. M. Herrera, Westwood, MA (US); Nelson Ruiz-Opazo, Westwood, MA (US)

(73) Assignee: Trustees of Boston University, Boston, MA (US)

( * ) Notice: Subject to any disclaimer, the term of this patent is extended or adjusted under 35 U.S.C. 154(b) by 581 days.

(21) Appl. No.: 11/667,713

(22) PCT Filed: Nov. 15, 2005

(86) PCT No.: PCT/US2005/041594
§ 371 (c)(1),
(2), (4) Date: May 14, 2007

(87) PCT Pub. No.: WO2006/055665
PCT Pub. Date: May 26, 2006

(65) Prior Publication Data
US 2009/0028852 A1    Jan. 29, 2009

Related U.S. Application Data

(60) Provisional application No. 60/628,447, filed on Nov. 16, 2004, provisional application No. 60/694,268, filed on Jun. 27, 2005.

(51) Int. Cl.
*C07K 16/28* (2006.01)
(52) U.S. Cl. .................. 424/143.1; 435/334; 530/388.22
(58) Field of Classification Search .................. None
See application file for complete search history.

(56) References Cited

U.S. PATENT DOCUMENTS

| | | | | |
|---|---|---|---|---|
| 5,440,021 | A | * | 8/1995 | Chuntharapai et al. ... 530/388.22 |
| 6,641,811 | B1 | * | 11/2003 | Suthanthiran et al. ..... 424/146.1 |
| 2001/0021772 | A1 | | 9/2001 | Uhlmann |

OTHER PUBLICATIONS

Ruiz-Opazo et al. 2002 Molecular Medicine vol. 8 p. 24.*
Ruiz-Opazo et al. (Molecular Medicine 1998 vol. 4 p. 96).*
Fujita, M. et al., "Blockade of angiotensin AT1a receptor signaling reduces tumor growth, angiogensis, and metastasis," Biochemical and Biophysical Research Communications 294:441-447, 2002.
Ruiz-Opazo, N et al., "Molecular Characterization of a Dual Endothelin-1/Angiotensin II Receptor." Molecular Medicine 4:96-108, 1998.
Kaneko, Y et al., "Sex-specific effects of dual ET-1/ANG II receptor (Dear) variants in Dahl salt-sensitive/resistant hypertension rat model." Physiol Genomics 20:157-164, 2005.
Glorioso, N et al., "Association of ATP1A1 and Dear Single-Nucleotide Polymorphism Haplotypes With Essential Hypertension Sex-Specific and Haplotype-Specific Effects." Circ Res. 100:1522-1529, 2007.
Ruiz-Opazo, N. et al., V.L.M. Molecular characterization of a dual endothelin-1/angiotensin II receptor. Molecular Medicine 4, 96-108 (1998).
Kaneko, Y. et al., N. Sex-specific effects of dual ET-1/AngII receptor (Dear) variants in Dahl salt-sensitive/resistant hypertension rat model. Physiol Genomics 20, 157-167 (2005).
Salani, D. et al. Role of endothelin-1 in neovascularization of ovarian carcinoma. Am. J. Pathol. 157, 1537-1547 (2000).
Sullivan, D.C. & Bicknell, R. New molecular pathways in angiogenesis. British Journal of Cancer 89, 228-231 (2003).
Kurihara, Y. et al. Elevated blood pressure and craniofacial abnormalities in mice deficient in endothelin-1. Nature 368, 703-710 (1994).
Clouthier, D.E. et al. Cranial and cardiac neural crest defects in endothelin-A receptor-deficient mice. Development 125,813-824 (1998).
Tanimoto, K. et al. Angiotensinogen-deficient mice with hypotension. J Biol Chem 269, 31334-31337 (1994).
Ito, M. et al. Regulation of blood pressure by the type 1A angiotensin II receptor gene. Pro Natl Acad Sci 92, 3521-3525 (1995).
Chen, X. et al. Targeting deletion of angiotensin type 1B receptor gene in the mouse. Am J Physiol 272, F299-F304 (1997).
Hein, L. et al., Behavioural and cardiovascular effects of disrupting the angiotensin II type 2 receptor in mice. Nature 377, 744-777 (1995).
Carmeliet, P. et al. Abnormal blood vessel development and lethality in embryos lacking a single VEGF allele. Nature 380, 435-439 (1996).
Ferrara, N. et al. Heterozygous embryonic lethality induced by targeted inactivation of the VEGF gene. Nature 380, 439-442 (1996).
Ikeda, T. et al. Pathophysiological roles of endothelin-1 in Dahl salt-sensitive hypertension. Hypertension 34, 514-519 (1999).
Fujita, M. et al. Angiotensin type 1a receptor signaling-dependent induction of vascular endothelial growth factor in stroma is relevant to tumor-associated angiogenesis and tumor growth. Carcinogenesis 26, 271-279 (2005).
Dickson, M.C. et al. Defective haematopoiesis and vasculogenesis in transforming growth factor-b1 knockout mice. Development 121, 1845-1854 (1995).
Herrera, V.L.M. et al. Spontaneous combined hyperlipidemia, coronary heart disease and decreased survival in Dahl salt-sensitive hypertensive rats transgenic for human cholesteryl ester transfer protein. Nature Med 12, 1383-1389 (1999).
Agapitov, A.V. and Haynes, W.G., Role of endothelin in cardiovascular disease. J. Renin Angiotensin Aldosterone Syst. 3: 1-15, 2002.
Elijovich, F. and Laffer, C. L., Participation of renal and circulating endothelin in salt-sensitive essential hypertension. J. Hum. Hypertens. 16: 459-467, 2002.
Garrett, M. R. Genome scan and congenic strains for blood pressure QTL using Dahl Salt sensitive rats. Genome Res. 8:711-723, 1998.

(Continued)

*Primary Examiner* — John D Ulm
(74) *Attorney, Agent, or Firm* — Nixon Peabody LLP

(57) ABSTRACT

The present application is directed to the identification of mutations and/or polymorphisms in the Dual Endothelin-1/Angiotensin II Receptor (Dear) that indicate susceptibility to, or show current affliction with, hypertension. Additionally, the present invention discloses methods for the modulation of angiogenesis via the regulation of Dear.

5 Claims, 29 Drawing Sheets

OTHER PUBLICATIONS

Hausdorff, W. P. et al., A mutation of b2-adrenergic receptor impairs agonist activation of adenylyl cyclase without affecting high affinity agonist binding. Distinct molecular determinants of the receptor are involved in physical coupling to and functional activation of GS. J. Biol. Chem. 265: 1388-1393, 1990.

Herrera, V. L. M. and Ruiz-Opazo, N., Genetics of hypertension: A multidisciplinary challenge. Trends in Cardiovascular Medicine 1: 185-189, 1991

Herrera, V. L. M., et al., The α1 Na,K-ATPase gene is a susceptibility hypertension gene in the Dahl salt-sensitive rat. J. Clin. Invest. 102: 1102-1111, 1998.

Herrera, V. L. M., et al., α1 Na,K-ATPase and Na,K,2Cl-cotransporter/D3Mit3 loci interact to increase susceptibility to salt-sensitive hypertension in Dahl SHSD rats. Molecular Medicine 7: 125-134, 2001.

Iwanaga Y, et al., Differential effects of angiotensin II versus endothelin-1 inhibitions in hypertrophic left ventricular myocardium during transition to heart failure. Circulation 104: 606-612, 2001.

Jeffs B, et al., Applicability of a "speed" congenic strategy to dissect blood pressure quantitative trait loci on rat chromosome 2. Hypertension 35: 179-187, 2000.

Kaneko Y, et al., Corroboration of Dahl S Q276L alpha1-Na,K-ATPase protein sequence: impact on affinities for ligands and on E1 conformation. J Hypertension 23: 745-752, 2005.

Kent RS, et al., A quantitative analysis of beta-adrenergic receptor interactions: resolution of high and low affinity states of the receptor by computer modeling of ligand binding data. Mol. Pharmacol. 17: 14-23, 1980.

Lavallée M et al. Crosstalk between endothelin and nitric oxide in the control of vascular tone. Heart Fail. Rev. 6: 265-276, 2001.

Mukoyama M, et al., Expression cloning of type 2 angiotensin II receptor reveals a unique class of seven transmembrane receptors. J. Biol. Chem. 268: 24539-24542, 1993.

Murphy TJ, et al., Isolation of a cDNA encoding the vascular type-1 angiotensin II receptor. Nature 351: 233-236, 1991.

Nuedling S, et al., 17 Beta-estradiol regulates the expression of endothelin receptor type B in the heart. Br J Pharmacol. 140: 195-201, 2003.

Phalipou S, et al., Docking of linear peptide antagonists into the human V1a vasopressin receptor. J. Biol. Chem. 274: 23316-23327, 1999.

Pravenec M, et al., Mapping of quantitative trait loci for blood pressure and cardiac mass in the rat by genome scanning of recombinant inbred strains. J. Clin. Invest. 96: 1973-1978, 1995.

Rapp JP. Genetic analysis of inherited hypertension in the rat. Physiological Reviews 80: 135-172, 2000.

Romero JC and Reckelhoff JF. Role of angiotensin and oxidative stress in essential hypertension. Hypertension 34: 943-949, 1999.

Ruiz-Opazo N., et al., Identification of a novel dual AngiotensinII/Vasopressin receptor on the basis of molecular recognition theory. Nature Medicine 1: 1074-1081, 1995.

Ruiz-Opazo N., et al., The dual AngII/AVP receptor gene N119S/C163R variant exhibits sodium-induced dysfunction and cosegregates with salt-sensitive hypertension in the Dahl salt-sensitive hypertensive rat model. Molecular Medicine 8: 24-32, 2002.

Song Y, et al., Non-association of the thiazide-sensitive Na,Cl-cotransporter gene with polygenic hypertension in both rats and humans. J. Hypertension 19: 1547-1551, 2001.

Tsukamoto T, et al., Isolation and characterization of the yeast mRNA capping enzyme beta subunit gene encoding RNA 5'-triphosphatase, which is essential for cell viability. Biochem. Biophy. Res. Commun. 239: 116-122, 1997.

Richardson JC, et al., Ultrastructural and behavioural changes precede amyloid deposition in a transgenic model of Alzheimer's disease. Neuroscience 122: 213-228 (2003).

Kaneko Y, et al., Sex-specific effects of dual ET-1/AngII receptor (Dear) variants in Dahl salt-sensitive/resistant hypertension rat model. Physiol Genomics Nov. 23; [Epub ahead of print], (2004).

Long BJ, et al., Therapeutic strategies using the aromatase inhibitor letrozole and tamoxifen in a breast cancer model. J Natl Cancer Inst 96: 456-465 (2004).

Storkebaum E, et al. 2005. Treatment of motoneuron degeneration by intracerebroventricular delivery of VEGF in a rat model of ALS. Nature Neuroscience 8:85-92. (E-publication Nov. 28, 2004).

Woodman, S.E. et al. Caveolin-1 knockout mice show an impaired angiogenic response to exogenous stimuli. Am J Pathol 162:2059-2068 (2003).

Linder et al. "Pharmacogenetics: a laboratory tool for optimizing therapeutic efficiency," Clinical Chemistry, 43 (2):254-266, 1997.

Larivière, R. & Lebel, M. Endothelin-1 in chronic renal failure and hypertension. Can J Physiol Pharmacol. 81, 607-621 (2003).

Bagnato, A. & Spinella, F. Emerging role of endothelin-1 in tumor angiogenesis. Trends in Endocrinology and Metabolism 14, 44-50 (2002).

Grant, K. et al., Endothelin-1: a multifunctional molecule in cancer. British Journal of Cancer 88, 163-166 (2003).

Watanabe, T. et al., Angiotensin II and the Endothelium: Diverse signals and effects. Hypertension 45, 163-169 (2005).

Escobar, E. et al., Angiotensin II, cell proliferation and angiogenesis regulator: biologic and therapeutic implications in cancer. Curr Vasc Pharmacol 2, 385-399 (2004).

Hosoda, K. et al. Targeted and natural (piebald-lethal) mutations of endothelin-B receptor gene produce megacolon associated with spotted coat color in mice. Cell 79, 1267-1276 (1994).

Niimura, F. et al. Gene targeting in mice reveals a requirement for angiotensin in the development and maintenance of kidney morphology and growth factor regulation. J Clin Invest. 96, 2947-2954 (1995).

Raab, S. et al. Impaired brain angiogenesis and neuronal apoptosis induced by conditional homozygous inactivation of vascular endothelial growth factor. Thromb Haemost 91, 595-605 (2004).

Touyz, R.M. & Schiffrin, E.L. Role of endothelin in human hypertension. Can J Physiol Pharmacol. 81, 533-541 (2003).

Griswold, D.E. et al. Targeted disruption of the endothelin-B-receptor gene attenuates inflammatory nociception and cutaneous inflammation in mice. J Cardiovasc Pharmacol 36, S78-S81 (2000).

D'Orléans-Juste, P. et al., Synthesis and degradation of endothelin-1. Can J Physiol Pharmacol. 81, 503-510 (2003).

Antoniucci D. et al., Gender-related differences in proliferative responses of vascular smooth muscle cells to endothelin-1. Endothelium 8: 137-145, 2001.

Blalock JE. Genetic origins of protein shape and interaction rules. Nature Medicine 1: 876-878, 1995.

Clark JS et al., Quantitative trait loci in genetically hypertensive rats, possible sex specificity. Hypertension 28: 898-906, 1996.

Doi T. et al., Characterization of human endothelin B receptor and mutant receptors expressed in insect cells. Eur. J. Biochem. 248: 139-148, 1997.

Hallberg P. et al., Gender-specific association between preproendothelin-1 genotype and reduction of systolic blood pressure during antihypertensive treatment-results from the Swedish Irbesartan Left Ventricular Hypertrophy Investigation versus Atenolol (SILVHIA). Clin Cardiol. 27: 287-290, 2004.

Jørgensen PL. Purification of (Na+ plus K+ )-ATPase: active site determinations and criteria of purity. Ann. N.Y. Acad. Sci. 242: 36-52, 1974.

Manly KF et al., Map Manager QTX, cross-platform software for genetic mapping. Mammalian Genome 12: 930-932, 2001.

Rapp JP and Dene H. Development and characteristics of inbred strains of Dahl salt-sensitive and salt-resistant rats. Hypertension 7: 340-349, 1985.

Rapp JP and Dene H. Failure of alleles at the Na+,K+-ATPase α1 locus to cosegregate with blood pressure in Dahl rats. J Hypertension 8: 457-462, 1990.

Rodbard D. Mathematics of hormone-receptor interaction. Adv. Exp. Medicine 36: 289-326, 1972.

Samani NJ et al., Analysis of quantitative trait loci for blood pressure on rat chromosomes 2 and 13. Age-related differences in effect. Hypertension 28: 1118-1122, 1996.

Tatchum-Talom R. et al., Gender differences in hemodynamic responses to endothelin-1. J Cardiovasc Pharrnacol. 36: S102-S104, 2000.

Wong C. et al., The angiotensin II receptor (Agtr1a): functional regulatory polymorphisms in a locus genetically linked to blood pressure variation in the mouse. Physiol Genomics 14: 83-93, 2003.

Wright JW and Harding JW. Regulatory role of brain angiotensins in the control of physiological and behavioral responses. Brain Research Reviews 17: 227-262, 1992.

Zicha J. et al., Altered Na+-K+pump activity and plasma lipids in salt-hypertensive Dahl rats: relationship to Atp1a1 gene. Physiol Genomics 6: 99-104, 2001.

Morris RGM et al., Place navigation impaired in rats with hippocampal lesions. Nature 297: 681-683 (1982).

Galef BG, Jr. Socially induced diet preference can partially reverse a LiCl-induced diet aversion. Anim Learn Behav 13: 415-418 (1985).

Cronkite EP et al., Studies on radiation-induced mammary gland neoplasia in the rat I. The role of the ovary in the neoplastic response of the breast tissue to total- or partial-body X-irradiation. Radiation Research 12: 81-93 (1960).

Rissanen et al. 2004. Gene transfer for therapeutic vascular growth in myocardial and peripheral ischemia. Adv Genet 52:117-164.

Gusella, DNA Polymorphism and human disease, Ann. Rev. Biochem. 55, 831-854 (1986).

Schafer, A. J. and Hawkins, J. R., "DNA variation and the future of human genetics," Nature Biotechnology 16:33-39, 1998.

Lee, T-H. et al., "Vascular Endothelial Growth Factor Mediates Intracrine Survival in Human Breast Carcinoma Cells through Internally Expressed VEGFR1/FLT1," PLoS Medicine 4(6):1101-1116, 2007.

Lee, S. et al., "Autocrine VEGF Signaling Is Required for Vascular Homeostasis," Cell 130:691-703, 2007.

Marshall, A., "Getting the right drug into the right patient," Nature Biotechnology 15:1249-1252, 1997.

Holash, J. et al., "VEGF-Trap: A VEGF blocker with potent antitumor effects," PNAS 99(17):11393-1398, 2002.

Kim, E. S. et al., "Potent VEGF blockade causes regression of coopted vessels in a model of neuroblastoma," PNAS 99(17):11399-11404, 2002.

* cited by examiner

```
                                            Ab
M S T L Y V T A V P K S H S S L P K C Q A M M S R    25
- N A - - - - T - - - G Y - - - S - - N H N E Q D
                                   Ang-11
T L L T G M A M Y L D S S H A G A A S M Q V S W P    50
- A Y R L W L C T H N H W T - * P S G - R L Q * -
                        ET-1
P L L T S L G S K E M K S R W N W G S I T C I M C    75
* * - - - - - - - - - - - - - - - - - - - - I -
  TM-1
F T C V G S Q L S M S S S K A S N F S G P L Q L Y   100
- - - - - - - - - - - - - - - - - - - - - - - - -
                       IRS
Q R G I G H I T N P Y R R P P A P A W P C S S S G   125
- - - - - - - - - S - K - - Q - - - - - - L - - -

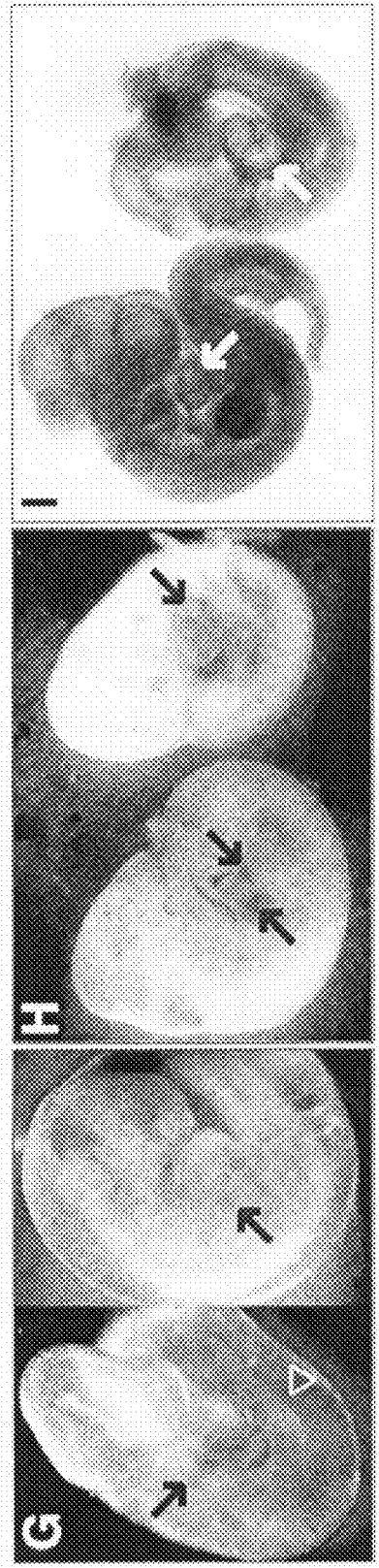

US 7,919,093 B2

ROLES FOR DUAL ENDOTHELIN-1/ANGIOTENSIN II RECEPTOR (DEAR) IN HYPERTENSION AND ANGIOGENESIS

CROSS-REFERENCE TO RELATED APPLICATIONS

This application is a U.S. national stage entry under 37 C.F.R. 371 of the PCT PCT/US2005/041594 filed Nov. 15, 2005, which claims the benefit under 35 U.S.C. §119(e) of U.S. Provisional Patent Application Ser. No. 60/628,447 filed Nov. 16, 2004 and U.S. Provisional Patent Application Ser. No. 60/694,268, filed Jun. 27, 2005, the contents of which are herein incorporated by reference in their entirety.

GOVERNMENT SUPPORT

This invention was made with Government Support under Contract No. HL69937 awarded by the National Institutes of Health. The Government has certain rights in the invention.

FIELD OF THE INVENTION

The present application is directed to the identification of mutations and/or polymorphisms in the Dual Endothelin-1/Angiotensin II Receptor (Dear) that indicate susceptibility to, or show current affliction with, hypertension. Additionally, the present invention discloses methods for the modulation of angiogenesis via the regulation of Dear.

BACKGROUND OF THE INVENTION

The Dual Endothelin-1/Angiotensin II Receptor (Dear) was originally isolated from an adult rat brain cDNA library using an AngII antisense oligonucleotide probe and also, independently, with an ET-1 oligonucleotide, see Molecular Medicine 4: 96-108, 1998. Structural analysis of the receptor revealed putative single predicted transmembrane domain and distinct ET-1 and AngI putative binding domains. Functional analysis has shown that both ET-1 and AngII bind to Dear and induce coupling to a Ca2+ mobilizing transduction system.

ET-1 is a potent vasoconstrictor peptide involved in diverse physiological functions such as blood pressure regulation, mitogenesis and apoptosis (Lariviere, R. et al. *Can J Physiol Pharmacol.* 81, 607-621 (2003), and angiogenesis (Salani, D. et al. *Am. J. Pathol.* 157, 1537-1547 (2000); Sullivan, D. C. & Bicknell, R. *British Journal of Cancer* 89, 228-231 (2003)), and has been implicated in several pathophysiological conditions such as hypertension, cardiac failure (Lariviere, R. et al. *Can J Physiol Pharmacol.* 81, 607-621 (2003); Ikeda, T. et al. *Hypertension* 34, 514-519 (1999); Touyz, R. M. & Schiffrin, E. L. *Can J Physiol Pharmacol.* 81, 533-541 (2003)), and more recently tumor angiogenesis, invasion and metastases (Bagnato, A. & Spinella, F. *Trends in Endocrinology and Metabolism* 14, 44-50 (2002); Grant, K., Loizidou, M. & Taylor, I. *British Journal of Cancer* 88, 163-166 (2003)).

AngII exhibits similar physiological responses to ET-1, such as blood pressure regulation, proliferation, apoptosis and angiogenesis (Watanabe, T. et al. *Hypertension* 45, 163-169 (2005), and has also been implicated in tumor angiogenesis (Escobar, E. et al. *Curr Vasc Pharmacol* 2, 385-399 (2004)). Separate receptors have been identified for binding by either ET-1 or AngII which are believed to be responsible for the physiological responses observed.

Accordingly, despite known roles for ET-1 and AngII, the role of Dear is currently unknown. It is believed that Dear regulates pathways distinct from those triggered by either ET-1 or AngII binding to $ET_A$, $ET_B$ or AT1 and AT2 receptors respectively. However, due to its ability to bind to both ET-1 and AngII, and the important role these molecules play in angiogenesis, hypertension and tumor progression, a better understanding of Dear's role is needed. The present invention discloses newly discovered roles for Dear and presents methods to screen for, diagnose, prognose and treat various diseases and disorders such as hypertension, pathological angiogenesis and tumor growth/metastasis.

The genomes of all organisms undergo spontaneous mutation in the course of their continuing evolution, generating variant forms of progenitor genetic sequences (Gusella, Ann. Rev. Biochem. 55, 831-854 (1986)). A variant form may confer an evolutionary advantage or disadvantage relative to a progenitor form or may be neutral. In some instances, a variant form confers an evolutionary advantage to the species and is eventually incorporated into the DNA of many or most members of the species and effectively becomes the progenitor form. However, often times the variant form confers a disadvantage that may make an individual susceptible to certain diseases or disorders. An understanding of these variants may provide for better diagnosis of existing diseases or disorders, prognosis of the risk of obtaining certain diseases or disorders, and improved, more targeted treatments.

The knowledge of specific mutations and/or polymorphisms that are disease or disorder associated help identify patients most suited to therapy with particular pharmaceutical agents (this is often termed "pharmacogenetics"). Pharmacogenetics can also be used in pharmaceutical research to assist the drug selection process. Polymorphisms are used in mapping the human genome and to elucidate the genetic component of diseases. The following references show background details on pharmacogenetics and other uses of polymorphism detection: Linder et al. (1997), Clinical Chemistry, 43, 254; Marshall (1997), Nature Biotechnology, 15, 1249; International Patent Application WO 97/40462, Spectra Biomedical; and Schafer et al. (1998), Nature Biotechnology, 16, 33.

I. Hypertension

Hypertension, or high blood pressure, is the most common chronic illness in America. The American Heart Association estimates that more than 62 million Americans over the age of six suffer from high blood pressure, and that only a minority of these people have their blood pressure under control. Left untreated, hypertension can lead to stroke, heart attack, kidney damage, congestive heart failure, and death. Uncontrolled mild-to-moderate hypertension will reduce the life expectancy of a typical 35-year-old person by 16 years. Even the mildest form of high blood pressure, "borderline hypertension," can cut one's life span by a few years and impact negatively on the quality of life.

The existence of a genetic component to hypertension is known from twin studies, which have revealed a greater concordance of blood pressure in monozygotic twins than in dizygotic twins. Similarly, biological siblings show greater concordance of blood pressure than adoptive siblings raised in the same household. Such studies have suggested that up to about 40% of the variations in blood pressure in the population are genetically determined. However, to date, a reliable genetic marker for hypertension has not been identified. Although significant gains have been made with respect to treatment, hypertension prevails as a major risk factor for heart and kidney disease, and stroke prompting the lowering of the BP level at which to start treatment.

Thus, a genetic marker for predicting one's susceptibility to hypertension is needed, as well as, a reliable method to diagnose hypertension is needed. Additionally, treatment strategies targeting the normalization of mutant genes contributing to genetic hypertension (hypertension genes) are needed.

II. Angiogenesis

Angiogenesis is a process of tissue vascularization that involves both the growth of new developing blood vessels into a tissue (neo-vascularization) and co-opting of existing blood vessels to a target site. Blood vessels are the means by which oxygen and nutrients are supplied to living tissues and waste products are removed from living tissue. Angiogenesis can be a critical biological process. For example, angiogenesis is essential in reproduction, development and wound repair. Conversely, inappropriate angiogenesis can have severe negative consequences. For example, it is only after solid tumors are vascularized as a result of angiogenesis that the tumors have a sufficient supply of oxygen and nutrients that permit it to grow rapidly and metastasize.

Angiogenesis-dependent diseases and disorders are those diseases and disorders affected by vascular growth. Such diseases represent a significant portion of diseases for which medical treatment is sought, and include inflammatory disorders such as immune and non-immune inflammation, chronic articular rheumatism and psoriasis, disorders associated with inappropriate or inopportune invasion of vessels such as diabetic retinopathy, macular degeneration, neovascular glaucoma, restenosis, capillary proliferation in atherosclerotic plaques and osteoporosis, and cancer associated disorders, such as solid tumors, solid tumor metastases, angiofibromas, retrolental fibroplasia, hemangiomas, Kaposi sarcoma, cancers which require neovascularization to support tumor growth, etc.

While methods to inhibit unwanted angiogenesis are known, few have proven clinically useful. For example, a number of therapeutic strategies exist for inhibiting aberrant angiogenesis, which attempt to reduce the production or effect of VEGF. For example, anti-VEGF or VEGF receptor antibodies (Kim E S et al. (2002), PNAS USA 99: 11399-11404), and soluble VEGF "traps" which compete with endothelial cell receptors for VEGF binding (Holash J et al. (2002), PNAS USA 99: 11393-11398) have been developed. Classical VEGF "antisense" or aptamer therapies directed against VEGF gene expression have also been proposed (U.S. published application 2001/0021772 of Uhlmann et al.). The anti-angiogenic agents used in these and similar non-VEGF targeted therapies have typically been unsuccessful. The results achieved with available anti-angiogenic therapies have therefore been generally unsatisfactory.

Thus, methods to reduce or eliminate unwanted angiogenesis are needed.

Conversely, in situations where angiogenesis is desired, such as, for example, reproduction, development, wound repair and areas of ischemia or infarction, the stimulation of angiogenesis is useful. Current methods to initiate or up-regulate angiogenesis have also typically been clinically unsuccessful and are thus needed.

Furthermore, because ET-1 is also associated with breast cancer growth and pro-malignant potential, inhibition of Dear will also be useful in decreasing tumor growth and potential to metastasize, independent of its effects on angiogenesis.

SUMMARY OF THE INVENTION

The inventors of the present invention have discovered that mutations and/or polymorphisms in Dear that enhances the expression and/or the affinity of ET-1 binding to Dear can accurately predict susceptibility to hypertension. Mutations and/or polymorphisms in Dear and human homologues thereof are encompassed in the present invention. Thus, in one embodiment of the present invention, it is possible to predict susceptibility to hypertension, to diagnose current hypertension and/or provide prognosis of the hypertension by analyzing Dear gene and/or protein. The presence of a mutation and/or polymorphism that (1) enhances Dear expression and/or (2) enhances the affinity of ET-1 binding to Dear, compared to a wild type control, is indicative of one's susceptibility to and/or current affliction with hypertension.

In addition, Dear plays a role in angiogenesis, tumor growth and pro-malignant potential. In particular, the inventors have shown that inhibitors of Dear, such as anti-Dear antibodies, decreased tumor progression and pro-malignant potential in both a rat and mouse model of cancer. Thus, in another embodiment of the present invention, methods to inhibit angiogenesis and/or tumor growth and/or pro-malignant potential are disclosed. In this embodiment, an individual is administered a compound that inhibits Dear activation, such as for example, a small molecule inhibitor, competitive inhibitor, antibody, antibody fragment, sima, aptamer, etc. Preferably, these are used in conjunction with inhibitors to other angiogenesis-associated agents such as VEGF, placental growth factors etc.

Non-limiting examples of pathological angiogenesis or disorders treated by the methods of the present invention include, inflammatory disorders such as immune and non-immune inflammation, chronic articular rheumatism and psoriasis, disorders associated with inappropriate or inopportune invasion of vessels such as diabetic retinopathy, macular degeneration, neovascular glaucoma, restenosis, capillary proliferation in atherosclerotic plaques and osteoporosis, and cancer associated disorders, such as solid tumors, solid tumor metastases, angiofibromas, retrolental fibroplasia, hemangiomas, Kaposi sarcoma and the like cancers which require neovascularization to support tumor growth. In a preferred embodiment of the present invention, the methods are directed to inhibiting tumor angiogenesis and/or pro-malignant potential in a mammal with cancer, such as, for example, breast cancer.

In a related embodiment, the present invention discloses methods to stimulate angiogenesis in tissues in need thereof. In this embodiment, activators of Dear are administered to an individual, such as, for example, small molecules, antibodies, antibody fragments, or other activators known to those of skill in the art.

As an example, stimulation of angiogenesis may be beneficial in diabetes-induced ischemia, poor circulation, myocardial infarction, aortic aneurysm, arterial disease of the lower extremities, cerebrovascular disease, etc.

BRIEF DESCRIPTION OF THE DRAWINGS

(FIG. 1A) Comparative nucleotide sequence of Dahl S and Dahl R cDNAs spanning the $T^{2814}$ (SEQ ID NO: 17) (Dahl S)/$C^{2814}$ (SEQ ID NO: 18) (Dahl R) and $T^{2901}$ (SEQ ID NO: 19) (Dahl S)/$C^{2901}$ (SEQ ID NO: 20) (Dahl R) nucleotide transitions. Amino acid substitutions resulting from the corresponding nucleotide transitions detected S44 substitution in Dahl R Dear for P44 and M74 substitution in Dahl R Dear for T74 (amino acid numbering as per Ruiz-Opazo et al. 1998) (FIG. 1B) Schematic structure of the Dahl R Dear (SEQ ID NO:2). The following functional domains are highlighted: putative AngII binding site, AngII (aa 41-48); ET-1 binding site, ET-1 (aa 60-67); amino acid S44 and M74 substituted in the Dahl S Dear by P44 and T74 respectively; potential cAMP-dependent protein kinase phosphorylation sites (S91, T108 in green); a potential internalization recognition sequence (IRS) (FIG. 1C) Western blot analysis detects equivalent levels of Dahl S (S) and Dahl R (R) Dear variants in Dahl S and Dahl R rat kidney membranes isolated from male and female rats. MW, 14.4 kDa molecular weight marker.

(FIG. 2C) Detection of the 14 kDa Dear protein (◀)by western blot analysis (ab) of Dahl R (Kid-R) and Dahl S (Kid-S) kidney (Kid) membranes; control non-transfected Cos1 cell membranes (Cos1-c), Cos1 cell membranes expressing the Dahl R S44P/M74T variant (Cos1-R) and Cos1 cell membranes expressing the Dahl S S44/M74 variant (Cos1-S). $^{125}$I-AngII west-western blot analysis (*AngII) detects binding only to Dahl S kidney membranes (Kid-S) and Cos1 cell membranes expressing the Dahl S S44/M74 variant (Cos1-S) while $^{125}$I-ET-1 west-western blot analysis (*ET-1) reveals binding to both Dahl R (Kid-R) and Dahl S (Kid-S) kidney membranes as well as to Cos1 cell membranes expressing the Dahl R S44P/M74T (Cos1-R) and Dahl S S44/M74 (Cos1-S) molecular variants.

FIG. 3D: Saturation binding curves of ligand binding studies of mouse Dear expressed in Cos-1 cells. ○, mean±sem $^{125}$I-ET-1 binding; ●, mean±sem $^{125}$I-AngII binding.

(FIG. 4A) Detection of the Dear gene variants by single strand conformation polymorphism (SSCP) analysis in different rat strains. A 137 bp PCR product spanning the S44P substitution reveals the S44P/M74T variant in Dahl R(R) and LEW strains while the S44/M74 variant is detected in Dahl S (S), BN, WKY and SHR genomic DNAs. F1 denotes F1 [R×S] subjects. Interval mapping with bootstrap-analysis for chromosome-2 in male (FIG. 4B) and female (FIG. 4C) cohorts using Map Manager QTXb 17 program. Horizontal lines (——)mark LRS values for significance of linkage. For (FIG. 4B) from top to bottom: LRS=18.4 (LOD=4.00) for highly significant, LRS=10.6 (LOD=2.30) for significant, LRS=4.1 (LOD=0.89) for suggestive; for (FIG. 4C) from top to bottom: LRS=16.6 (LOD=3.61) for highly significant, LRS=9.9 (LOD=2.15) for significant, LRS=3.9 (LOD=0.85) for suggestive. (——)Likelihood ratio statistic; (——)regression coefficient for additive effect; (——)regression coefficient for dominance effect. Histograms represent the bootstrap-based confidence intervals for the detected QTLS.

FIG. 5: Dear expression and schematic representation of the targeting vector.

FIG. 5E: Deduced amino acid sequence for mouse Dear cDNA (bottom sequence, SEQ ID NO: 24) compared with rat Dear sequence; Ab, peptide sequence used for anti-Dear antibody; AngII, angiotensin II binding site1, ET-1, endothelin-1 binding site1, TM-1, predicted transmembrane domain; IRS, internalization recognition sequence; (−), identical sequence; (*), adjusted gap for better alignment; bold lettering denotes non-conservative amino acid differences against the rat sequence on the top, SEQ ID NO: 23.

FIGS. 6A-I: Comparative anatomical analysis of Dear$^{+/+}$ (left side) and Dear$^{-/-}$ (right side) mouse embryos. FIG. 6A shows adjacent E12.5 embryos revealing prominent yolk-sac collecting vessels in Dear$^{+/+}$ (left side) but absent in the smaller Dear$^{-/-}$ embryo (right side); both embryos still attached to placentas respectively.

FIG. 6B shows adjacent E11.5 mouse embryos revealing well-developed yolk-sac collecting vessels in Dear$^{+/+}$ while absent in Dear$^{-/-}$ embryo.

FIG. 6C shows that compared to E10.5 Dear$^{+/+}$, E10.5 Dear$^{-/-}$ mouse embryo exhibits a lack of yolk-sac collecting vessels; embryo translucency allows detection of incomplete vascular network, blood filled heart and some cranial region vascularization.

FIG. 6D shows adjacent E12.5 mouse embryos distinguishing normal Dear$^{+/+}$ from darkened, resorbed Dear$^{-/-}$ embryo.

FIG. 6E shows E11.5 Dear$^{-/-}$ mouse embryo exhibiting a hypoplastic phenotype compared with age-matched, larger dysmorphic null phenotype in FIG. 6B.

FIG. 6F shows E10.5 Dear$^{-/-}$ mouse embryo exhibiting a hypoplastic phenotype compared with a slightly larger E10.5 dysmorphic null phenotype in FIG. 6C.

FIG. 6G shows high magnification of E9.5 Dear$^{+/+}$ (left panel) mouse embryo showing vascular network development from cranial to caudal region with prominent blood-filled dorsal aortae (▽) and heart (→), in contrast to E10.5 Dear$^{-/-}$ embryo (right panel) with rudimentary and abnormal vascular plexus in cranial region, an isolated blood filled heart (→), and non-detection blood-filled dorsal aortae.

FIG. 6H shows an analysis of mouse embryos revealing distinct blood-filled cardiac ventricles and vascular network throughout the body in the larger Dear$^{+/+}$ embryo, in contrast to Dear$^{-/-}$ embryo with an enlarged single-chamber blood-filled heart, minimal peripheral vascular network, absent eye pigmentation, and abnormal brain region development.

FIG. 6I shows cleared, fixed E11.5 mouse embryos shown in FIG. 6B, revealing marked developmental delay in Dear$^{-/-}$ embryo particularly in brain region development and heart chamber formation.

FIG. 7A: E10.5 Dear$^{-/-}$ yolk sac revealing sparse blood islands in primary vascular plexus with a dilated vessel (→), but absent collecting vessels. FIG. 7B: E10.5 Dear$^{+/+}$ embryo yolk-sac revealing large blood island-filled collecting vessels (+) and primary vascular plexus. FIG. 7C: Analysis of E12.5 Dear$^{-/-}$ embryos reveals abnormal hyper-convoluted neuroepithelium with disorderly demarcation of major brain regions. Central ventral section is devoid of organogenesis with no recognizable liver and gut differentiation. FIG. 7D: Analysis of littermate E12.5 Dear$^{+/+}$ embryo contrasts the dysmorphic phenotype in the Dear$^{-/-}$ mutant. Note prominent organogenesis: gut, liver, heart, brain and dorsal aorta. FIG. 7E: High magnification of Dear−/− neuroepithelial segment (proximal * in FIG. 7C) revealing thin-walled perineural vessels (→) and a hyper-cellular neuroepithelium. FIG. 7F: In contrast, high magnification of Dear+/+ neuroepithelial segment (proximal * in FIG. 7C) revealing perineural vessels (→) filled with blood islands and exhibiting relatively thicker walls. FIG. 7G: Higher magnification of Dear−/− neuroepithelium segment (distal * in FIG. 7C) showing marked cellularity with poor differential layering, absent penetrating capillaries, although a few nucleated rbcs are detected within the neuroepithelium. FIG. 7H: Higher magnification of Dear$^{+/+}$ neuroepithelium (distal * in FIG. 7D) revealing differential layering and numerous penetrating capillaries (→) with nucleated rbcs. FIGS. 7I-J: Analysis of fetal-placental connections (f-pl con/xn) (bar=160 µm) and FIGS. 7K-L: fetal-placental junctions (f-pl jxn) in E11.5 embryos shows abnormal vascular development and decreased embryonic blood cells in Dear$^{-/-}$, (bar=20 µm).

FIG. 9C-D) in perineural region and formation of vascular network (vasc net; FIG. 9E-F) in the caudal region detects deficient vascular development in Dear$^{-/-}$ embryos; bar=20 µm.

FIG. 11C: Anti-rat Dear anti-peptide specific antibody treatment (○) results in decreased tumor volume in radiation-induced rat mammary tumors. FIG. 11D: Anti-rat Dear DNA vaccine treatment (◇) also results in decreased tumor volume in radiation-induced rat mammary tumors. FIG. 11E: Representative histological analysis of Masson-trichrome stained tumor sections comparing mock-treated (mock-Rx) vector controls, anti-Dear anti-peptide specific antibody treatment (ab-Rx) and anti-rat Dear DNA-vaccine (DNA-vac) shows changes in tumor pattern, microvascular invasion and nuclear grade in anti-Dear treated tumors; bar=20 µm. Values are presented as mean±sem. *, P<0.05; , P<0.01; *, P, <0.001

DETAILED DESCRIPTION OF THE INVENTION

I. Hypertension

Figure 1A:
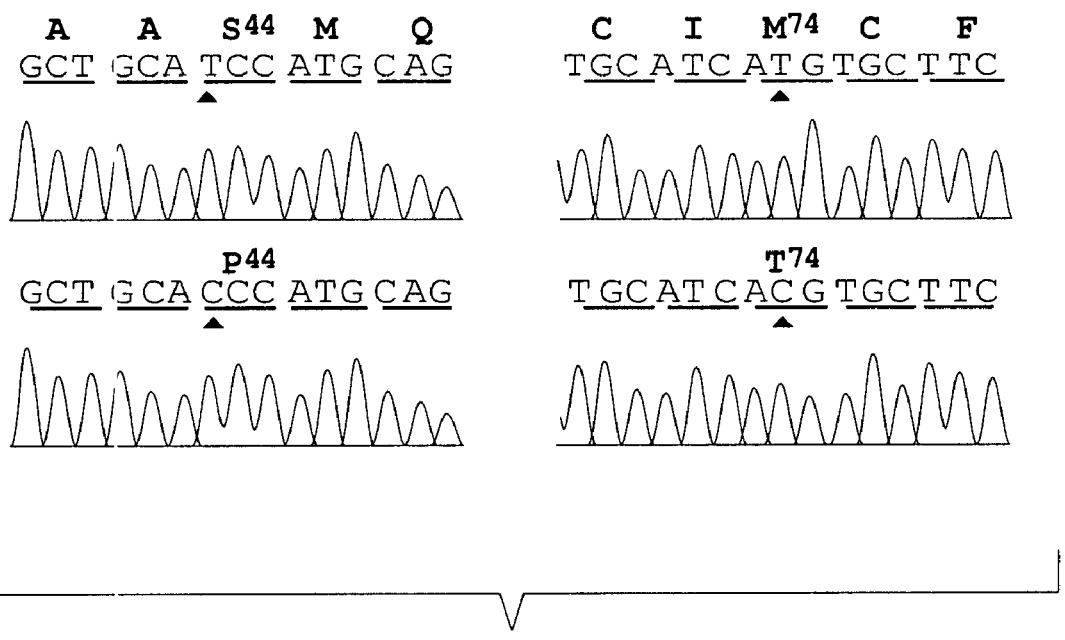
FIGS. 1A-1C. Molecular characterization of Dahl S and Dahl R Dear variants.

In one embodiment of the present invention, a method for determining an individual's susceptibility to hypertension is disclosed, as well as a diagnostic and/or prognostic method to determine the condition of the hypertension. An individual is screened for mutations and/or polymorphisms in Dear that correlate to an increase expression of Dear and/or enhancement of Dear-activation or Dear-signaling by AngII, ET-1, VEGF-signal peptide (VEGFsp) or other Dear-ligand as compared to a control. The presence of such a mutation and/or polymorphism in the test sample, as compared to the normal control, is indicative of an individual's susceptibility to hypertension. The presence of such a mutation and/or polymorphism in the test sample, as compared to the normal control, can also be indicative of a current state of hypertension.

As used herein, the term Dear encompasses Dear and human homologues thereof. In one embodiment, the term "human homologue to Dear" refers to a DNA sequence that has at least about 50% homology to SEQ ID NO:1 and more preferably at least about 60% homology or identity, including all intervals up (i.e. 55%, 60%, 65%, 70%, 75%, 80%, 85%, 90%, 95%, etc.). In one embodiment, the term "human homologue to Dear protein" refers to an amino acid sequence that has 50% homology to SEQ ID NO: 2, more preferably at least about 60% homology, still more preferably, at least about 70% homology, even more preferably, at least about 75% homology, yet more preferably, at least about 80% homology, even more preferably at least about 85% homology, still more preferably, at least about 90% homology, and more preferably, at least about 95% homology, intervals of the same are also encompassed (i.e., 55%, 60%, 70%, 75%, 80%, 85%, 90%, 95%, 98%, etc.).

"Homology" or "identity" or "similarity" refers to sequence similarity between two peptides or between two nucleic acid molecules. Homology and identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. A sequence which is "unrelated" or "non-homologous" shares less than 40% identity, though preferably less than 25% identity with a sequence of the present application.

In comparing two sequences, the absence of residues (amino acids or nucleic acids) or presence of extra residues also decreases the identity and homology/similarity. The term "homology" describes a mathematically based comparison of sequence similarities which is used to identify genes or proteins with similar functions or motifs. The nucleic acid and protein sequences of the present application may be used as a "query sequence" to perform a search against public databases to, for example, identify other family members, related sequences or homologs. Such searches can be performed using the NBLAST and XBLAST programs (version 2.0) of Altschul, et al. (1990) J Mol. Biol. 215:403-10. BLAST nucleotide searches can be performed with the NBLAST program, score=100, wordlength=12 to obtain nucleotide sequences homologous to nucleic acid molecules of the application. BLAST protein searches can be performed with the XBLAST program, score-50, wordlength=3 to obtain amino acid sequences homologous to protein molecules of the application. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and BLAST) can be used. See http://www.ncbi.nlm.nih.gov.

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ea., Oxford University Press, New York, 1988; Biocomputing: Informatics and—14 Genome Projects, Smith, D. W., ea., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988)). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 112(1): 387 (1984)), BLASTP, BLASTN, and FASTA (Altschul, S. F. et al., J. I Molec. Biol. 215: 403-410 (1990) and Altschul et al. Nuc. Acids Res. 25: 3389-3402 (1997)). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990)). The well known Smith Waterman algorithm may also be used to determine identity.

Once an individual is known to be susceptible to hypertension, currently available methods to reduce or prevent a rise in blood pressure may be used. Examples of currently available methods to reduce and/or prevent hypertension include, for example, diet, exercise, multidrug regimens including combinations of antihypertensive drugs such as beta blockers, diuretics, calcium antagonists, angiotensin II active agents, heart rate-reducing nondihydropyridine calcium antagonists, and angiotensin-converting enzyme (ACE) inhibitors. Alternatively, compounds that modulate Dear function may be administered. Where the individual already has hypertension knowing the basis for that hypertension can be used to determine treatment regime.

Methods to detect the presence or absence of mutations and/or polymorphisms in genes such as Dear are known to those of skill in the art and certain embodiments are as follows:

Preparation of Samples

Mutations and/or polymorphisms are detected in a target nucleic acid from an individual being analyzed. For example, for assay of genomic DNA, virtually any biological sample (other than pure red blood cells) is suitable. For example, convenient tissue samples include whole blood, semen, saliva, tears, urine, fecal material, sweat, buccal, skin and hair. For assay of cDNA or mRNA, the tissue sample must be obtained from an organ in which the target nucleic acid is expressed, see for example, FIG. 5B, which shows Dear expression in heart, brain, kidney, liver, spleen, lung, aorta, testis, and uterus.

Many of the methods described below require amplification of DNA from target samples. This can be accomplished by e.g., PCR. See generally PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila et al., Nucleic Acids Res. 19, 4967 (1991); Eckert et al., PCR Methods and Applications 1, 17 (1991); PCR (eds. McPherson et al., IRL Press, Oxford); and U.S. Pat. No. 4,683,202 (each of which is incorporated by reference for all purposes).

Other suitable amplification methods include the ligase chain reaction (LCR) (see Wu and Wallace, Genomics 4, 560 (1989), Landegren et al., Science 241, 1077 (1988), transcription amplification (Kwoh et al., Proc. Natl. Acad. Sci. USA 86, 1173 (1989)), and self-sustained sequence replication (Guatelli et al., Proc. Nat. Acad. Sci. USA, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

Detection of Mutations and/or Polymorphisms in Target DNA

The identity of bases occupying mutated or polymorphic sites can be determined in an individual (e.g., a patient being analyzed) by several methods, which are described in turn.

Allele-Specific Probes

The design and use of allele-specific probes for analyzing mutations and/or polymorphisms is described by e.g., Saiki et al., Nature 324, 163-166 (1986); Dattagupta, EP 235,726, Saiki, WO 89/11548. Allele-specific probes can be designed that hybridize to a segment of target DNA from one individual but do not hybridize to the corresponding segment from another individual due to the presence of different mutated or polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles. Some probes are designed to hybridize to a segment of target DNA such that the polymorphic site aligns with a central position (e.g., in a 15 mer at the 7 position; in a 16 mer, at either the 8 or 9 position) of the probe. This design of probe achieves good discrimination in hybridization between different allelic forms.

Allele-specific probes are often used in pairs, one member of a pair showing a perfect match to a reference form of a target sequence and the other member showing a perfect match to a variant form. Several pairs of probes can then be immobilized on the same support for simultaneous analysis of multiple mutations and/or polymorphisms within the same target sequence.

Tiling Arrays

The mutations and/or polymorphisms can also be identified by hybridization to nucleic acid arrays, some example of which are described by WO 95/11995 (incorporated by reference in its entirety for all purposes). The same array or a different array can be used for analysis of characterized mutations and/or polymorphisms. WO 95/11995 also describes subarrays that are optimized for detection of a variant form of a precharacterized mutation and/or polymorphism. Such a subarray contains probes designed to be complementary to a second reference sequence, which is an allelic variant of the first reference sequence. The second group of probes is designed by the same principles as described above except that the probes exhibit complementarily to the second reference sequence. The inclusion of a second group (or further groups) can be particularly useful for analyzing short subsequences of the primary reference sequence in which multiple mutations are expected to occur within a short distance commensurate with the length of the probes (i.e., two or more mutations within 9 to 21 bases).

Allele-Specific Primers

An allele-specific primer hybridizes to a site on target DNA overlapping a mutation and/or polymorphism and only primes amplification of an allelic form to which the primer exhibits perfect complementarily. See Gibbs, Nucleic Acid Res. 17, 2427-2448 (1989). This primer is used in conjunction with a second primer which hybridizes at a distal site. Amplification proceeds from the two primers leading to a detectable product signifying the particular allelic form is present. A control is usually performed with a second pair of primers, one of which shows a single base mismatch at the polymorphic site and the other of which exhibits perfect complementarily to a distal site. The single-base mismatch prevents amplification and no detectable product is formed. The method works best when the mismatch is included in the 3'-most position of the oligonucleotide aligned with the mutation and/or polymorphism because this position is most destabilizing to elongation from the primer. See, e.g., WO 93/22456.

Direct-Sequencing

The direct analysis of the sequence of mutation and/or polymorphisms of the present invention can be accomplished using either the dideoxy-chain termination method or the Maxam-Gilbert method (see Sambrook et al., Molecular Cloning, A Laboratory Manual (2nd Ed., CSHP, New York 1989); Zyskind et al., Recombinant DNA Laboratory Manual, (Acad. Press, 1988)).

Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. Erlich, ed., PCR Technology, Principles and Applications for DNA Amplification, (W. H. Freeman and Co, New York, 1992), Chapter 7.

Single-Strand Conformation Mutation and/or Polymorphism Analysis

Alleles of target sequences can be differentiated using single-strand conformation mutation and/or polymorphism analysis, which identifies base differences by alteration in electrophoretic migration of single stranded PCR products, as described in Orita et al., Proc. Nat. Acad. Sci. 86, 2766-2770 (1989). Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence difference between alleles of target sequences.

Antibody Detection Methods

According to another aspect of the present invention an antibody specific for an allelic variant (mutation and/or polymorphism) of human Dear polypeptide is used to detect the presence or absence of Dear mutations and/or polymorphisms.

Antibodies can be prepared using any suitable method. For example, purified polypeptide may be utilized to prepare specific antibodies. The term "antibodies" is meant to include polyclonal antibodies, monoclonal antibodies, and the various types of antibody constructs such as for example $F(ab')_2$, Fab and single chain Fv. Antibodies are defined to be specifically binding if they bind the allelic variant of Dear with a Ka of greater than or equal to about $10^7$ M-1. Affinity of binding can be determined using conventional techniques, for example those described by Scatchard et al., Ann. N.Y. Acad. Sci., 51:660 (1949).

Polyclonal antibodies can be readily generated from a variety of sources, for example, horses, cows, goats, sheep, dogs, chickens, rabbits, mice or rats, using procedures that are well-known in the art. In general, antigen is administered to the host animal typically through parenteral injection. The immunogenicity of antigen may be enhanced through the use of an adjuvant, for example, Freund's complete or incomplete adjuvant. Following booster immunizations, small samples of serum are collected and tested for reactivity to antigen. Examples of various assays useful for such determination include those described in: Antibodies: A Laboratory Manual, Harlow and Lane (eds.), Cold Spring Harbor Laboratory Press, 1988; as well as procedures such as countercurrent immuno-electrophoresis (CIEP), radioimmunoassay, radioimmunoprecipitation, enzyme-linked immuno-sorbent assays (ELISA), dot blot assays, and sandwich assays, see U.S. Pat. Nos. 4,376,110 and 4,486,530.

Monoclonal antibodies may be readily prepared using well-known procedures, see for example, the procedures described in U.S. Pat. Nos. 4,902,614, 4,543,439 and 4,411,993; Monoclonal Antibodies, Hybridomas: A New Dimension in Biological Analyses, Plenum Press, Kennett, McKearn, and Bechtol (eds.), (1980).

Monoclonal antibodies to variant forms of Dear can be produced using alternative techniques, such as those described by Alting-Mees et al., "Monoclonal Antibody Expression Libraries: A Rapid Alternative to Hybridomas", Strategies in Molecular Biology 3: 1-9 (1990) which is incorporated herein by reference. Similarly, binding partners can be constructed using recombinant DNA techniques to incorporate the variable regions of a gene that encodes a specific binding antibody. Such a technique is described in Larrick et al., Biotechnology, 7: 394 (1989).

Once isolated and purified, the antibodies may be used to detect the presence of variant Dear in a sample using established assay protocols, see for example "A Practical Guide to ELISA" by D. M. Kemeny, Pergamon Press, Oxford, England. As is known to those of skill in the art, a suitable control sample (i.e. a sample with wild type or non-mutated and/or polymorphic Dear) is used as a control.

Also encompassed are methods for the determination of expression levels. For example, the overexpression of Dear is an indication that an individual is susceptible to or is currently afflicted with hypertension. Methods for analyzing expression levels are known to those of skill in the art. In one aspect of the invention, Dear levels present in a test biological sample are measured by analyzing the level of Dear mRNA in a test sample and comparing this level to the level of Dear in a control sample. In another embodiment, Dear levels present in a test biological sample are measured by contacting the test sample, or preparation thereof, with an endogenous control 18S rRNA. A preferred embodiment of the present invention is the use of laser capture microdissection and RT-PCR for the analysis of Dear mRNA from tissue samples. Laser capture microdissection is known to those of skill in the art and described, for example, in Simon et al. (1998) Trends in Genetics 14:272 and Emmert-Buck et al. (1996) Science 274: 998-1001.

In another aspect of the invention, Dear levels present in a test biological sample are measured by contacting the test sample, or preparation thereof, with an antibody-based binding moiety that specifically binds to Dear protein, or to a portion thereof. The antibody-based binding moiety forms a complex with Dear that can be detected, thereby allowing the levels of Dear to be measured.

Any means known to those skilled in art can be used to assess Dear levels. For example, in some embodiments Dear expression levels are assayed by measuring levels of Dear via mass spectrometry, ELISA, MR, CT, PET targeted at Dear or immunohistochemistry.

In a further embodiment, the invention provides for kits that comprise means for measuring Dear in a biological sample.

DEFINITIONS

"Dear", "DEAR", or "Dear" as used herein and throughout is the Dual Endothelin-1/Angiotensin II Receptor.

Polymorphism refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles.

The allelic form occurring most frequently in a selected population is sometimes referred to as the wild type form. Diploid organisms may be homozygous or heterozygous for allelic forms. A diallelic polymorphism has two forms. A triallelic polymorphism has three forms.

A single nucleotide polymorphism occurs at a polymorphic site occupied by a single nucleotide, which is the site of variation between allelic sequences. The site is usually preceded by and followed by highly conserved sequences of the allele (e.g., sequences that vary in less than {fraction ($1/100$)} or {fraction ($1/1000$)} members of the populations).

A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

II. Angiogenesis

A. Inhibiting Angiogenesis

In another embodiment of the present invention, a method of inhibiting angiogenesis in a tissue of an individual having a disease or disorder dependent or modulated by angiogenesis, wherein the disease or disorder can be treated by the inhibition of angiogenesis is disclosed. Generally, the method comprises administering to the tissue a composition comprising an angiogenesis-inhibiting amount of Dear inhibitor.

In a related embodiment, the methods of the present invention provide for a method of inhibiting angiogenesis in a tissue of an individual at risk for developing an angiogenic disease or disorder.

Where the growth of new blood vessels is the cause of, or contributes to, the pathology associated with a disease, inhibition of angiogenesis will reduce the deleterious effects of the disease. Examples include tumors, rheumatoid arthritis, diabetic retinopathy, inflammatory diseases, restenosis, and the like. Where the growth of new blood vessels is required to support growth of a deleterious tissue, inhibition of angiogenesis will reduce the blood supply to the tissue and thereby contribute to reduction in tissue mass based on blood supply requirements. Examples include growth of tumors where neovascularization is a continual requirement in order that the tumor growth beyond a few millimeters in thickness, and for the establishment of solid tumor metastases. Another example is coronary plaque enlargement.

The invention provides for a method for the inhibition of angiogenesis in a tissue, and thereby inhibiting events in the tissue which depend upon angiogenesis.

The treatment will involve the administration of a Dear inhibitor. The treatment may involve a combination of treatments, including, but not limited to a Dear inhibitor in combination with other angiogenic inhibitors, chemotherapy, radiation, surgery, or other treatments known to those of skill in the art to inhibit angiogenesis. Examples of angiogenic inhibitors that may be used in combination with the Dear inhibitor of the present invention are: direct angiogenesis inhibitors, Angiostatin, Bevacizumab (Avastin), Arresten, Canstatin, Combretastatin, Endostatin, N M-3, Thrombospondin, Tumstatin, 2-methoxyestradiol, and Vitaxin; and indirect angiogenesis inhibitors: ZD1839 (Iressa), ZD6474, OS1774 (Tarceva), CI1033, PKI1666, IMC225 (Erbitux), PTK787, SU6668, SU11248, Herceptin, and IFN-α, CELEBREX® (Celecoxib), THALOMID® (Thalidomide), and IFN-α.

Thus, in connection with the administration of a Dear inhibitor, a compound which inhibits angiogenesis indicates that administration in a clinically appropriate manner results in a beneficial effect for at least a statistically significant fraction of patients, such as improvement of symptoms, a cure, a reduction in disease load, reduction in tumor mass or cell numbers, extension of life, improvement in quality of life, or other effect generally recognized as positive by medical doctors familiar with treating the particular type of disease or condition.

Examples of Dear inhibitors include, but are not limited to, molecules which block the binding of AngII, ET-1 and/or other ET-1 or AngII-like ligands to Dear, compounds which interfere with downstream signaling events of Dear, or other compounds or agents that inhibit activation of the receptor. Such compounds include antibodies that bind to Dear and prevent binding of AngII, ET-1 or other mimetic ligands. Preferably, the antibody is a humanized antibody. Preferably, the antibody is a single chain antibody or $F(ab)^2$ fragment. Other inhibitors including small molecules that bind to the Dear domain that binds to ET-1, soluble Dear receptors, peptides containing the Dear ET-1 and/or AngII binding domains, etc.

There are a variety of diseases or disorders in which angiogenesis is believed to lead to negative consequences, referred to as pathological angiogenesis, including but not limited to, inflammatory disorders such as immune and non-immune inflammation, chronic articular rheumatism and psoriasis, disorders associated with inappropriate or inopportune invasion of vessels such as diabetic retinopathy, neovascular glaucoma, restenosis, capillary proliferation in atherosclerotic plaques and osteoporosis, and cancer associated disorders, such as solid tumors, solid tumor metastases, angiofibromas, retrolental fibroplasia, hemangiomas, Kaposi sarcoma and the like cancers which require neovascularization to support tumor growth. In a preferred embodiment of the present invention, the methods are directed to inhibiting angiogenesis in a mammal with cancer.

As described herein, any of a variety of tissues, or organs comprised of organized tissues, can support angiogenesis in disease conditions including skin, muscle, gut, connective tissue, joints, bones and the like tissue in which blood vessels can invade upon angiogenic stimuli.

The individual treated in the present invention in its many embodiments is desirably a human patient, although it is to be understood that the principles of the invention indicate that the invention is effective with respect to all mammals, which are intended to be included in the term "patient". In this context, a mammal is understood to include any mammalian species in which treatment of diseases associated with angiogenesis is desirable, particularly agricultural and domestic mammalian species.

In a preferred embodiment, the present invention is directed to methods of inhibiting angiogenesis in a tissue of a mammal having pathological angiogenesis as in cancer, and in particular breast cancer and the administration of the Dear inhibitor eliminates or reduces the presence of the cancer.

B. Enhancing Angiogenesis

In an alternative embodiment of the present invention, Dear activators are used to stimulate angiogenesis in tissues or organs in need of neovascularization or additional blood supply. In these instances, delivery of a Dear activator alone or in combination with other angiogenesis stimulators may be beneficial.

Any condition that would benefit from increased blood flow are encompassed such as, for example, gangrene, diabetes, poor circulation, arteriosclerosis, atherosclerosis, coronary artery disease, myocardial ischemia, myocardial infarction, aortic aneurysm, arterial disease of the lower extremities, cerebrovascular disease, etc. In this manner, the methods of the invention may be used to treat peripheral vascular diseases by administering Dear activators to promote vascularization. Likewise, the Dear activators are useful to treat a diseased or hypoxic heart, particularly where vessels to the heart are partially or completely obstructed. Other organs with arterial sclerosis may benefit from Dear activation. Likewise, organs whose function may be enhanced by higher vascularization may be improved by an activation of Dear. This includes kidneys or other organs which need an improvement in function. In the same manner, other disorders which could benefit from increased blood flow include ischemic bowel disease, cerebro vascular disease, impotence of a vascular basis, and the like. Additionally, formation of new blood vessels in the heart is critically important in protecting the myocardium from the consequences of coronary obstruction. Administration of a Dear activator into ischemic myocardium can enhance the development of collaterals, accelerate the healing of necrotic tissue and prevent infarct expansion and cardiac failure.

Additionally, Dear activators are useful to prepare a transplant site for tissues or organs of interest by increasing vascularization. Such organ transplants include, but are not limited to, pancreas, kidney, heart, lung, liver, etc. Dear activators may also be used in combination with other implants as a surgical adhesion barrier.

Following in vitro fertilization, the embryo is implanted in a female for gestation. The methods of the invention can be used to prepare the uterine vascularized bed for embryo implantation. In this embodiment, Dear activators are introduced prior to implantation so as to promote blood vessel formation in the uterine wall prior to implantation of the embryo, thus promoting fetal-maternal vascular plexus. Likewise, Dear activators can also enhance fetal-maternal vascular plexus formation, and/or robust placental vasculature for successful pregnancy/gestation of both natural and in vitro fertilized embryos.

Skilled artisans are able to determine when therapy is beneficial and where therapy is contraindicated. In general, patients with known tumors or pathological angiogenesis should not be given the Dear activators of the present invention.

III. Tumor pro-malignant potential: decreasing pro-malignant potential of tumors. In another embodiment of the present invention, a method of decreasing the pro-malignant potential of a tumor is disclosed. Generally, the method consists of administering to the tumor, systemically or locally, a composition comprising a Dear inhibitor at a dose which decreases pro-malignant parameters such as, but not all inclusive, nuclear pleomorphism, nuclear hyperchromasia, vascular invasion, mosaic tumor vessels, chaotic tumor vessels, tumor metastasis, etc.

Formulations

The Dear activators and inhibitors of the present invention may be administered to an individual via intravenous (I.V.), intramuscular (I.M.), subcutaneous (S.C.), intradermal (I.D.), intraperitoneal (I.P.), intrathecal (I.T.), intrapleural, intrauterine, rectal, vaginal, topical, intratumor and the like. The Dear modulators (either activators or inhibitors) can be administered parenterally by injection or by gradual infusion over time and can be delivered by peristaltic means.

Administration may be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays, for example, or using suppositories. For oral administration, the compounds of the invention are formulated into conventional oral administration forms such as capsules, tablets and tonics.

For topical administration, the pharmaceutical composition (inhibitor or activator of Dear activity) is formulated into ointments, salves, gels, or creams, as is generally known in the art.

The activators and inhibitors of Dear are conventionally administered intravenously, as by injection of a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. Precise amounts of active ingredient required to be administered depend on the judgment of the practitioner and are peculiar to each individual.

The Dear activators and inhibitors useful for practicing the methods of the present invention are of any formulation or drug delivery system containing the active ingredients, which is suitable for the intended use, as are generally known to those of skill in the art. Suitable pharmaceutically acceptable carriers for oral, rectal, topical or parenteral (including inhaled, subcutaneous, intraperitoneal, intramuscular and intravenous) administration are known to those of skill in the art. The carrier must be pharmaceutically acceptable in the sense of being compatible with the other ingredients of the formulation and not deleterious to the recipient thereof.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects.

Formulations suitable for parenteral administration conveniently include sterile aqueous preparation of the active compound which is preferably isotonic with the blood of the recipient. Thus, such formulations may conveniently contain distilled water, 5% dextrose in distilled water or saline. Useful formulations also include concentrated solutions or solids containing the compound which upon dilution with an appropriate solvent give a solution suitable for parental administration above.

For enteral administration, a compound can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a conventional carrier, e.g., cocoa butter or Witepsol S55 (trademark of Dynamite Nobel Chemical, Germany), for a suppository base.

Formulations for oral administration may be presented with an enhancer. Orally-acceptable absorption enhancers include surfactants such as sodium lauryl sulfate, palmitoyl carnitine, Laureth-9, phosphatidylcholine, cyclodextrin and derivatives thereof; bile salts such as sodium deoxycholate, sodium taurocholate, sodium glycochlate, and sodium fusidate; chelating agents including EDTA, citric acid and salicylates; and fatty acids (e.g., oleic acid, lauric acid, acylcamitines, mono- and diglycerides). Other oral absorption enhancers include benzalkonium chloride, benzethonium chloride, CHAPS (3-(3-cholamidopropyl)-dimethylammonio-1-propanesulfonate), Big-CHAPS(N,N-bis(3-D-gluconamidopropyl)-cholamide), chlorobutanol, octoxynol-9, benzyl alcohol, phenols, cresols, and alkyl alcohols. An especially preferred oral absorption enhancer for the present invention is sodium lauryl sulfate.

Alternatively, the compound may be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," Drug Carriers in Biology and Medicine, pp. 287-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

In one embodiment, the Dear activator or inhibitor of the present invention can be formulated into a liposome, microparticle, nanoparticle, etc. which is suitably sized to lodge in capillary beds following intravenous administration. When the liposome, microparticle or nanoparticle is lodged in the capillary beds surrounding ischemic tissue, the agents can be administered locally to the site at which they can be most effective. Suitable liposomes for targeting ischemic tissue are generally less than about 200 nanometers and are also typically unilamellar vesicles, as disclosed, for example, in U.S. Pat. No. 5,593,688 to Baldeschweiler, entitled "Liposomal targeting of ischemic tissue," the contents of which are hereby incorporated by reference.

Preferred particles are those prepared from biodegradable polymers, such as polyglycolide, polylactide and copolymers thereof. Those of skill in the art can readily determine an appropriate carrier system depending on various factors, including the desired rate of drug release and the desired dosage.

In one embodiment, the formulations are administered via catheter directly to the inside of blood vessels. The administration can occur, for example, through holes in the catheter. In those embodiments wherein the active compounds have a relatively long half life (on the order of 1 day to a week or more), the formulations can be included in biodegradable polymeric hydrogels, such as those disclosed in U.S. Pat. No. 5,410,016 to Hubbell et al. These polymeric hydrogels can be delivered to the inside of a tissue lumen and the active compounds released over time as the polymer degrades. If desirable, the polymeric hydrogels can have microparticles or liposomes which include the active compound dispersed therein, providing another mechanism for the controlled release of the active compounds.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into desired unit dosage form.

The formulations may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

Compounds of the present methods may be presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, preferably less than 10 microns, more preferably between 2 and 5 microns.

Generally for nasal administration a mildly acid pH will be preferred. Preferably the compositions of the invention have a pH of from about 3 to 5, more preferably from about 3.5 to about 3.9 and most preferably 3.7. Adjustment of the pH is achieved by addition of an appropriate acid, such as hydrochloric acid.

The preparation of a pharmacological composition that contains active ingredients dissolved or dispersed therein is well understood in the art and need not be limited based on formulation. Typically such compositions are prepared as injectables either as liquid solutions or suspensions, however, solid forms suitable for solution, or suspensions, in liquid prior to use can also be prepared. The preparation can also be emulsified.

The following is the sequence for rat Dear:

```
Rattus norvegicus dual endothelin 1, angiotensin II receptor (Dear),
mRNA: GeneID: 446170 Locus tag: RGD:1303105
                                                             (SEQ. ID. NO. 1)
    1 tttctaaatg attacttttc tagataccctg tttacaaaac agaagatcct ccctttgaaa 61 ccaaactaaa ctacacttga agaatataaa gtgcacaaag gaagaccacg atgaatcagt 121 accacccatc ttcccagcat tcaagaatgt tcagcgcaca ggaggtgcac agtaagtgtt 181 cctgagagga gtggatacaa cactcaatta tctgggcatg taatgctgat ctgcggtttc 241 ctttacatca gccggcctcc ttcccggttg ggatcaagga agtgaacaga tgcagactca 301 ctctggcagg caccactgag ccagccattt actctcactg catagcaaag ttattttgtc 361 aacttgtttc caggatcctc tgcttccaca gagcagaaac acctcgtcta ggggattctg 421 atccttaccc tcttctttac atttctctct ccagagaagg ttatcctcag ccaaaatcct 481 ccagtatcga cacgtctgag ccgcttgcag caggtctttg ggttccagga atgaaagtac 541 atagagtgcc agctatggaa aaggaaataa gggaggcaca ctcagacaca tcacagaaga 601 aaggttactc tacgaagggt gagcattgag ctgggactgc tggatttcag tgggctgaac 661 gaatcaagag aagcagcatt ttaagagcaa agaaaatgct catcattctc acattaggaa 721 tctgaggctt tactctgggt aacctgtgat tctattggta tttccttaca aagtgagaac 781 aatgccactt atcacaagtt tcttgtgtga gcccagtgct caagctctta gataatccaa 841 ataaatgttg ataaagagac tttatattgt tcataccaat tatcaaaaaa tacaagtaca 901 tttcatgtca gtgtggtaat aatgtttaa ataacacact tccctacagg gttaagtcta 961 tgccattatt cttccacgca gacataaagc acttcccaaa tgaagaacac cccagtagtc 1021 agaaacaaaa accatagctg atatgctaag acagggctct ctcctttgta acttcttttt 1081 tcctcaggaa gtctttgaaa gaacacagaa gccaagagaa tcttttgggg ttttaccttt 1141 tattaatcat ctgtgcttac ttcttaaaat tctaaaacac tttcaaattt gggggactgg 1201 tgatggctca gtcagtaagg tttcatgaag atgagggatc ggatcctggc agtcttggaa 1261 agtcaggcat ggcagttcta gctatagtca ctgctcactg gacagccagc caccgtagct 1321 aaaggcgtaa gctccagact cagtgaaaga cgacatggca aaaacaacat ggatcagctg
```

-continued

```
1381 agggatacac ctctggcctc cacgggcaca tacgtgcagg agcatctgaa tgtacttatg 1441 tatacccaca cgaatacata cacatcctac acacatacac actctacagg aggtatcggg 1501 catgtaagat aatccagacg aatattcact tcacgccctg atggcagcaa agggatctcg 1561 tgttactttc ataagtttag tcaaagagtt ctgatgtaga aaaagctcac aagagcaaac 1621 acttttcttc tgggacactg tcacctttaa aaagtactca aaagggggga aagtgccagg 1681 aaaaagatga tttatcaatt tgctttcccc cagaattata ttttaattca tcaattttac 1741 tcaaatctaa tgccagattc taactaggac tatatttaat gccactagga ctttagagtg 1801 atcatctaag aaaggagaaa gcaagactct tcctgttcaa atgaggtttc gggatcatct 1861 gtatgaagga tgtggtagtt ttttgatgct gtcttttaa ctgctattta taacatgtgt 1921 atagtaattt gagaaaatat ggactatggg gcattatcta atatcacatt atttcttcct 1981 tttgataaaa attaagctat gaagtctaat gtcaatatgt gcattatatt taaaccatca 2041 gccacacatg gctgtatgac taagtgccta agaatccaat tttttgtgg tatctctctc 2101 tctccctctc tccgtatgtg tgtgtctttc tctgtctctg tctctctctc tctttctctc 2161 tgacgaagga tgataagtag aaatgccata aaaacatata gataaatttt atatattggg 2221 ggctggagag atggctcagt ggttgagaac actgactgtt cttcagaggt cctgagttaa 2281 attcccagca accacatggt agctcacaac catctatatt gcatctgatg ccctcttctg 2341 gtgtgtctaa agacagctac cggtatactt acatataata aataaatctt taaaaaaatt 2401 ttttatatat taaaaaaaaa tcacataatg taataaccag gagaaatacg aacaatcgat 2461 aaaattactg gtcttgaagg ggcattaaat aattagcaaa ataaaaacaa aattaatatt 2521 gttgcttagt gaatccagaa ttttgaaaac atccactata tataataaac ataccaacta 2581 actaaagtca gccttagat aacccaggga aaactgaaga gactcggcga cttcacatga 2641 agccttactt tatccaagcg gaagaaagca gcaccttggt atgagcacac tttatgtaac 2701 agctgtacca aaaagccaca gcagtttgcc aaagtgtcaa gccatgatga gcaggacact 2761 gcttacaggc atggctatgt atctggacag cagccatgcg ggtgctgcat ccatgcaggt 2821 gagctggccg cccttactca cctctttggg gagcaaggag atgaagtctc gctggaactg 2881 gggctcgatc acttgcatca tgtgcttcac ttgtgtgggt tcacagctat cgatgagctc 2941 atctaaggcc agcaacttct ctggtccact ccagctctac caaagaggaa ttggacacat 3001 tacaaatcca tacagaagac caccagcacc tgcatggcca tgttcgagca gtggaactac 3061 atgaaagggg accgtggaca gagaccttgt ctccagaagc caccgagcg atagcagttt 3121 ttagtttcag caagtttact cagtaccttt cccgcaaagc attaaaagtc atgactggca 3181 gaaaaataag tctgcattta tttttaatta taagacttat gctaacacca agacactggg 3241 agacacacaa tatccatctg ggttattgac tag Translation =
                                                        (SEQ. ID. NO. 2)
"MSTLYVTAVPKSHSSLPKCQAMMSRTLLTGMAMYLDSSHAGAASMQVSWPPLLTSLGSKEMKSRWNWGSI

TCIMCFTCVGSQLSMSSSKASNFSGPLQLYQRGIGHITNPYRRPPAPAWPCSSSGTT"
```

EXAMPLE 1

Figure 1B:
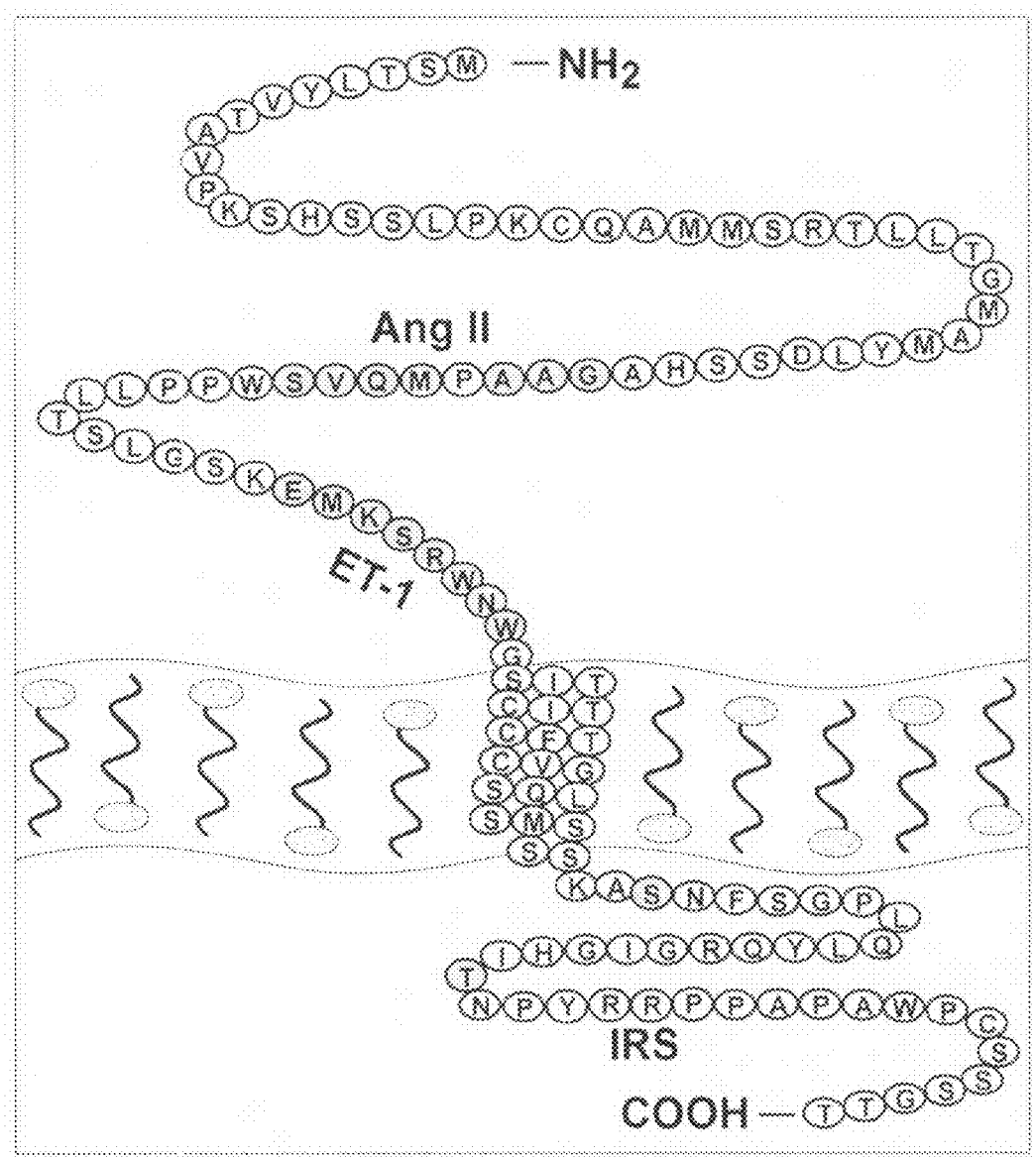

The inbred Dahl/JR rat model is an established model of human essential hypertension comprised of a salt-sensitive, hypertensive strain (Dahl S) with its cognate salt-resistant, normotensive control strain (Dahl R) (52). To investigate the involvement of Dear in hypertension pathogenesis we obtained cDNAs spanning the entire amino acid coding region for both Dahl S and Dahl R receptors. Two nucleotide differences were detected resulting in two non-conservative amino acid substitutions: $T^{2814}$ (Dahl S)/$C^{2814}$ (Dahl R) nucleotide transition resulting in S44P substitution and $T^{2901}$ (Dahl S)/$C^{2901}$ (Dahl R) nucleotide transition resulting in M74T substitution (FIG. 1A, 1B). The S44P substitution is located in the putative AngII binding site in the extracellular domain; while the M74T substitution is located in the putative transmembrane domain (FIG. 1B). The Dahl S cDNA nucleotide sequence is identical to the previously reported Sprague Dawley rat brain Dear cDNA (1). We note that both the Dahl S and Dahl R rat strains were derived from the Sprague Dawley strain (52).

Figure 1C:
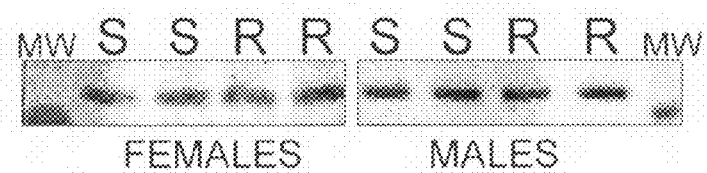
Figure 2A:
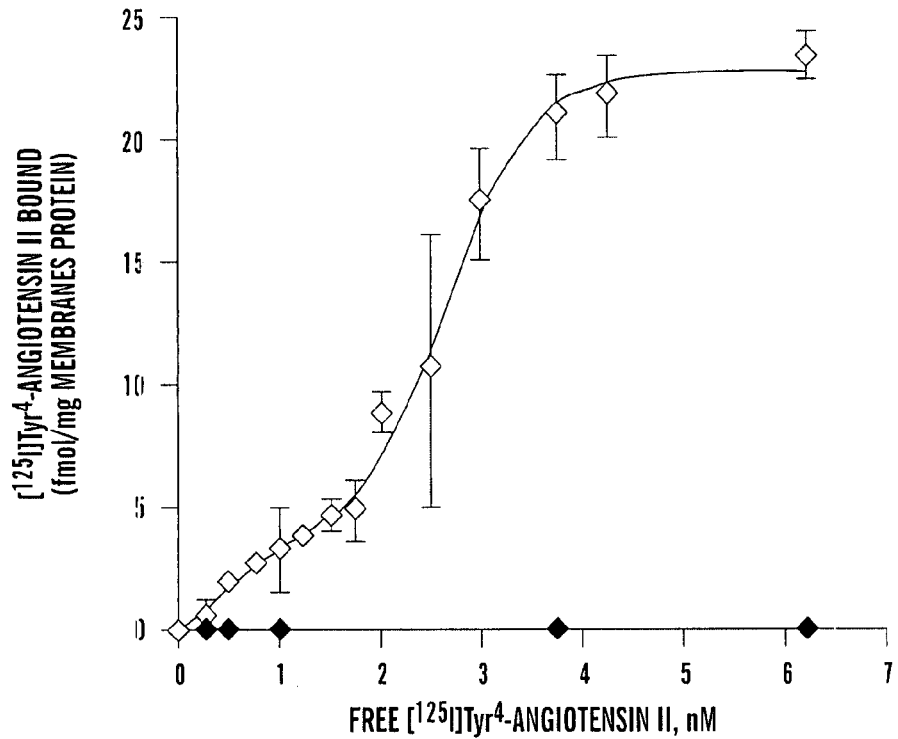
FIGS. 2A-2C. Functional characterization of Dahl S and Dahl R Dear variants. Saturation binding curves of ligand binding studies of Dahl S (○) and Dahl R(•) Dear expressed in Cos1 cells with radiolabeled $^{125}$I-AngII (FIG. 2A) and $^{125}$I-ET-1 (FIG. 2B). Values are presented as Mean±standard deviation from five independent experiments.
Figure 2B:
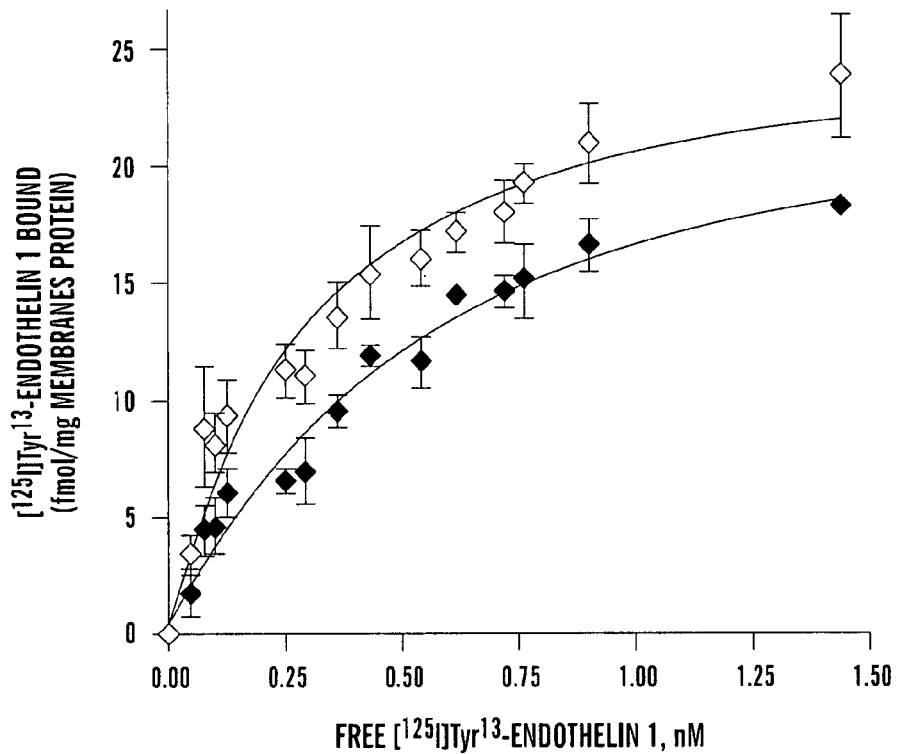
Figure 2C:
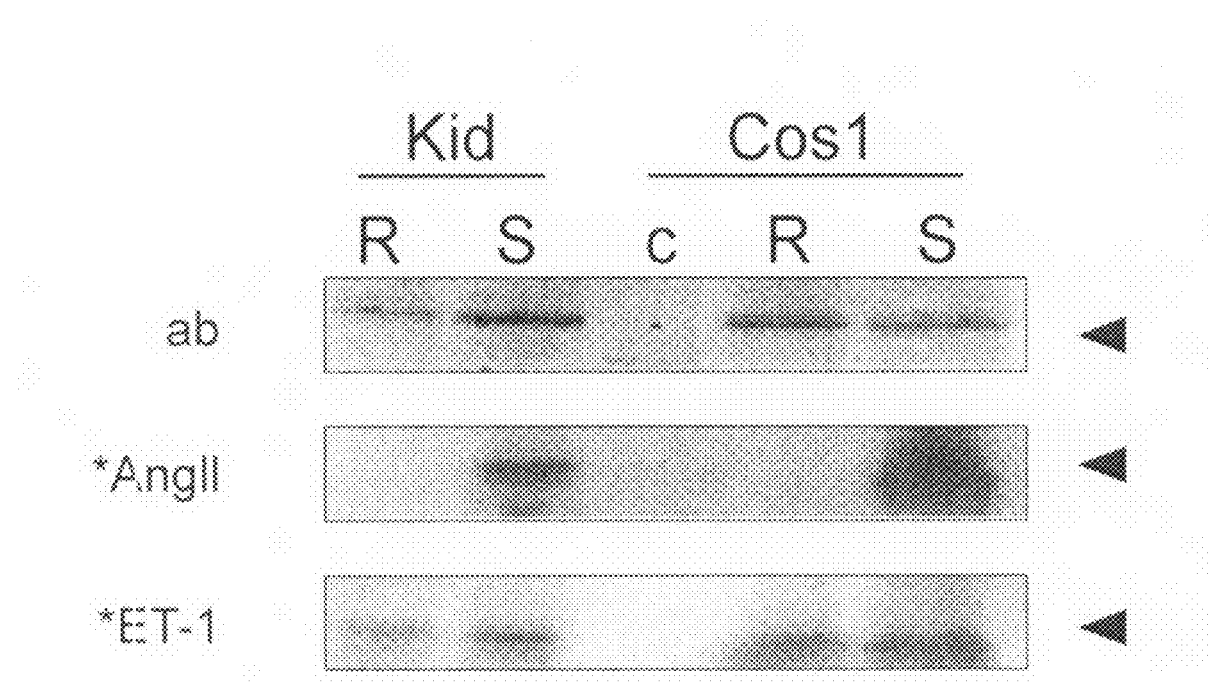
Figure 3A:
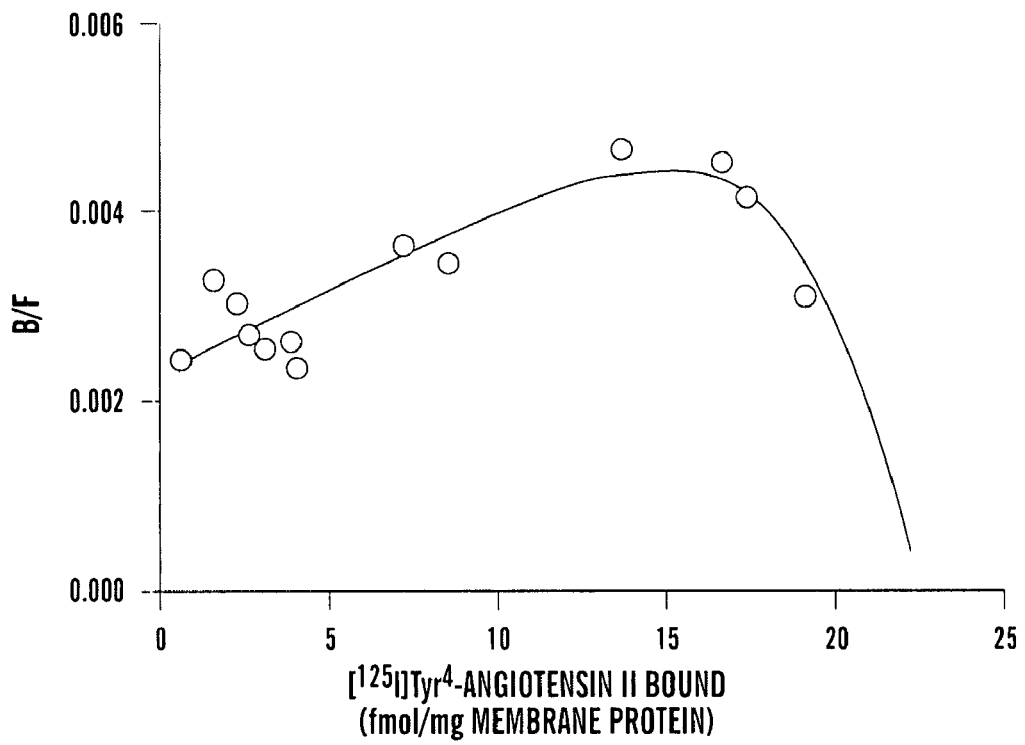
FIGS. 3A-3D. Scatchard plots of saturation data for Dahl S and Dahl R Dear variants. Scatchard plots of $^{125}$I-AngII (FIG. 3A) and $^{125}$I-ET-1 (FIG. 3B, FIG. 3C) saturation binding data of Dahl S (○) and Dahl R (•) Dear expressed in Cos1 cells.
Figure 3B:
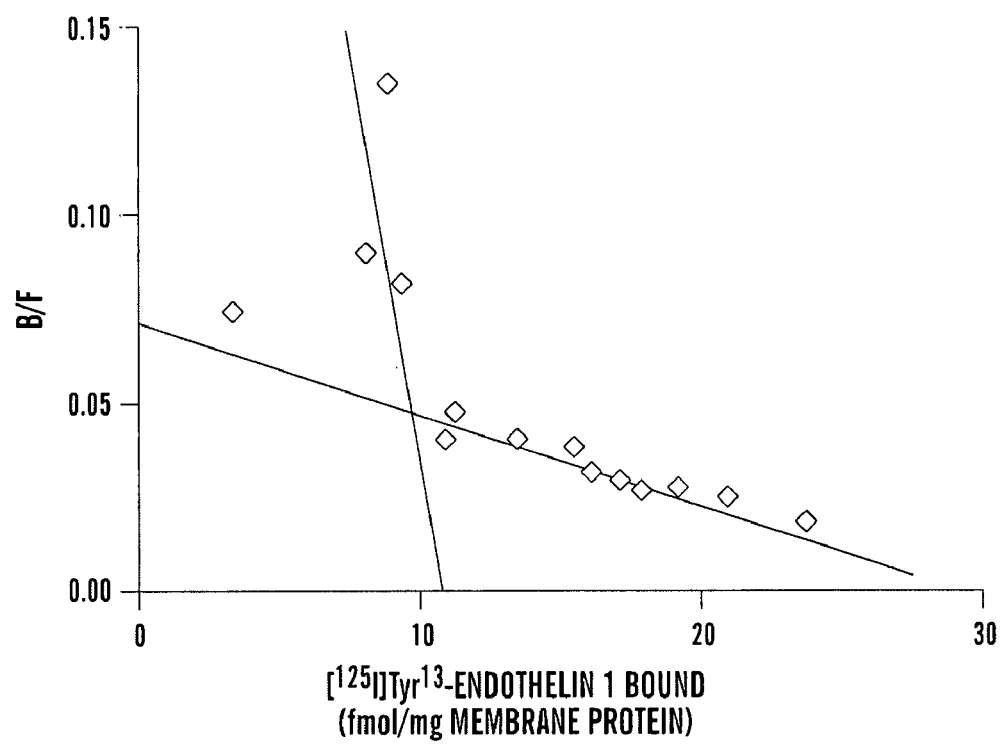
Figure 3C:
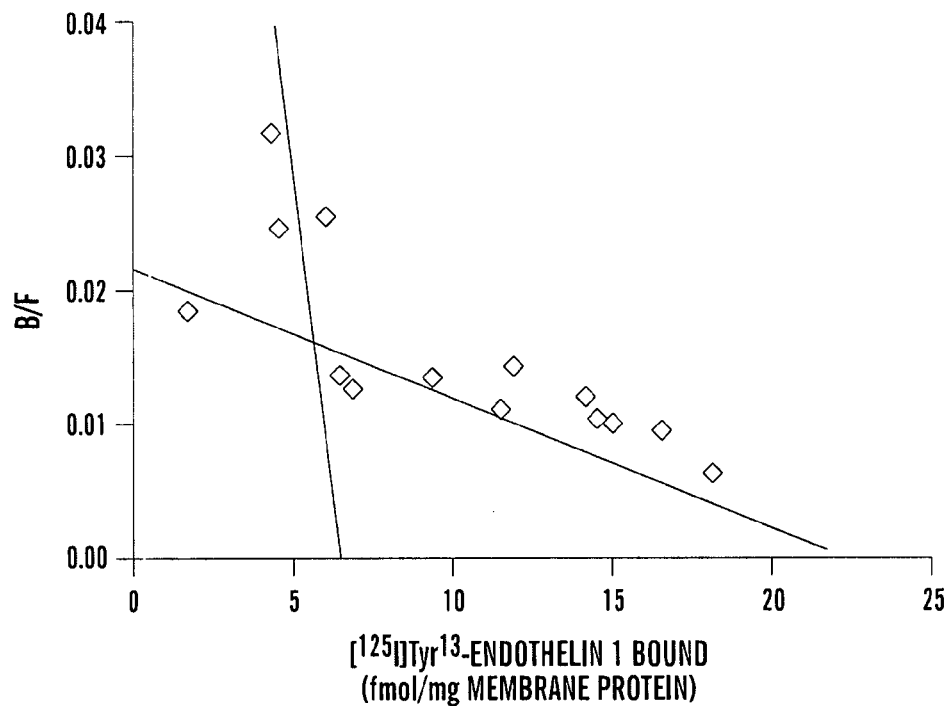
Figure 3D:
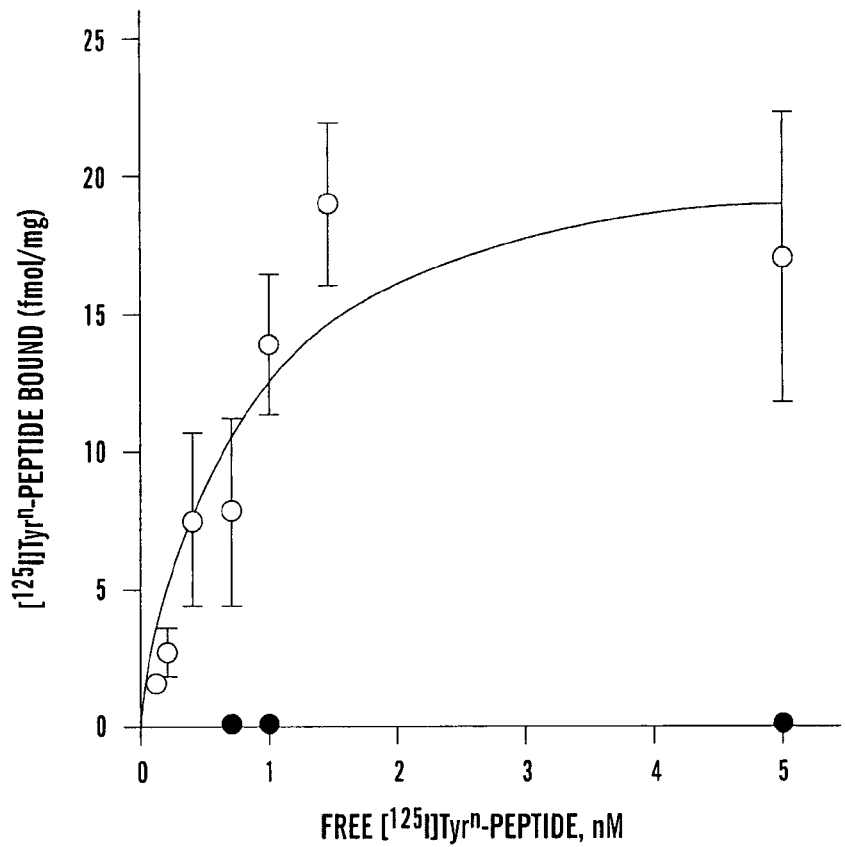

The S44P substitution spans the predicted AngII binding domain within the Dahl R Dear variant (1) (FIG. 1B) suggesting the hypothesis that AngII-binding will most likely be different between Dahl S and Dahl R receptors. In order to examine this hypothesis, we first determined that there is no significant difference in Dear expression levels between Dahl S and Dahl R rats at 12 weeks of age in both male and female rats as detected by western blot analysis comparing Dahl S and Dahl R kidney membranes (FIG. 1C). To examine hormone binding, both Dahl S and Dahl R receptors were transiently expressed in Cos1 cells respectively and tested for both AngII and ET-1 binding. Dahl R Dear do not exhibit AngII binding, but exhibit normal ET-1 binding as shown by direct radioligand binding (FIG. 2 and Table 1), and by west-western blot analysis (i.e., labeled ligand [west] binding to receptor polypeptide on western blot) of Dahl S and Dahl R rat kidney membranes and Dahl S and Dahl R Dear Cos1-transfectant cell membranes (FIG. 2C). These data demonstrate that the Dahl S Dear variant is a dual receptor binding both ET-1 and AngII similar to the brain-derived clone first characterized (1), but that the Dahl R Dear variant responds solely to ET-1 stimulation. Two affinity binding sites for ET-1 are detected in Dahl S and Dahl R receptors (FIG. 3, Table 1) and two affinity binding sites for AngII in Dahl S receptors (FIG. 3, Table 1) consistent with previous characterization (1). Furthermore, when compared to the Dahl R Dear S44P/M74S variant, the Dahl S Dear S44/M74 variant exhibits 3-fold increased affinity for ET-1 (Dahl R: S44P/M74T $K_H$ ET-1=12.0±1.12 pM; Dahl S: S44/M74 $K_H$ ET-1=4.42±0.89 pM, P<0.001, Table 1)—suggesting an enhanced response of the Dahl S receptor to ET-1 stimulation compared to the Dahl R receptor.

Based on its localization to the predicted AngII-binding site, it is likely that the S44P substitution accounts for the observed absent AngII binding in Dahl R Dear. Interestingly, this S44P substitution and resultant differential AngII binding elucidates for the first time a natural occurring mutation within a peptide-ligand binding domain predicted by the molecular recognition theory (1).

Figure 4A:
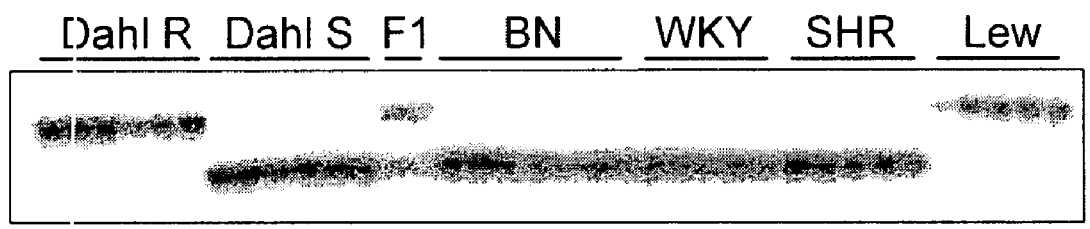
FIGS. 4A-4C. Detection and genetic analysis of Dear variants.
Figure 4B:
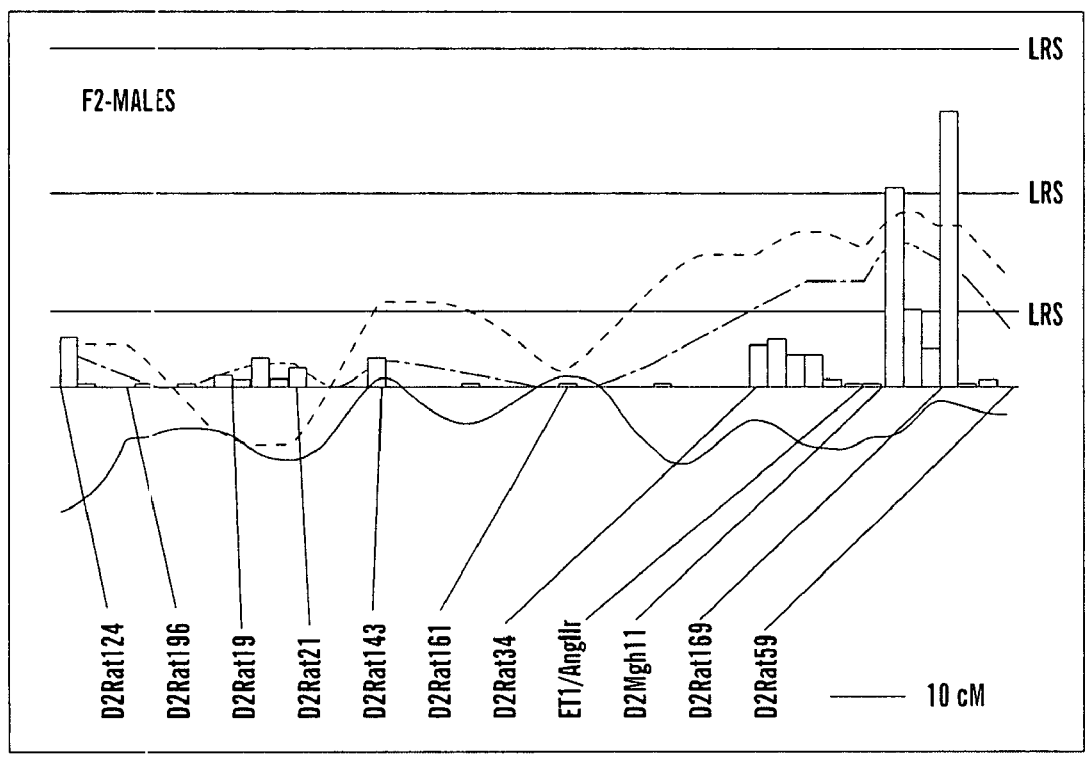
Figure 4C:
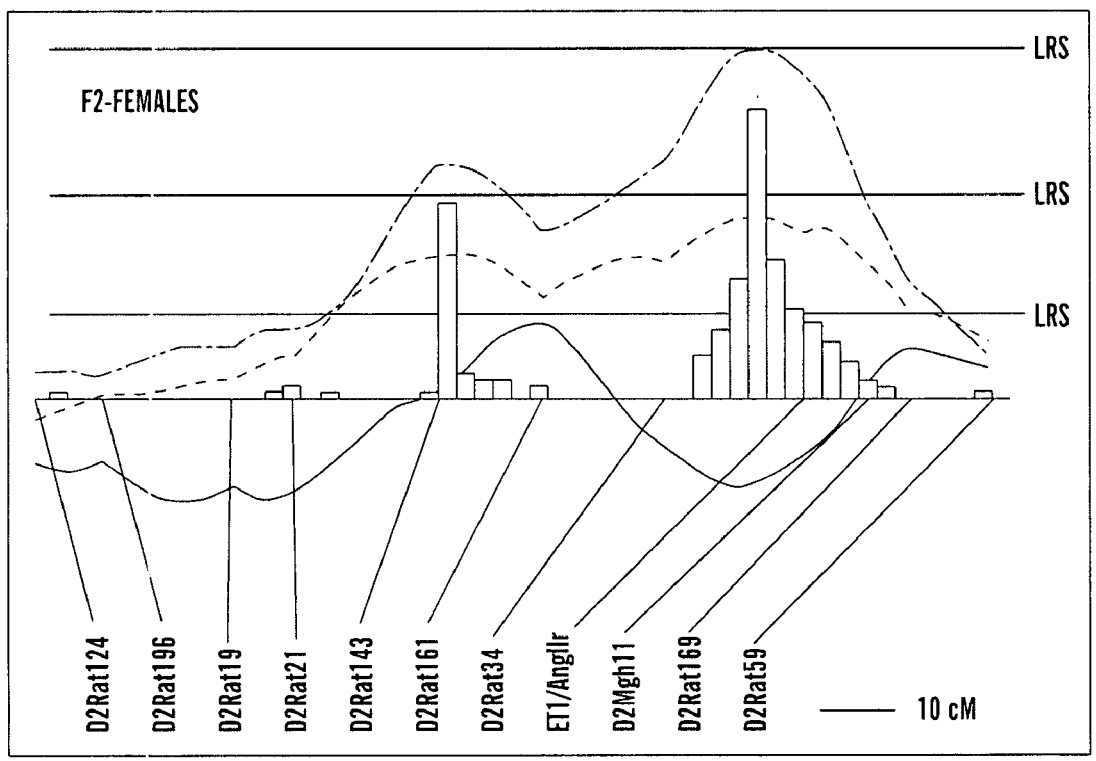

Having found functionally significant variants between Dahl S and Dahl R Dear genes, we then investigated the potential genetic contribution to hypertension susceptibility by performing independent QTL analysis on both male (n=106) and female (n=102) F2 [R×S]-intercross rats phenotyped for blood pressure by radiotelemetry after 8 and 12 weeks of high salt (8% NaCl) challenge respectively (Table 2). The high-salt diet challenge was extended 4 weeks longer for the F2 [R×S]-intercross female rats since female BP phenotype was much lower than in male F2 [R×S]-intercross rats (average F2 [R×S]-intercross male SBP after eight weeks of high salt diet=157.2±14.2 mmHg; average F2 [R×S]-intercross female SBP after twelve weeks of high salt diet=145.0±11.4 mmHg, Table 2). Using an SSCP-based Dear gene-specific marker (FIG. 4A), we mapped the rat Dear to chromosome 2 (physical position in the current assembly of the rat genome: 2q34, 176.687 Mb), 4.5 cM centromeric to the α1-Na, K-ATPase locus, ATP1A1. A total chromosome-2 scan was then done with 11 informative markers that distinguish Dahl R and Dahl S strains. Marker regression and interval mapping analyses detect a single chromosomal region with suggestive linkage to mean, systolic and diastolic BP, peaking at ATP1A1+2 cM (LOD=1.70) in the F2 [R×S] male cohort (FIG. 4B, Table 2). In contrast, chromosome-2 scan analysis of F2 [R×S]-intercross females revealed two QTLs on chromosome 2, one centered at D2Rat143 (LOD=2.43, significant linkage) and the other centered at Dear-5 cM (LOD=3.61, highly significant linkage) (FIG. 4C, Table 2). To assess pathophysiological relevance, analysis of Dear allele-specific contribution (Table 3) reveals that the Dahl S S44/M74 variant increases susceptibility to hypertension regardless of BP parameter—systolic, diastolic or mean arterial pressure with greatest changes in mean arterial pressure (ANOVA P<$10^{-3}$ to $10^{-4}$). Concordance of results in different blood pressure parameters provide evidence delineating the Dear locus as a gene for hypertension susceptibility in F2 [R×S]-intercross female rats.

To date, only Dear (shown here) and ATP1A1 (38, 43) genes exhibit functionally significant variants between Dahl S and Dahl R rats with demonstrated pathogenic relevance to hypertension. These data forward said two loci as candidate genes for the Dear-5 cM QTL region on chromosome 2 affecting BP in female F2 [R×S]-intercross rats based on a 4-parameter analysis framework for hypertension genes (37, 54). The causal role of ATP1A1 in hypertension has been shown by transgenesis in both male and female Dahl S rats (38). While putative gene interactions need to be investigated for Dear, ATP1A1-Na, K, 2Cl cotransporter (NKCC2) gene-interaction has been detected to increase susceptibility to high blood pressure in cosegregation analysis of F2 [R×S] intercross rats (39). This epistatic nature of the ATP1A1 effect on BP could account for the reduced statistical significance of linkage to BP detected at ATP1A1 when analyzed as a single locus as done in this chromosome 2 scan and in previous F2-intercross and congenic studies (34, 53).

To further analyze the Dear locus in the context of previous genetic rat model studies which report chromosome 2 QTLs for BP which span the Dear locus (31, 34, 41, 51, 59), we assessed Dear variants on WKY, SHR, BN and LEW rat strains used in said studies by SSCP analysis. As shown in FIG. 4A, the Dahl R Dear S44P/M74T variant is detected in Dahl R and LEW strains, while the Dahl S Dear S44/M74 variant is detected in SHR, WKY and BN strains. Detection of variant-specific alleles in the different strains was corroborated by direct nucleotide sequencing of two independent Dear cDNA clones spanning the entire amino acid coding region (data not shown). Since SHR, WKY and BN rat strains have the S44/M74 Dahl S Dear allele, the Dear locus is a priori eliminated as a candidate gene for the chromosome 2 QTL for BP in F2-intercross studies derived from these strains (31, 41, 51, 59). The Dear locus is also eliminated as candidate gene for the reported chromosome 2 BP QTL in F2 [Dahl S×LEW]-intercross study which investigated males only (34), since the Dear S-variant cosegregates with high blood pressure in females.

Thus, observations from genetic, molecular and pathophysiological analyses suggest that modification in the balance of AngII and ET-1 receptor systems through variant Dear contributes to hypertension susceptibility in female F2 [R×S]-intercross rats. The data reiterate the importance of gender-specific factors in hypertension susceptibility and the role of Dear in AngII-ET-1 response-balance.

Materials and Methods

Characterization of Dahl S and Dahl R Dear cDNAs

Dahl S and Dahl R Dear cDNAs were RT-PCR from Dahl S/JRHsd and Dahl R/JRHsd rat kidney PolyA+ RNAs respectively (Forward primer: 5'-AAG-AAA-GCA-GCA-CCT-TGG-T-3' (SEQ. ID. NO. 3); Reverse primer: 5'-CGT-GGA-CAG-AGA-CCT-TGT-CT-3' (SEQ. ID. NO. 4)) and subsequently subcloned into the PT-vector system (Clontech, Palo Alto, Calif.). Primer sequences were obtained from the previously reported Sprague Dawley Dear cDNA (GenBank accession number AY664492). The cDNAs (432 bp) encompassing the entire Dear amino acid coding region was then sequenced on both strands. Six Dahl S and six Dahl R rats were sequenced showing no intra-strain sequence heterogeneity.

Detection of the Dear Gene S44P/M74T Variant by Single Strand Conformation Polymorphism (SSCP) Analysis Dahl S/jrHsd, Dahl R/jrHsd, LEW/SsNHsd, WKY/NHsd, SHR/NHsd and BN/Hsd rats were purchased from Harlan Inc. (Indianapolis, Ind.). SSCP analysis was performed on genomic DNA isolated from the different rat strains essentially as described (60). The SSCP marker was based on a PCR product encompassing nucleotides 2774-2911 (spanning the S44P substitution) within the amino acid encoding region of the Dear cDNA (forward primer: 5'-GCT-ATG-TAT-CTG-GAC-AGC-AGC-3' (SEQ. ID. NO. 5); reverse primer: 5'-AGT-GAA-GCA-CAT-GAT-GCA-AGT-3'(SEQ. ID. NO. 6); product: 137 bp) (1). The SSCP marker was detected by 6% non-denaturing polyacrylamide gel electrophoresis.

Receptor Expression and Membrane Preparation

The Dahl S and Dahl R Dear cDNAs were subcloned directionally (5' to 3') into the pcDNA (+) expression vector (Invitrogen, Carlsbad, Calif.) and transiently expressed in Cos1 cells (ATCC). Cos1 cells were transfected with the expression vectors via lipofectin-mediated gene transfer and cell membranes were isolated 72 hr post-transfection for hormone binding. Rat kidney membranes were prepared essentially as described (42). COS-1 cell membranes were isolated as described (36). Briefly, cells were washed twice in phosphate-buffered saline and homogenized in 10-fold ice-cold buffer (0.25 M sucrose, 1 mM EDTA, 50 µg/ml aprotinin, 10 µg/ml leupeptin, 100 µM phenylmethylsulfonyl fluoride, 25 mM Imidazol/HCl, pH 7.4). The homogenate was centrifuged at 5,000 g for 15 min and the pellet was discarded. The supernatant was then centrifuged at 27,500 g for 30 min and the resulting pellet was washed twice in ice-cold suspension buffer (5 mM $MgCl_2$, 0.2 mM EDTA, 50 mM Hepes, pH 7.4). The final pellet was resuspended into the appropriate assay buffer and quickly frozen in liquid nitrogen. The membrane preparations were store at −80° C. until use. Protein concentrations of the membranes were determined by BCA protein assay kit (PIERCE).

Radioligand Binding Assays

Binding of [$^{125}$I]Tyr$^4$-angiotensin II and [$^{125}$I]Tyr$^{13}$-endothelin-1 to COS-1 membranes was performed by a rapid filtration method (32, 50). Briefly, [$^{125}$I]Tyr$^4$-angiotensin II (0.25~6.5 mM) or [$^{125}$I]Tyr$^{13}$-endothelin-1 (0.045~1.46 nM) was incubated with membranes (100 µg) for 20 min at 37° C. in 100 µl buffer A (5 mM $MgCl_2$, 0.2 mM EDTA, 10 mg/ml BSA, 10 mM Hepes, pH7.4). Binding reactions were terminated by the addition of 1 ml ice-cold buffer A and immediately filtered through a Whatman GF/C filter (presoaked overnight at 4° C. in 10 mg/ml BSA) and subsequently washed with 15 ml ice-cold buffer A. Specific binding was determined as the difference between the total radioactivity bound to membranes and the radioactivity bound to blanks containing 1 µM AngII or 1 µM ET-1. The dissociation constant ($K_d$) and maximum ligand-binding sites ($B_{max}$) were determined using Hill plot analysis (55). Hill coefficient values (h) were calculated from the relationship $\ln [B/(B_{max}-B)] = h \ln [\text{free Radioligand}] - \ln K_d$. An F test (P<0.05) was used to determine whether the saturation binding curves best fitted one or two independent binding sites. The data were best fit by two affinity states determined by Scatchard plot analysis; $K_H$ and $K_L$ designate the $K_d$ for high- and low-affinity states of the receptor, respectively (44). Most results are expressed as the mean±SE (standard error) from three to five independent experiments.

Western and West-Western Blotting Analysis

A polyclonal rabbit antipeptide antibody raised against the synthetic peptide $P_{51}$LLTSLGSKE$_{60}$ (SEQ. ID. NO. 7) was utilized for western blot analysis (1). Plasma membranes (40 µg protein/lane) were subjected to 12.5% SDS-PAGE and the separated proteins electro-transferred onto PVDF membranes which were incubated with blocking buffer (0.3% Tween-20, 5% non-fat milk, 137 mM NaCl, 2.7 mM KCl, 8.1 mM $Na_2HPO_4$, and 1.5 mM $KH_2PO_4$, pH7.4) for 2 hr at room temperature, and then incubated with primary antibody (1:500) for 16 hr at 4° C. The PVDF membranes were then sequentially incubated with biotinylated goat anti-rabbit IgG followed by immunostaining with horseradish peroxidase-linked streptavidin. To confirm the interaction between Dear and ligands, we performed west-western blot analysis (62). Briefly, protein blots of kidney and COS-1 cell membranes were incubated with radioligands (0.5 µCi in 10 ml) in buffer A at 37° C. for 16 hr. PVDF membranes were then washed three times for 15 min with buffer A at 37° C. and exposed to X-ray film at −80° C. for 1-3 days.

Genetic Crosses

Dahl S/jrHsd and Dahl R/jrHsd rat strains (Harlan, Indianapolis, Ind.) were used to develop the F2 cohort. The F2 cohort was derived from brother-to-sister mating of F1 (R female×S male) hybrids to produce the F2 male (n=106, carrying exclusively Y chromosomes from the Dahl S genetic background) and F2 female (n=102) segregating populations.

Phenotypic Characterization of F2 Cohorts

All animal procedures were performed in accordance with institutional guidelines. Animals were maintained on a Lab-Diet 5001 rodent chow (Harlan Teklad, Madison Wis.) containing 0.4% NaCl from weaning until the high salt diet begun at 12 weeks of age. The food pellets and water were made available ad lib. Blood pressure (BP) was measured essentially as described (38) using intra-aortic abdominal radiotelemetric implants (DATASCIENCE) obtaining non-stressed blood pressure measurements taking the average over ten-seconds every 5 minutes for 24 hours (38). Systolic (SBP), diastolic (DBP) and mean arterial pressures (MAP) were obtained along with heart rate and activity. The protocol for the F2 rats was as follows: implant surgery at 10 weeks of age; only rats with no post-operative complications were used; after 12 days, baseline BP levels were obtained. High salt (8% NaCl) challenge was begun at 12 weeks of age and maintained for eight weeks for male and twelve weeks for female F2-intercross rats; a longer high-salt challenge was necessary for females to attain a similar F2-mean BP since BP in females is lower. BP values used for phenotype are the averages obtained in the final week of the salt loading from a 24-hour recording during a no-entry day ascertaining non-stress BP. We note that baseline BP means for SBP, DBP and MAP were equivalent, ±1 mmHg range for all three BP parameters among the different Dear genotypes (P>0.5).

Intercross Linkage Analysis

Genotyping was done with 10 chromosome-2 microsatellite markers informative for our Dahl [R×S] intercross and one SSCP-based Dear marker (described above). Marker regression and QTL analyses was performed with the Map Manager QTXb17 (MMQTXb17) program (46) using MAP as quantitative trait. MMQTXb 17 generates a likelihood ratio statistic (LRS) as a measure of the significance of a possible QTL. Genetic distances were calculated using Kosambi mapping function (genetic distances are expressed in cM). Critical significance values (LRS values) for linkage were determined by a permutation test (2000 permutations at 10 cM interval) on our male and female progenies using Kosambi mapping function and a free regression model. Thus, the minimum LRS values for the F2 male cohort were for Suggestive linkage=4.1 (LOD=0.89); for Significant linkage=10.6 (LOD=2.30); for Highly Significant linkage=18.4 (LOD=4.00) and for the F2 female cohort were for Suggestive linkage=3.9 (LOD=0.85); for Significant linkage=9.9 (LOD=2.15); for Highly Significant linkage=16.6 (LOD=3.61). LRS 4.6 delineates LOD 1-support interval. Confidence interval for a QTL location was estimated by bootstrap resampling method wherein histogram single peak delineates the QTL and peak widths define confidence interval for the QTL. Histograms which show more than one peak warn that the position for the QTL is not well defined or that there may be multiple linked QTLs (QTX Map Manager) (46).

EXAMPLE 2

Figure 5A:
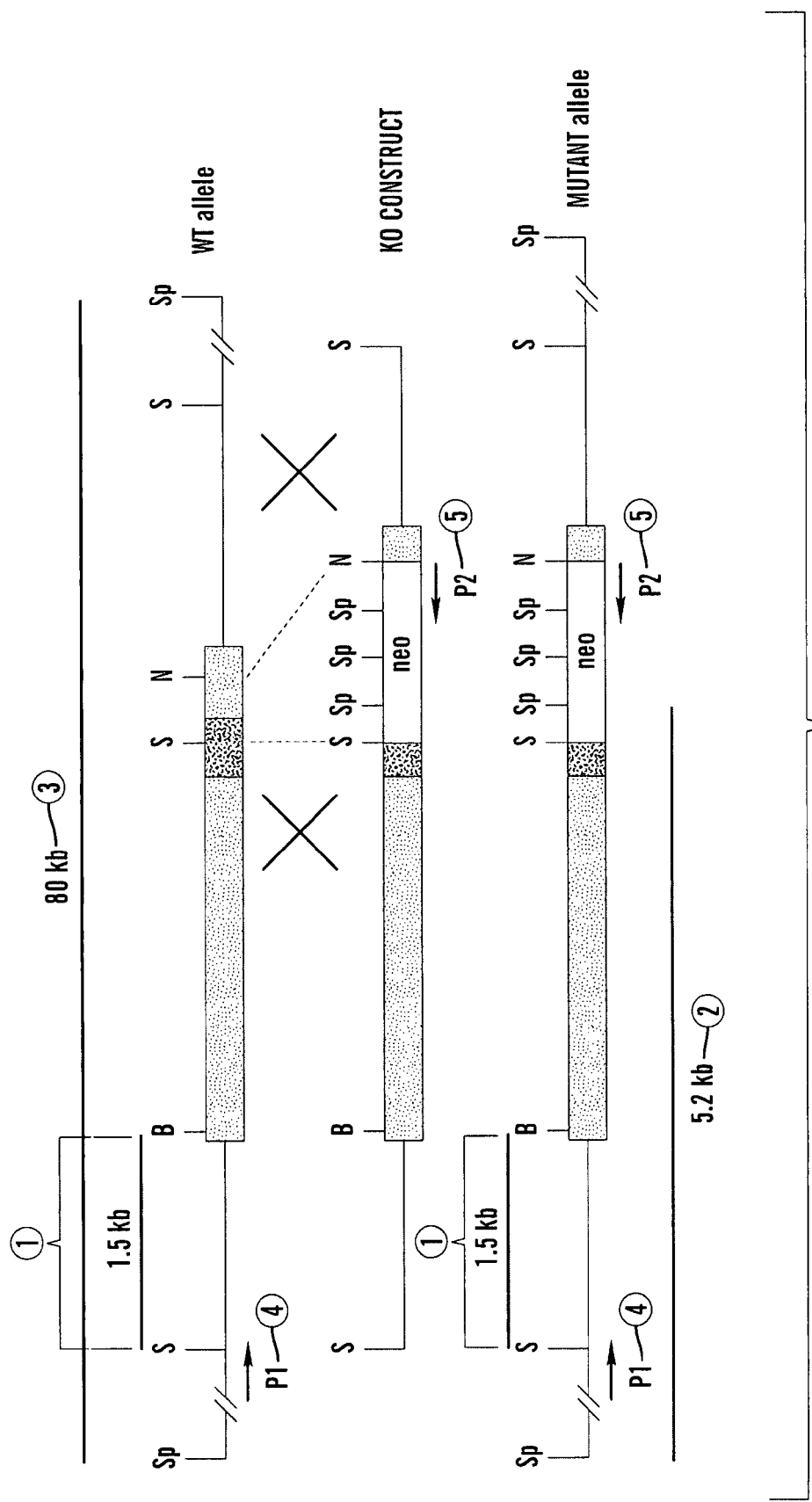
FIG. 5A shows a restriction map of wild type 129SVJ mouse Dear (WT allele), the Dear targeting vector for homologous recombination (KO construct), and the mutant allele. (1) is a probe for Southern-blot analysis, which is a 1.5 kb S-B restriction fragment which detects a 5.2 kb SphI restriction digest fragment in targeted allele (2) and a 8.0 kb fragment in the wild type allele (3); P1 (4) is a forward primer flanking integration site; P2 (5) is a reverse pGKNeo-specific primer; successful targeting event yields expected 5.5 kb P1-P2 PCR product. S, SacI; B, BamHI; N, NsiI restriction enzymes.
Figure 5B:
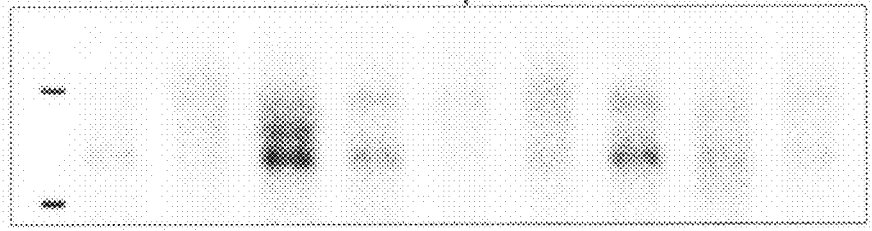
FIG. 5B shows a Northern blot analysis which detects mouse Dear mRNA in all tissues tested with higher levels in kidney and aorta. The three different-sized Dear mRNAs most likely represent different polyadenylation signals. 28S and 18S ribosomal markers are noted to the left. H, heart, B, brain, K, kidney, Li, liver, Sp, spleen, Lu, lung, Ao, aorta, Te, testis, Ut, uterus.

We isolated the mouse Dear gene from a 129 SVJ mouse genomic library. Molecular characterization detects a one-exon transcription unit (FIG. 5A). The mouse receptor polypeptide contains 127 amino acids showing 78 percent homology with the rat receptor and binds solely ET-1 (data not shown) resembling the recently characterized Dahl R Dear S44P/M74T rat variant (2), and suggesting that observations in Dear$^{-/-}$ mice are most likely not AngII-mediated. The mouse Dear mRNA is detected in all tissues tested with the highest level of expression in kidney and aorta (FIG. 5B).

Figure 5C:
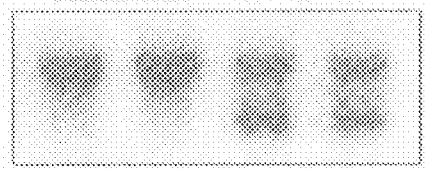
FIG. 5C shows a Southern blot analysis for detection of Dear-inactivation in mice by homologous recombination. Evidence of inactivation is characterized by predicted 5.2 kb SphI restriction digest fragment of genomic DNA detected as a lower hybridizing band in heterozygous (+/−) DNA samples compared with absence in wild type (+/+) samples.
Figure 5D:
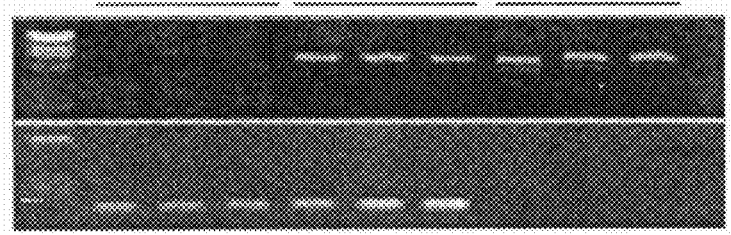
FIG. 5D shows PCR genotyping of E11.5 mouse embryos. Results (lower panel) show a 153 bp allele in wild type, Dear$^{+/+}$ (+/+) and heterozygous Dear$^{+/-}$ (+/−), but not in Dear$^{-/-}$ (−/−) embryos. The upper panel shows inactivated (5.5 kb) allele in Dear$^{+/-}$ and Dear$^{-/-}$ but not in Dear$^{+/+}$ embryos.

Targeted inactivation of Dear$^{-/-}$ in ES cells was done by replacement of the genomic region spanning amino acids 81-127 of Dear with a PGK-neomycin cassette (FIG. 5A) resulting in the deletion of the last 47 amino acids of the Dear polypeptide, including the putative G-protein interacting domain (1). Screening for homologous recombination was done on 196 G418-resistant colonies by Southern blot analysis (FIG. 5C). Targeting events were confirmed by polymerase chain reaction (PCR) amplification using a neomycin-specific primer and a primer flanking the integration site. Production of the expected size fragment (5.5 Kb) was indicative of a targeting event (FIG. 5D). Five ES cell clones carrying the targeted Dear mutation were injected into 129SVJ blastocysts and implanted into pseudopregnant foster mothers. We obtained 14 chimeric mice (representative of 2 independent targeted ES cell clones). Chimeras were bred to C57BL/6J mice and shown to germ line transmit, producing F1 progeny.

Figure 5F:
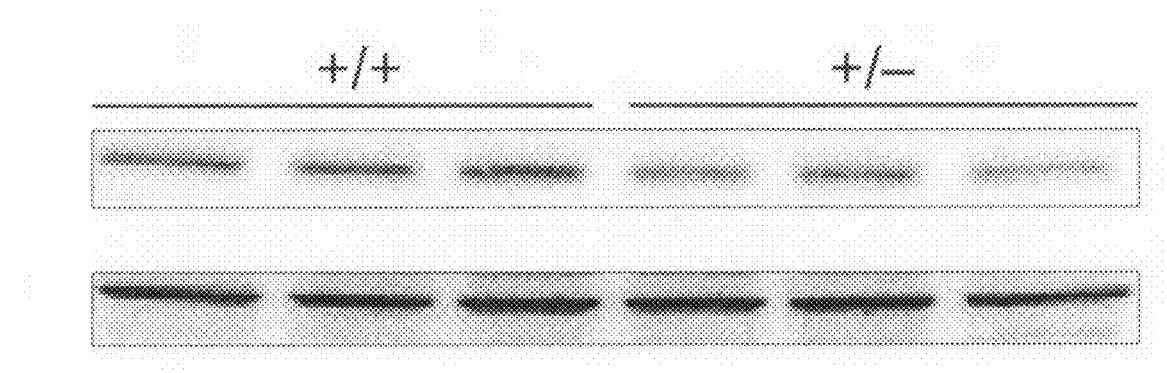
FIG. 5F: Western blot analysis of Dear$^{+/+}$ (+/+) and Dear$^{+/-}$ (+/−) deficient mouse kidney membranes using the anti-mouse Dear specific anti-peptide antibody (upper panel); presence of a non-specific cross-reacting high molecular weight protein demonstrates equal amounts of protein analyzed (lower panel).
Figure 5H:
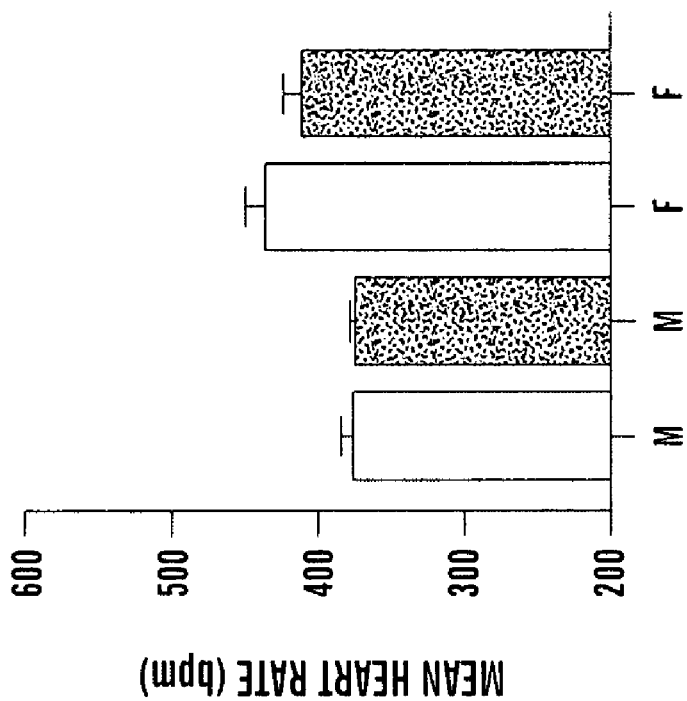
FIGS. 5G-5I: Analysis of blood pressure (FIG. 5G), heart rate (FIG. 5H) and body weight (FIG. 5I) in heterozygous Dear$^{+/-}$ adult mice. Systolic blood pressure (SBP, mmHg) and mean heart rate (bpm, in beats per minute) in Dear$^{+/+}$ (□) and Dear$^{+/-}$ (■) deficient male (M) and female (F) mice. Body weight in grams (g) comparing male Dear$^{+/+}$ (◇) and Dear$^{+/-}$ (◆) mice, and female Dear$^{+/+}$ (○) and Dear$^{-/-}$ (●) mice from 4-6 months (m) of age. *, P<0.05; **, P<0.01.
Figure 5G:
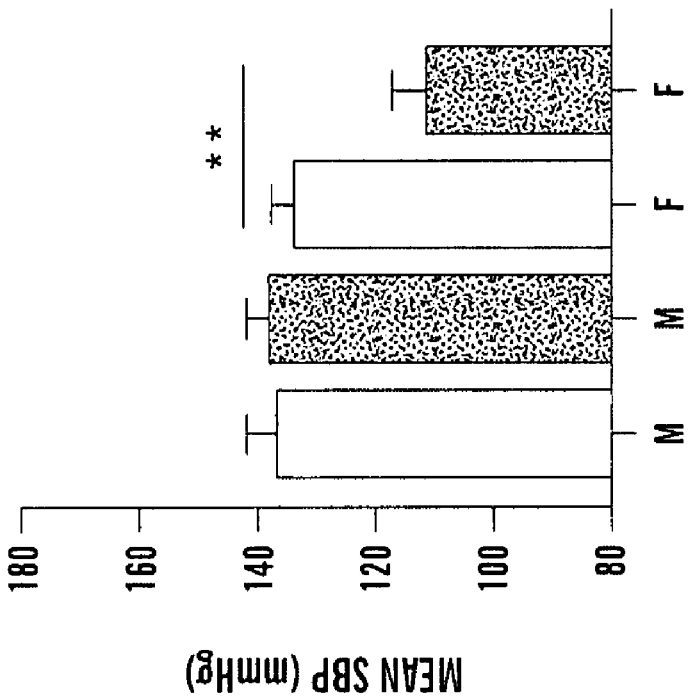
Figure 5I:
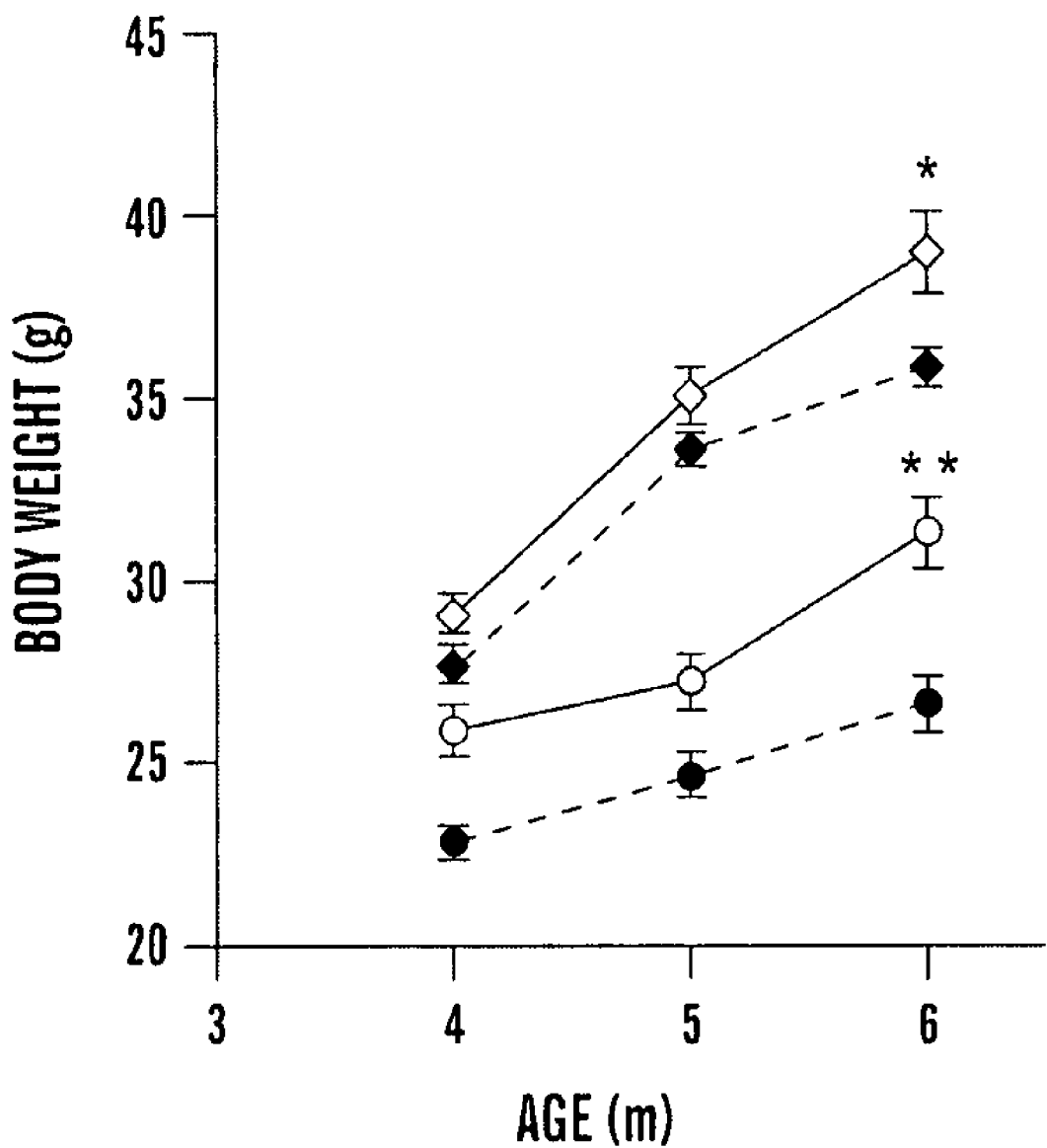

Heterozygous Dear-deficient (Dear$^{+/-}$) male and female mice (backcross-10 inbred C57BL/6 mouse strain) exhibit 50% less Dear protein in mouse kidney protein blot analysis as detected using an anti-mouse Dear anti-peptide specific antibody (FIG. 5F; P<0.05, t-test), less body weight at 5 and 6 months of age (males: P=0.007; females: P=0.0006) (FIG. 5I) and decreased blood pressure in female (Dear$^{+/+}$: 134±4.0 mmHg vs Dear$^{+/-}$: 11 2.3±6.1; P<0.01) but not in male mice while heart rate remains equivalent (FIG. 5G-H). Gender-specific blood pressure effects are concordant with observations in a recent study of rat genetic hypertension wherein Dear variants cosegregated with hypertension in female but not in male F2-intercross rats (2).

To assess potential embryonic lethality of the gene-targeting event, we analyzed progeny from F1-Dear$^{+/-}$ male and female cross which were genotyped for the presence/absence of the targeted Dear allele. Sixty-eight pups were produced from 17 liters showing the following genotype distribution: 29 wild type (+/+), 39 heterozygous (+/−), 0 null (−/−). The absence of null genotypes in the F2 progeny demonstrates that Dear null mutation is embryonic lethal.

In order to investigate embryonic lethality in Dear$^{-/-}$ embryos, we analyzed embryos from timed-pregnancies derived from Dear$^{+/-}$ mice at different stages of development to determine the exact developmental stage in which lethality occurs. We produced 129 embryos (from E9.5 to E12.5) detecting 33 (−/−), 67 (+/−) and 29 wildtype (+/+) genotypes (FIG. 5D). This conforms to the expected segregation ratio 1 (+/+):2 (+/−):1 (−/−) for a standard (+/−)×(+/−) intercross. Analysis of the embryos revealed that lethality occurs around E12.5.

Figures 6A, 6B, 6C:
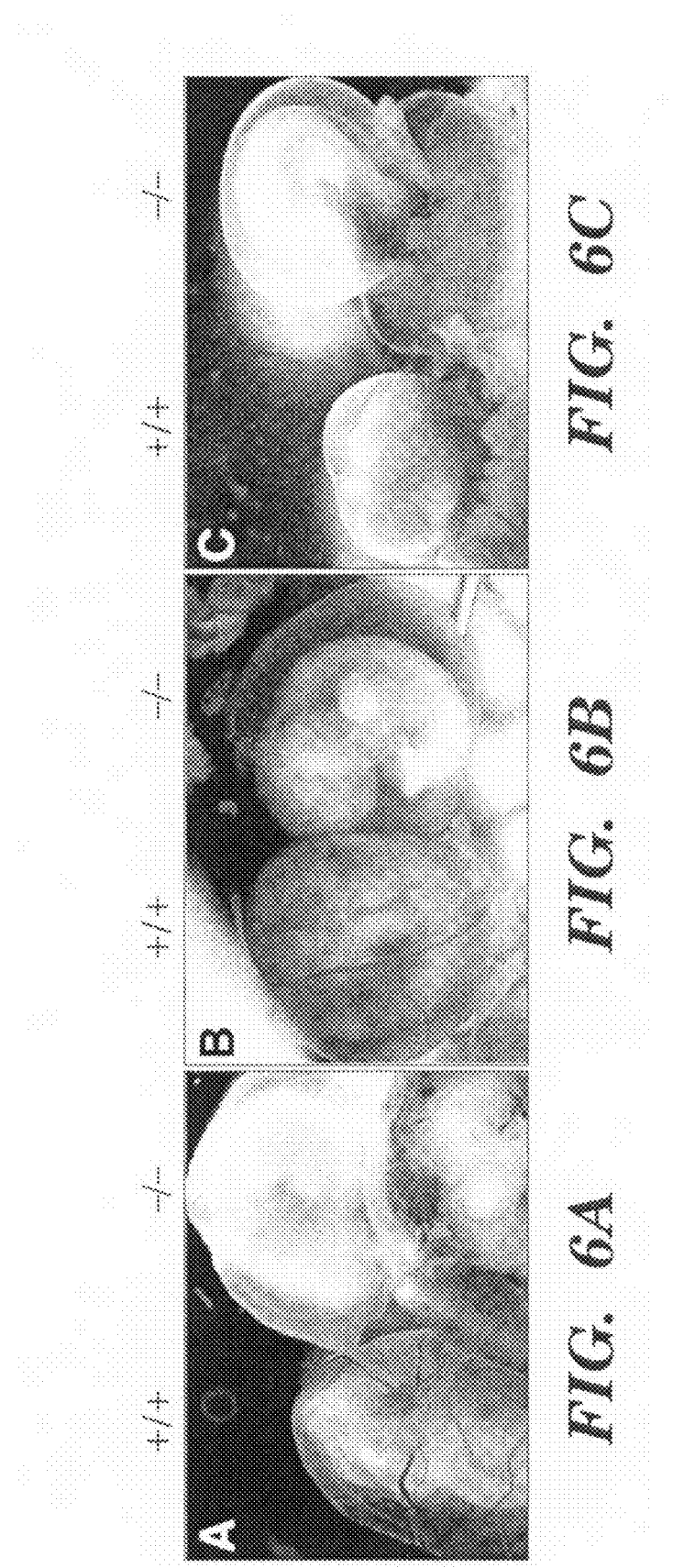
Figures 6D, 6E, 6F:
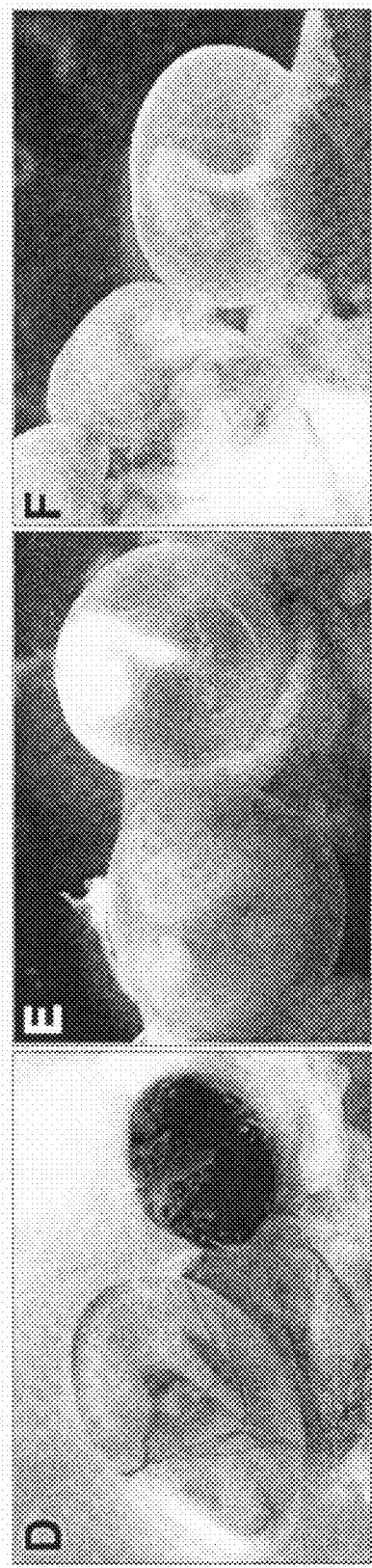

Anatomic analysis of E9.5-E12.5 embryos reveals absent yolk-sac collecting vessels associated with homozygous Dear$^{-/-}$-deficiency (FIG. 6A-F); heterozygous Dear$^{+/-}$ deficient embryos exhibit normal yolk sac vascularization (data not shown). All embryos with absent yolk-sac collecting vessels are Dear$^{-/-}$ by genotype; heterozygous Dear$^{+/-}$ deficient embryos are not distinguishable from Dear$^{+/+}$ embryos (data not shown). Hemorrhagic, resorbed embryos were detected as early as E10.5 but mostly at E12.5 (FIG. 6D). Although smaller and strikingly paler than Dear$^{+/+}$ and Dear$^{+/-}$ embryos, Dear$^{-/-}$ embryos exhibit two size phenotypes: a dysmorphic phenotype detected at E10.5-E12.5 (FIG. 6A-C) that is relatively larger than a second, hypoplastic phenotype (FIG. 6E-F). In order to determine whether genetic variation influences the null phenotype, speed congenics were done onto C57BL/6j genetic background and backcross-10 null mice were generated and analyzed confirming embryonic range of lethality, absent yolk-sac collecting vessels and both embryo morphology phenotypes in Dear$^{-/-}$ embryos (FIG. 6A-F).

At E10.5 and E11.5, blood-filled pumping hearts were detected in larger dysmorphic Dear$^{-/-}$ mice (FIG. 6B, 6C), but not apparent in hypoplastic Dear$^{-/-}$ mice (FIG. 6E, F). Dear$^{-/-}$ E10.5 embryos lack the vascular network formation marked by prominent blood-filled dorsal aortae (FIG. 6G) and blood vessels in the cranial region which are normal features characteristic of E9.5 Dear$^{+/+}$ embryo (FIG. 6G left panel). Furthermore, E10.5 Dear$^{-/-}$ embryos exhibit disorganized, blood-filled pools in the cranial region without apparent connection to a blood-filled heart (FIG. 6G) observed to pump (data not shown) despite lack of vascular networking. In contrast to E11.5 Dear$^{+/+}$ embryo, E11.5 dysmorphic-type Dear$^{-/-}$ embryo exhibits minimal and altered vascular networks in both cranial and caudal regions, dilated heart albeit blood-filled, and altered brain development (FIG. 6H). Furthermore, while both Dear$^{-/-}$ and Dear$^{+/+}$ E11.5 hearts pump, observation of cardiac pumping reveals single chamber filling and contraction in Dear$^{-/-}$ embryos, in contrast to distinct filling and pumping of ventricles in E11.5 Dear$^{+/+}$ embryo (data not shown). In E10.5 and E11.5 hypoplastic Dear$^{-/-}$ embryos, minimal cardiovascular development is detected (FIG. 6E-F). Altered brain and cardiac development is confirmed in the analysis of cleared, fixed E11.5 embryos revealing poor delineation of brain regions particularly the telencephalon and cardiac chamber formation (FIG. 6I).

In summary, analysis of dysmorphic Dear$^{-/-}$ embryos at E10.5 and E11.5 detects blood-filled hearts (FIG. 6G-H) which contracted, despite aberrant vascular formation typified by disorganized, blood-filled pools in the cranial region without apparent connection to a blood-filled heart (FIG. 6G), or minimal vascular networks in both cranial and caudal regions, and a dilated blood-filled heart (FIG. 6H). This contrasts the prominent vascular network marked by blood-filled dorsal aorta and blood vessels in the cranial region which are characteristic features of E9.5 Dear$^{+/+}$ embryo (FIG. 6G).

Furthermore, analysis of fixed E11.5 embryos reveals abnormal brain and cardiac development in Dear$^{-/-}$ embryos (FIG. 6I).

Figure 7A:
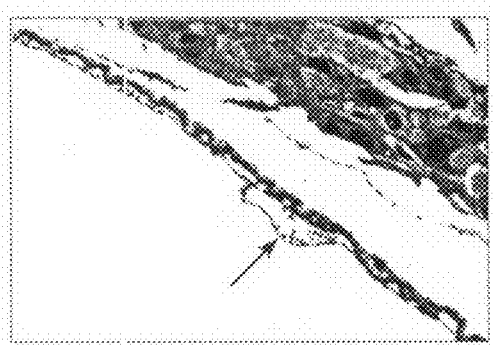
FIGS. 7A-7L shows histologic analysis of Masson-trichrome stained mouse embryos.
Figure 7B:
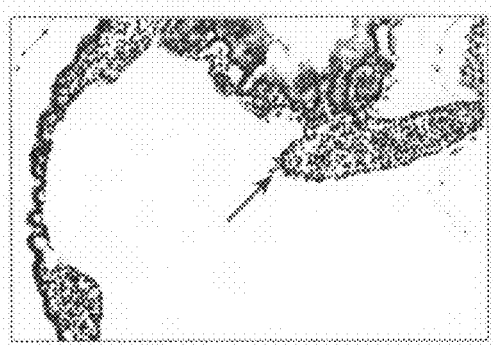
Figure 7C:
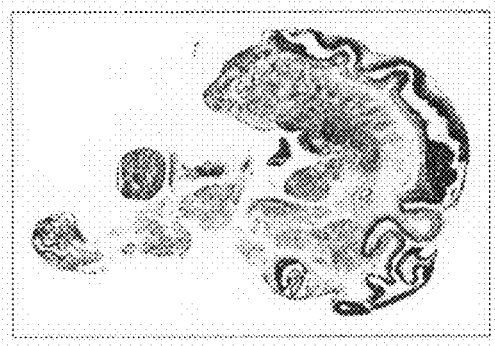
Figure 7D:
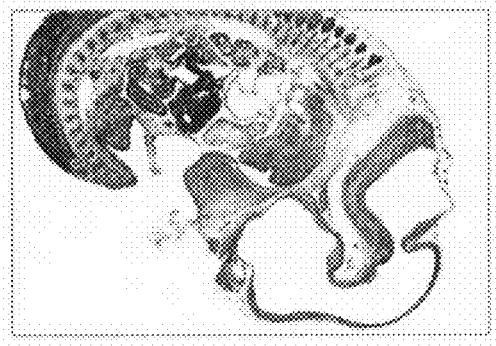
Figure 7E:
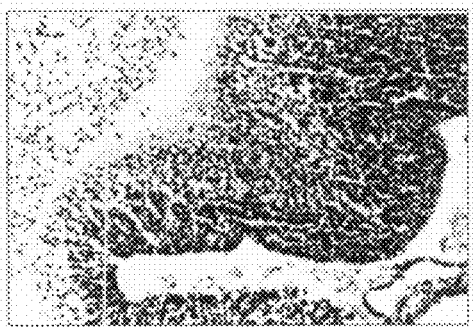
Figure 7F:
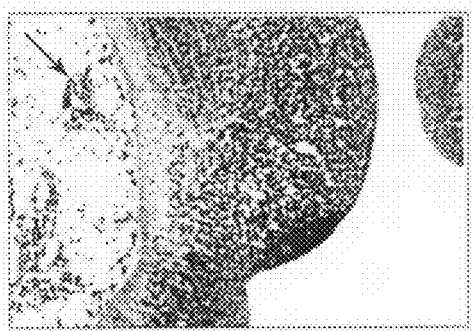
Figure 7G:
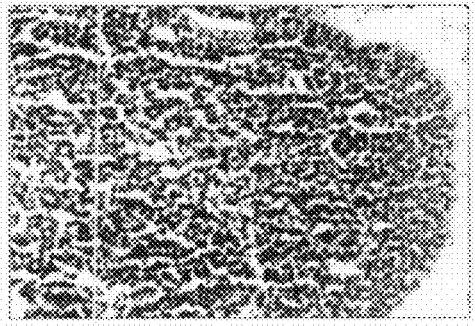
Figure 7H:
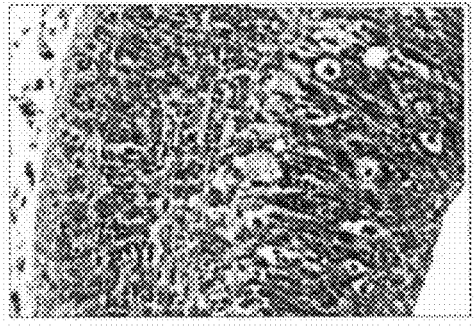
Figure 7I:
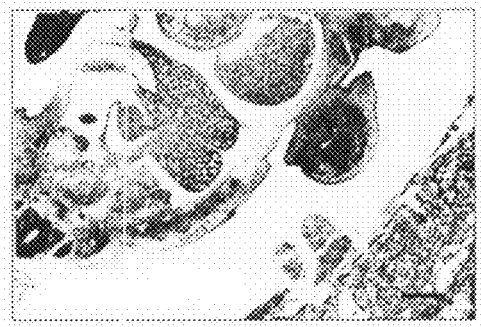
Figure 7J:
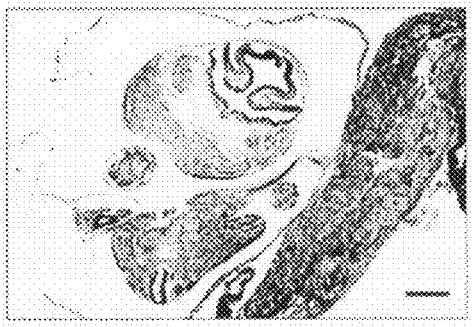
Figure 7K:
Figure 7L:
Figure 8A:
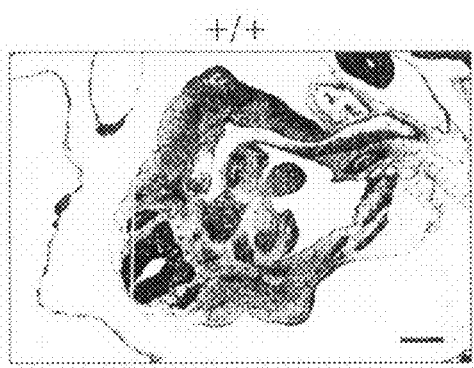
FIGS. 8A-F: Histological analysis of Dear$^{+/+}$ (+/+) (FIGS. 8A, 8C and 8E) and Dear$^{-/-}$ (−/−) mouse embryos (FIGS. 8B, 8D and 8F). Masson-trichrome stained E11.5 embryos showing deficient development of dorsal aorta (da), vasculature (vasc) and yolk sac, as well as heart and brain in Dear$^{-/-}$ (bar=160 µm).
Figure 8B:
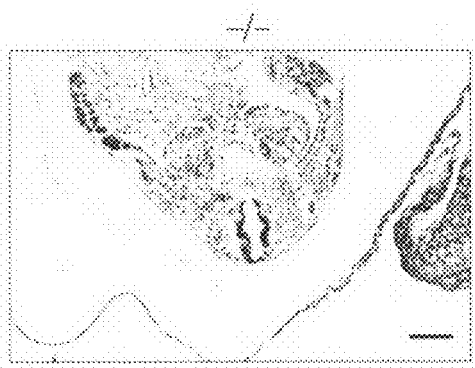
Figure 8C:
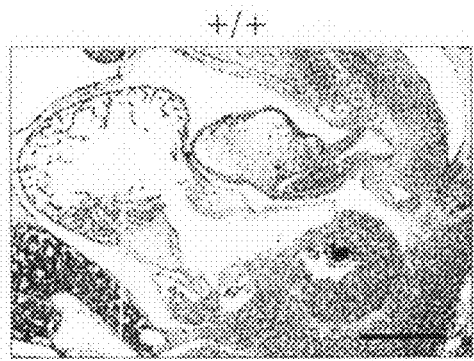
Figure 8D:
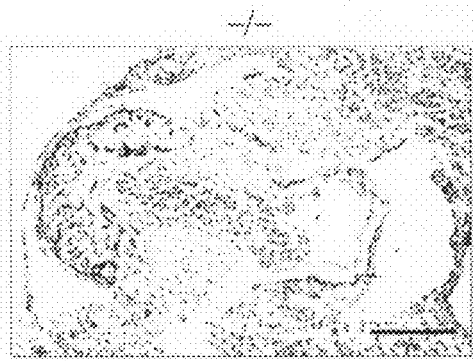
Figure 8E:
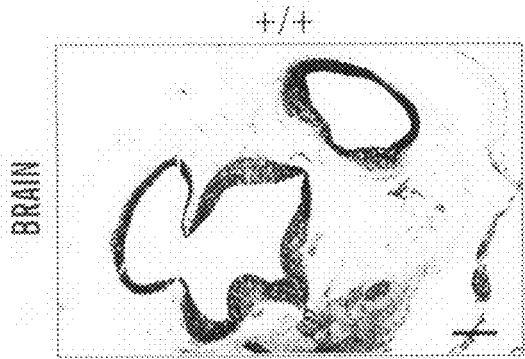
Figure 8F:
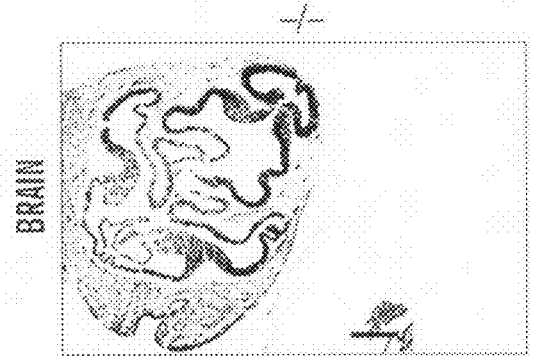
Figure 9A:
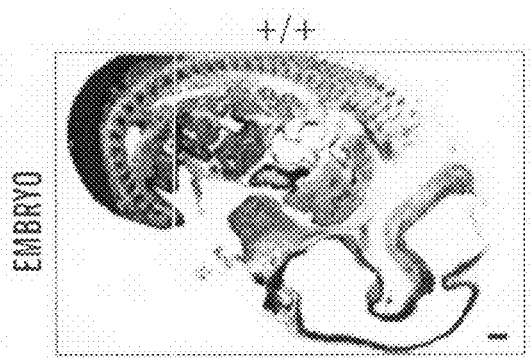
FIGS. 9A-F: Smooth muscle cell α-actin immunostaining of E12.5 mouse embryos (embryo (FIG. 9A-B); bar=160 µm) demarcating angiogenesis (angiog.
Figure 9B:
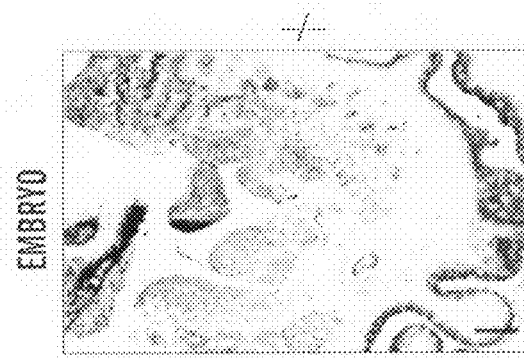
Figure 9C:
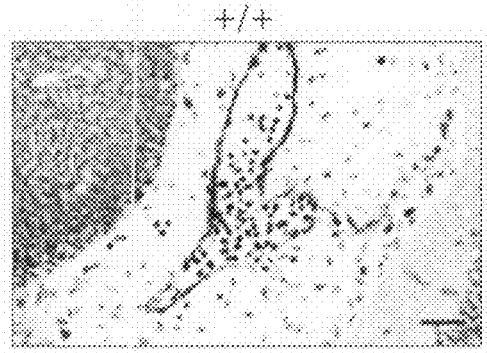
Figure 9D:
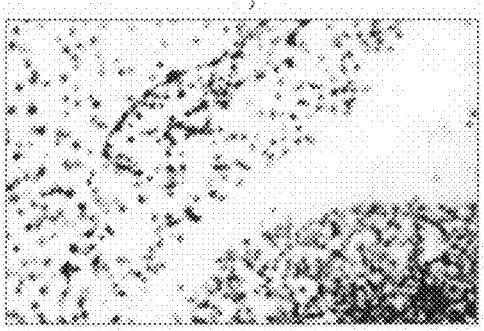
Figure 9E:
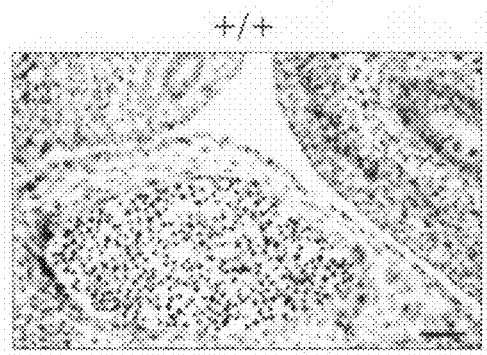
Figure 9F:
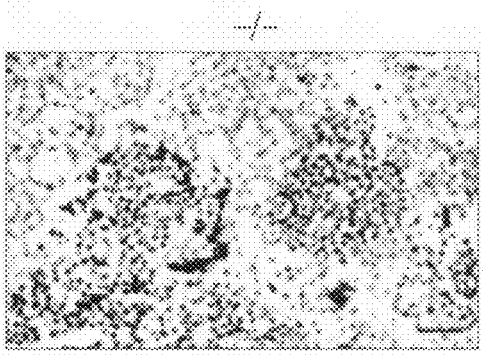

Histological analysis of Masson-trichrome stained E10.5-E11.5 embryo sections confirm minimal to absent collecting vessels in the yolk sac in Dear$^{-/-}$ embryos (FIG. 7A) compared with Dear$^{+/+}$ (FIG. 7B) at E10.5. The yolk-sac plexus of smaller vessels are present, with fewer nucleated red blood cells (FIG. 7A). A few are enlarged (FIG. 7A). Blood islands are present but the number of nucleated red blood cells is decreased in Dear$^{-/-}$ embryos (FIG. 7A) compared with Dear$^{+/+}$ embryos (FIG. 7B). At E12.5, comparative histological analysis reveals amorphous cellular areas with a lack of apparent organogenesis in dysmorphic-type Dear$^{-/-}$ embryos (FIG. 7C) compared with Dear$^{+/+}$ (FIG. 7D). High magnification reveals large areas of nucleated red blood cells in the ventral midportion that are not contained in blood vessels or in recognizable liver tissue (FIG. 7C). The heart is thin-walled, enlarged and with poor delineation of chambers in Dear$^{-/-}$ embryos (data not shown) corroborating anatomical observations (FIG. 6). Blood vessels with few nucleated red blood cells are rudimentary, thin-walled and sparse in Dear$^{-/-}$ (FIG. 7C) compared with Dear$^{+/+}$ (FIG. 7D) embryos most evident in the cranial region. Rudimentary, thin-walled blood vessels are detected in the perineural regions with sparse nucleated rbcs in Dear$^{-/-}$ (FIG. 7E), in contrast to Dear$^{+/+}$ embryos which exhibit perineural blood vessels filled with nucleated rbcs and with perivascular sheaths (FIG. 7D, F), thus corroborating the observed vascular network deficiency evident in anatomical analyses (FIG. 6). Concordant with sparse perineural vessels, only a few penetrating capillaries are evident in Dear$^{-/-}$ embryo neuroepithelium (FIG. 7G) in contrast to Dear$^{+/+}$ embryo (FIG. 7H). Scattered nucleated rbcs are detected in the neuroepithelium (FIG. 7G) suggesting possible vascular leakiness and/or failure of vasculogenesis. Immunohistochemical analyses comparing E12.5 Dear$^{+/+}$ and Dear$^{-/-}$ embryos do not detect upregulation of VEGF, VEGF-receptor 2 flk-1, or angiopoietin-1 and -2 expression (data not shown).

To further analyze vascular deficits, immunohistochemical staining for smooth muscle cell (smc) α-actin reveals scattered expression in E12.5 Dear$^{-/-}$ embryos and intense staining in the embryo-placenta vascular connection (FIG. 9A-F). Perineural blood vessels exhibit α-actin immunostaining in Dear$^{-/-}$ embryos but have minimal angiogenic-branching in contrast to Dear$^{+/+}$ embryos wherein angiogenic sprouting is evident (FIG. 9A-F). Closer histological analysis reveals sporadic blood islands incompletely circumscribed by α-actin stained single-cell vascular wall in Dear$^{-/-}$ embryos (FIG. 9A-F).

Figure 10A:
FIGS. 10A and 10B: Analysis of mouse dear expression pattern in wild type (+/+) E9.5 and E12.5 embryos detects Dear expression in the heart, extra-embryonic and embryonic vasculature, and neural tube. sc, spinal cord, ao, aorta, bi, blood islands; neuroepith, neuroepithelium; bar=20 µm.
Figure 10B:

To investigate mouse Dear temporal and spatial expression patterns, we analyzed Dear expression in E9.5-E12.5 wild type embryos using an anti-mouse Dear specific anti-peptide antibody validated to detect Dear polypeptide (FIG. 10). At E9.5 days, we detect Dear expression predominantly in the heart, yolk sac mesodermal layer and endothelium, fetal vascular endothelium in the placenta, dorsal aorta, and ependymal layer of the neural tube (FIG. 10A). These expression patterns persist at E12.5 days, wherein we detect increased expression in some hemangioblasts in yolk sac blood islands (FIG. 10B), as well as more prominent expression in the ependymal layer of the neuroepithelium and in perineural blood vessel walls (FIG. 10B). Observed temporal and spatial expression patterns are concordant with vascular, cardiac and neuroepithelial phenotypes observed in Dear$^{-/-}$ deficient mice.

In contrast to minimal blood islands in the yolk sac, we detect scattered blood islands in Dear$^{-/-}$ embryos but markedly underdeveloped dorsal aorta and peripheral vasculature, suggesting deficiencies in primary vascularization despite the presence of blood islands (FIG. 8A-F). Analysis of cardiac development in adjacent littermates reveals that Dear$^{-/-}$ hearts have poor cardiac chamber formation and endocardial cushion formation (FIG. 8A-F), consistent with incomplete cardiac looping observed on analysis of whole embryos (FIG. 6).

The Dear$^{-/-}$ mutant vascular and cardiac phenotypes in the C57BL/6J genetic background (BC10) is similar to that observed in VEGF$^{+/-}$ deficient embryos (18, 19), but quite distinct from that observed in previously reported ET-1, ET$_A$ and ET$_B$ receptor null embryos (10-12, 24), as well as AngII, AT1a, AT1b, and AT2 receptor null mutants (14-17). The similarity to VEGF$^{+/-}$ deficient mouse vascular phenotype (18, 19) suggests that both VEGF and Dear-mediated signaling are necessary for angiogenesis and vascular network development, as well as modulate blood island formation. The fact that both VEGF and Dear null mutations are embryonic lethal, along with other similar vascular-phenotype null mutants such as transforming growth factor-β1 (25), suggest that multiple pathways are involved in vascular network formation—all necessary but none sufficient. The slightly later but overlapping range of embryonic lethality indicates that Dear-mediated pathways are downstream to VEGF-mediated pathways. The association of vascular network deficiency and arrest of cardiac development in both VEGF$^{+/-}$ and Dear$^{-/-}$ deficiency suggests that vascular-derived signaling plays a role in the progression of the complex development of the heart into a multi-chambered pump. The finding that Dear$^{-/-}$ deficiency results in embryonic lethal vascular network abnormalities, while ET-1$^{-/-}$ inactivation does not interfere with vascular networking (10) implies the existence of an alternative ET-1 source that is produced independently of the well known Pre-pro-ET-1 pathway (26) or alternatively, the existence of an [ET-1]-like ligand that activates Dear and underlies Dear-mediated angiogenic roles.

Methods

Northern Blot Analysis

Total RNA was extracted with TRIzol (Invitrogen, Life Technologies Inc.,) from the different tissues analyzed. PolyA$^+$ RNA was subsequently isolated from total RNA using the Dynabeads mRNA purification kit (Dynal Biotech) as per manufacturer's specifications. PolyA$^+$ RNA (3 µg) was run on a 1% formaldehyde-denaturing agarose gel, transferred to Zeta-Probe blotting membrane (Bio-Rad) and UV cross-linked prior to hybridization. Hybridization was done in a buffer containing 5×SSC, 20 mM Na$_2$HPO4, 7% SDS, 1×Denhardt's, 100 ug/ml denatured Calf thymus DNA at 50° C. for 24 h. A γ-$^{32}$P-end labeled anti-sense mouse Dear oligonucleotide (5'-AGT-GAT-AGA-GCC-CCA-GTT-CCA-GCG-AGA-CTT-CAT-CTC-CTT-GC-3' (SEQ. ID. NO. 8)) was used as probe. Membranes were washed sequentially with 3×SSC, 5% SDS at 50° C. two times for 30 minutes each, and once with 1×SSC, 1% SDS at 50° C. for 30 min. Autoradiography was carried out at −80° C. with intensifying screen.

Characterization of 129SVJ Mouse Dear Gene

One million independent recombinants from a λFIXII 129SVJ mouse genomic library were screened with the full-length 3274 bp rat Dear cDNA[1] as probe. Six independent genomic clones were identified and plaque-purified after a fourth round of screening. One of them, λ191, was characterized further by restriction digestion and subsequent southern blot analysis. A single 8 kb BamHI/BamHI restriction fragment (that hybridized to the 3274 bp rat Dear cDNA probe) was subcloned into psp73 plasmid vector and sequenced.

Targeted disruption of Dear in mice and production of chimeric mice

All animal procedures were performed in accordance with institutional guidelines. A targeting vector was constructed by replacing a 300-bp piece containing the 3'-end of Dear with the PGKNeo-cassette (FIG. 5) effectively deleting amino acids 81-127 of Dear. The targeting vector was electroporated into 129SVJ ES cells and G418 resistant cell clones were isolated. Genomic DNA was obtained from each ES cell clone, restricted with SphI and subjected to Southern blot analysis. A 1.5 Kb fragment of Dear was used as probe (FIG. 5). The presence of an 8 Kb endogenous band and a 5.2 Kb band was indicative of homologous recombination (FIG. 5). Homologous recombination was further verified by PCR analysis using an upstream primer (P1: 5'-TGTGAGGCTA-GAAGGCTGC-3' (SEQ. ID. NO. 9)) located 171 bp upstream from the 5'-end of the targeting vector and a reverse primer (P2: 5'-GAGCAAGGTGAGATGACAGG-3' (SEQ. ID. NO. 10)) located in the PGKNeo cassette (FIG. 5). Amplification of a 5.5 Kb fragment that hybridized to the same probe used in the Southern blot analysis (FIG. 5) was indicative of homologous recombination. Five positive ES cell clones were then microinjected into 129SVJ blastocysts generating 14 chimeric mice that were used to establish the Dear knockout line. Speed-congenic backcross breeding to inbreed onto C57BL/6 genetic background was done for more than ten generations, <BC10, providing all Dear+/and Dear$^{-/-}$ mice for analyses (>99.95% congenic line in C57BL/6 background).

Characterization of Mouse Dear cDNA and Expression Studies

Mouse Dear cDNA was obtained by RT-PCR from C57BL/6 mouse kidney PolyA$^+$ RNA (forward primer, 5'-CACACAAAGCCTTACTTTATCC-3' (SEQ. ID. NO. 13); reverse primer, 5'-AAAGCCAGCCTTTAGATAACC-3' (SEQ. ID. NO. 14)), subcloned into the PT-vector system (Clontech, Palo Alto, Calif.) and then sequenced (GenBank accession no. DQ009865). RNA blot analysis was done as described (1) using PolyA$^+$ RNA (3 µg), γ-$^{32}$P end labeled anti-sense mouse Dear oligonucleotide (5'-AGTGATA-GAGCCCCAGTTCCAGCGAGACTTCATCTCCTTGC-3' (SEQ. ID. NO. 15)) as probe. Receptor expression studies, $^{125}$I-ET-1-1 and $^{125}$I-AngII binding to membranes were done as described (2).

Genotyping of Mouse Embryos

Genotyping was done by PCR analysis of genomic DNA isolated from extraembryonic membranes. Primers flanking the SacI site localized within the amino acid coding region of Dear (upstream primer: 5'-AACTTCTCTGGTCCGCTCC-3' (SEQ. ID. NO. 11); downstream primer: 5'-ACTTGCT-GAAACTAAAACCTGC-3' (SEQ. ID. NO. 12)) were used to detect the wild type allele (PCR product=153 bp indicative of the presence of the wild type allele) and primers P1 and P2 (described above) to detect the mutated allele (PCR product=5.5 Kb indicative of the presence of the mutated allele).

Analysis of Heterozygous Dear$^{+/-}$ Phenotype

We analyzed backcross BC10[C57BL/6] Dear$^{+/-}$ mice for Dear protein levels by Western blot analysis using equal amounts of protein (40 µg) from mouse kidney membranes and rabbit IgG anti-mouse Dear anti-peptide specific antibody (1:500 dilution) developed against mouse Dear specific synthetic peptide: L$_{16}$SKCNHNEQDTA$_{27}$ (SEQ. ID. NO. 16) to detect Dear-specific polypeptide. We measured blood pressure in 6 month old mice by tail-cuff sphygmomanometer (Visitech BP 2000, Visitech CA) under light anesthesia ascertaining equivalent physiologic state by limiting BP measurements to periods with heart rate ranging from 300-500 beats per minute. We obtained three sets of 10 consecutive readings per mouse and took the average of at least 20 readings within the prescribed normal heart rate range.

Histology

Embryos were collected at embryonic E9.5-E12.5 days from timed-pregnant mice (counting noon of the day a vaginal plug is detected as E0.5); genotypes were determined by PCR analysis of extraembryonic membrane tissue DNA. Embryos were analyzed and photographed within their yolk sacs, then fixed in 4% freshly prepared PBS-buffered paraformaldehyde. Histology processing and Masson-trichrome staining were done following established procedures. Digital stereophotomicroscopy and bright-field photomicroscopy were done using a Nikon stereomicroscope and Zeis Axioskop microscope respectively. Immunohistochemistry was done essentially as described (27).

EXAMPLE 3

Blood Pressure Measurements

Male and female cohorts of Dear KO and wild type (N10 backcross generation) were used to measured BP. Twelve (+/−) and 11 (+/+) female mice and 14 (+/−) and 14 (+/+) male mice were studied. Testing was done at 6 months of age.

Mice were maintained on regular rodent chow and on a 12-hour light/dark cycle. Mice were transported and allowed to settle in the procedure room 1 hour before measurements were taken. Systolic BP along with heart rate was measured by a programmable tail-cuff sphygmomanometer (Visitech BP 2000, Visitech, NC). Mice were lightly anesthetized with intraperitoneal ketamine (80 mg/kg) and xylazine (18 mg/kg) and placed on the heated platform after a 2 minute interval. Three sets of 10 consecutive readings each were taken per mouse. Data is presented as average of at least 20 readings per mouse spanning the heart rate range of 300-500 bpm.

Results

As shown in FIG. 10A, SBP did not differ between WT and KO male mice (WT, 137.2±5.1; KO, 138.6±3.7; t=0.05, P>0.8) at 6 months of age. In contrast, SBP is significantly lower in KO female mice when compared with WT female mice (WT, 134.9±4.0; KO, 112.3±6.1; t=3.03, P<0.01). Mean heart rates did not differ between contrasting groups (FIG. 10B) affirming the SBP differences observed between WT and KO female mice. Thus, heterozygosis at the Dear locus shows gender-specific effects on BP affecting only females. This result is consistent with recent data suggesting a female-specific effect of Dear variants in salt-sensitive hypertension in the Dahl rat model (2).

EXAMPLE 4

Figure 11B:
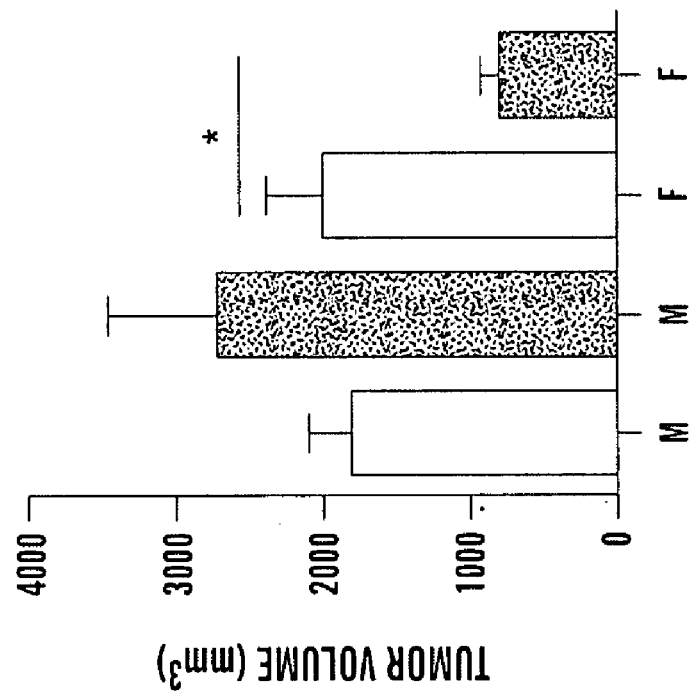
FIGS. 11A-11E: Analysis of Dear-inhibition on tumor growth. In Dear$^{+/-}$ mice (■), decreased tumor mass (mg) (FIG. 11A) and tumor volume (mm$^3$) (FIG. 11B) of melanoma cell-induced subcutaneous tumors were observed in females but not in males compared with age-matched Dear$^{+/+}$ control mice (□).
Figure 11A:
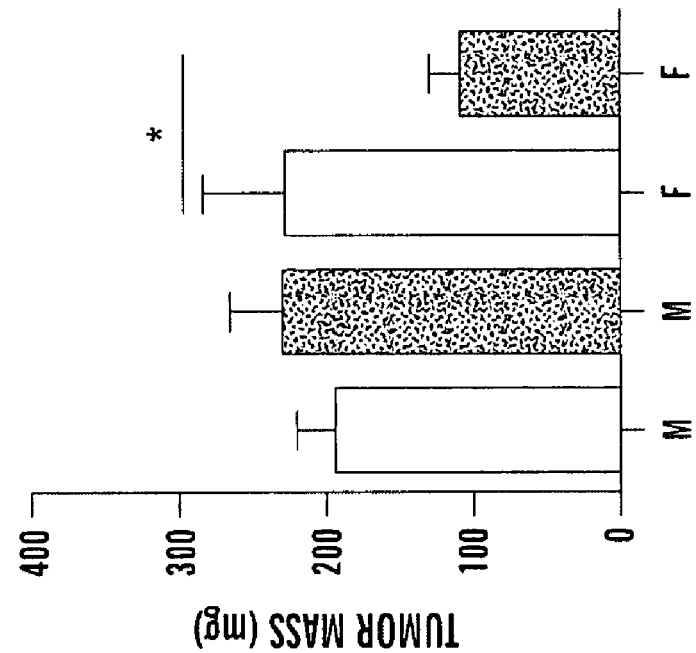
Figure 11D:
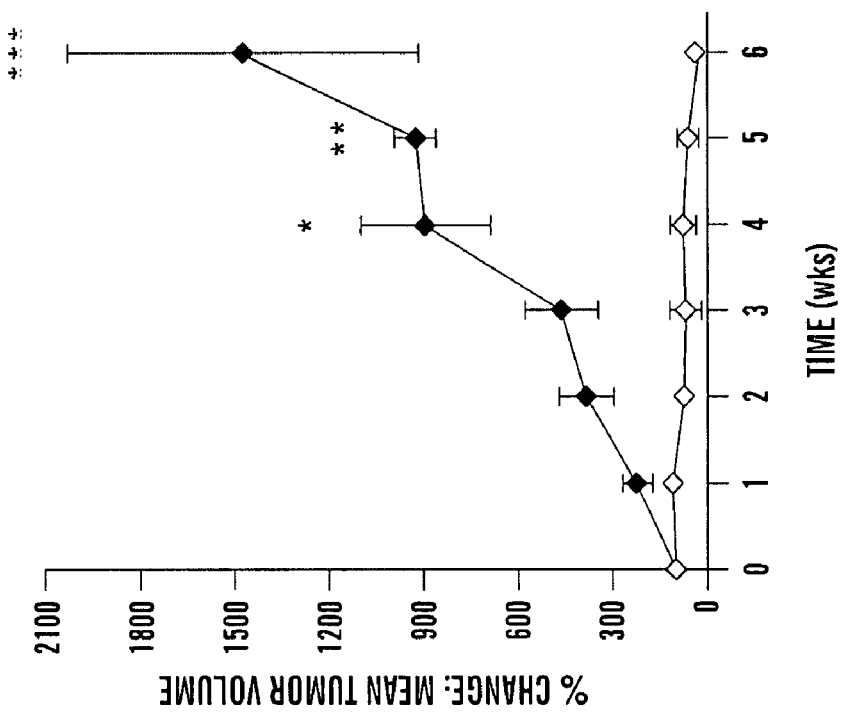
Figure 11C:
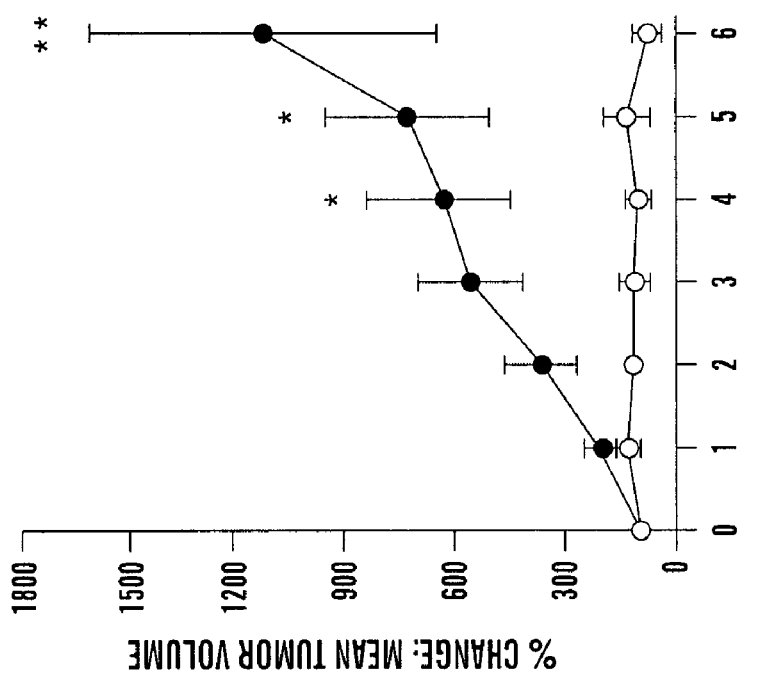
Figure 11E:
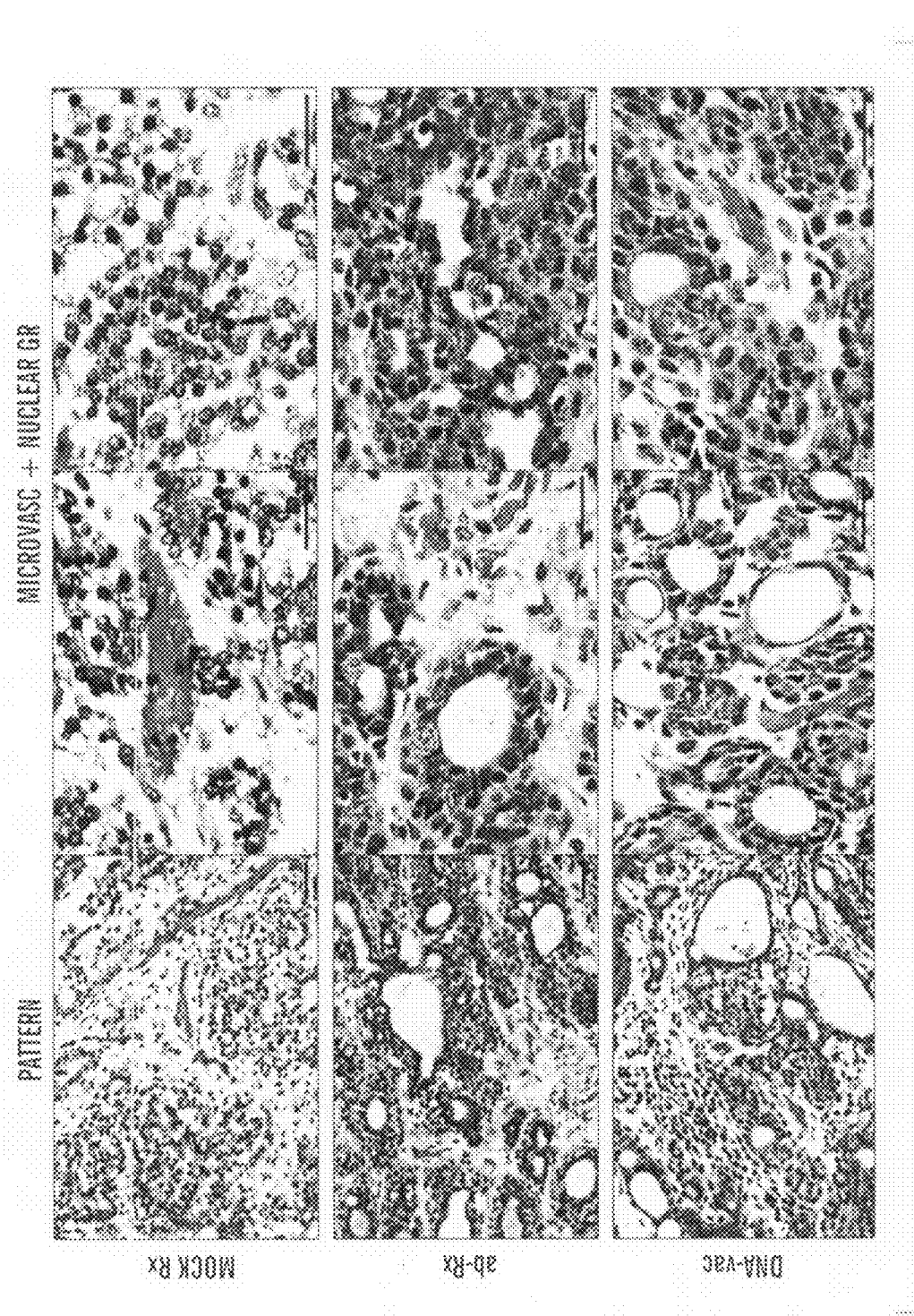

We next investigated the role of Dear-inhibition in two established rodent tumor models. First, comparing heterozygous Dear$^{+/-}$ deficient mice and wild type Dear$^{+/+}$ littermates, we detect significant reduction in tumor mass (FIG. 11A-B) and tumor volume (FIG. 11C-D) in B16-F10 melanoma cell-induced tumor model (74) in heterozygous Dear$^{+/-}$ deficient-female (t-test, P<0.02) mice but not in male mice. Secondly, because effects were seen only in female Dear$^{+/-}$ mice, we next tested whether Dear-inhibition would reduce tumor growth in $^{137}$Cs-radiation induced breast cancer model (70) in female rats with tumor latency less than 3 months. Using two independent inhibition methods, anti-rat Dear anti-peptide specific antibody begun 4 weeks after irradiation (FIG. 11C)

and anti-rat Dear DNA vaccine begun two weeks after irradiation (FIG. 11D), we detect significant reductions in tumor growth during a 6-week observation period. In contrast to respective control groups, both anti-Dear treatments prevented tumor growth with significant reductions in %-change in tumor volume detected from 4-6 weeks after tumor appearance (ab-Rx: P<0.05-0.01; DNA-v: P<0.02-0.001). Furthermore, we detect significant tumor regression with 68% reduction in tumor volume in anti-Dear DNA-vaccinated rats (FIG. 11D, P<0.01). Inhibition of tumor growth is associated with decrease in malignancy-potential based on tumor pattern, nuclear grade and vascular invasion in both anti-Dear antibody and DNA vaccine treated rats compared with age-matched, non-treated control rats (FIG. 11E). Furthermore, decrease in the number of chaotic and mosaic vessels was also detected as a result of anti-Dear treatment.

Methods

Tumor Studies and Dear-Specific Inhibition

We developed B16-F10 (ATCC) melanoma cell-induced subcutaneous tumor model essentially as described (74) in 10-week old Dear$^{+/-}$ and littermate Dear$^{+/+}$ male and female mice (n=5 per group). Thirteen days after tumor induction, we excised tumors and measured tumor weight and volume. We induced rat mammary gland tumors in 48 Sprague Dawley rats (n=12 per group) essentially as described (70) at 40 days of age via $^{127}$Cs-radiation. Only rats with tumor latency less than 3 months were used for study (n=4 for anti-Dear anti-peptide antibody; n=3 for control antibody; n=3 for anti-Dear DNA-vaccine; n=3 for control pCDNA). We began antibody treatments 6 weeks after irradiation at 12 weeks of age. We used affinity-purified rabbit IgG anti-Dear anti-peptide antibody raised against the synthetic peptide P$_{51}$LLTSLGSKE$_{60}$ (1) (SEQ. ID. NO. 7). As control, we used rabbit IgG (sc-2027, Santa Cruz Biologicals, Santa Cruz Calif.). Test and control antibodies were injected thrice weekly intraperitoneally (6 μg/injection) until the end of the study at 6 weeks post tumor appearance. In parallel, we injected test and mock-DNA vaccines—using anti-Dear (pCDNA-Dear) DNA-vaccine and control expression vector (pCDNA, Invitrogen, Carlsbad, Calif.) mock-vaccine—two weeks after irradiation at 8 weeks of age, and thereafter bi-weekly until 6 weeks from tumor appearance (500 μg per dose, intramuscularly). Tumor volume was measured using the formula $(4/3\pi r_1^2 \times r_2)$ where $r_1$ is the smaller, and $r_2$ the larger radius as described (71). We used t-test, two-way repeated measures ANOVA and Tukey's post test for multiple pairwise comparisons for statistical analysis as appropriate.

REFERENCES

1. Ruiz-Opazo, N., Hirayama, K., Akimoto, K. & Herrera, V. L. M. Molecular characterization of a dual endothelin-1/angiotensin II receptor. *Molecular Medicine* 4, 96-108 (1998).
2. Kaneko, Y, Herrera, V. L. M., Didishvili, T. & Ruiz-Opazo, N. Sex-specific effects of dual ET-1/AngII receptor (Dear) variants in Dahl salt-sensitive/resistant hypertension rat model. *Physiol Genomics* 20, 157-164 (2005).
3. Lariviere, R. & Lebel, M. Endothelin-1 in chronic renal failure and hypertension. Can J Physiol Pharmacol. 81, 607-621 (2003).
4. Salani, D. et al. Role of endothelin-1 in neovascularization of ovarian carcinoma. Am. J. Pathol. 157, 1537-1547 (2000).
5. Sullivan, D. C. & Bicknell, R. New molecular pathways in angiogenesis. British Journal of Cancer 89, 228-231 (2003).
6. Bagnato, A. & Spinella, F. Emerging role of endothelin-1 in tumor angiogenesis. Trends in Endocrinology and Metabolism 14, 44-50 (2002).
7. Grant, K., Loizidou, M. & Taylor, I. Endothelin-1: a multifunctional molecule in cancer. British Journal of Cancer 88, 163-166 (2003).
8. Watanabe, T., Barker, T. A. & Berk B. C. Angiotensin II and the Endothelium: Diverse signals and effects. Hypertension 45, 163-169 (2005).
9. Escobar, E., Rodriguez-Reyna, T. S., Arrieta, O. & Sotelo, J. Angiotensin II, cell proliferation and angiogenesis regulator: biologic and therapeutic implications in cancer. Curr Vasc Pharmacol 2, 385-399 (2004).
10. Kurihara, Y. et al. Elevated blood pressure and craniofacial abnormalities in mice deficient in endothelin-1. Nature 368, 703-710 (1994).
11. Clouthier, D. E. et al. Cranial and cardiac neural crest defects in endothelin-A receptor-deficient mice. *Development* 125, 813-824 (1998).
12. Hosoda, K. et al. Targeted and natural (piebald-lethal) mutations of endothelin-B receptor gene produce megacolon associated with spotted coat color in mice. Cell 79, 1267-1276 (1994).
13. Tanimoto, K. et al. Angiotensinogen-deficient mice with hypotension. *J Biol Chem* 269, 31334-31337 (1994).
14. Nimura, F. et al. Gene targeting in mice reveals a requirement for angiotensin in the development and maintenance of kidney morphology and growth factor regulation. J Clin Invest. 96, 2947-2954 (1995).
15. Ito, M. et al. Regulation of blood pressure by the type 1A angiotensin II receptor gene. *Proc Natl Acad Sci* 92, 3521-3525 (1995).
16. Chen, X. et al. Targeting deletion of angiotensin type 1B receptor gene in the mouse. *Am J Physiol* 272, F299-F304 (1997).
17. Hein, L., Barsh, G. S., Pratt, R. E., Dzau, V. J. & Kobilka, B. K. 1996. Behavioral and cardiovascular effects of disrupting the angiotensin II type 2 receptor in mice. *Nature* 377, 744-777 (1996).
18. Carneliet, P. et al. Abnormal blood vessel development and lethality in embryos lacking a single VEGF allele. *Nature* 380, 435-439 (1996).
19. Ferrara, N. et al. Heterozygous embryonic lethality induced by targeted inactivation of the VEGF gene. *Nature* 380, 439-442 (1996).
20. Raab, S. et al. Impaired brain angiogenesis and neuronal apoptosis induced by conditional homozygous inactivation of vascular endothelial growth factor. *Thromb Haemost* 91, 595-605 (2004).
21. Ikeda, T. et al. Pathophysiological roles of endothelin-1 in Dahl salt-sensitive hypertension. Hypertension 34, 514-519 (1999).
22. Touyz, R. M. & Schiffrin, E. L. Role of endothelin in human hypertension. Can J Physiol Pharmacol. 81, 533-541 (2003).
23. Fujita, M. et al. Angiotensin type 1a receptor signaling-dependent induction of vascular endothelial growth factor in stroma is relevant to tumor-associated angiogenesis and tumor growth. *Carcinogenesis* 26, 271-279 (2005).
24. Griswold, D. E. et al. Targeted disruption of the endothelin-B-receptor gene attenuates inflammatory nociception and cutaneous inflammation in mice. *J Cardiovasc Pharmacol* 36, S78-S81 (2000).
25. Dickson, M. C. et al. Defective haematopoiesis and vasculogenesis in transforming growth factor-β1 knockout mice. *Development* 121, 1845-1854 (1995).

26. D'Orleans-Juste, P., Plante, M., Honore, J. C., Carrier, E. & Labonte, J. Synthesis and degradation of endothelin-1. Can J Physiol Pharmacol. 81, 503-510 (2003).

27. Herrera, V. L. M. et al. Spontaneous combined hyperlipidemia, coronary heart disease and decreased survival in Dahl salt-sensitive hypertensive rats transgenic for human cholesteryl ester transfer protein. Nature Med 12, 1383-1389 (1999).

28. Agapitov A V and Haynes W G. Role of endothelin in cardiovascular disease. *J. Renin Angiotensin Aldosterone Syst.* 3: 1-15, 2002.

29. Antoniucci D, Miller V M, Sieck G C, and Fitzpatrick L A. Gender-related differences in proliferative responses of vascular smooth muscle cells to endothelin-1. *Endothelium* 8: 137-145, 2001.

30. Blalock J E. Genetic origins of protein shape and interaction rules. *Nature Medicine* 1: 876-878, 1995.

31. Clark J S, Jeffs B, Davidson A O, Lee W K, Anderson N H, Bihoreau M T, Brosnan M J, Devlin A M, Kelman A W, Lindpaintner K, and Dominiczak A F. Quantitative trait loci in genetically hypertensive rats, possible sex specificity. *Hypertension* 28: 898-906, 1996.

32. Doi T, Hiroaki Y, Arimoto I, Fujiyoshi Y, Okamoto T, Satoh M, and Furuichi Y. Characterization of human endothelin B receptor and mutant receptors expressed in insect cells. *Eur. J. Biochem.* 248: 139-148, 1997.

33. Elijovich F and Laffer C L. Participation of renal and circulating endothelin in salt-sensitive essential hypertension. *J. Hum. Hypertens.* 16: 459-467, 2002.

34. Garrett M R, Dene H, Walder R, Zhang Q Y, Cicila G T, Assadnia S, Deng A Y, and Rapp J P. Genome scan and congenic strains for blood pressure QTL using Dahl Salt sensitive rats. *Genome Res.* 8: 711-723, 1998.

35. Hallberg P, Karlsson J, Lind L, Michaelsson K, Kurland L, Kahan T, Malmqvist K, Ohman K P, Nystrom F, Liljedahl U, Syvanen A C, and Melhus H. Gender-specific association between preproendothelin-1 genotype and reduction of systolic blood pressure during antihypertensive treatment-results from the Swedish Irbersartan Left Ventricular Hypertrophy Investigation versus Atenolol (SILVHIA). *Clin Cardiol.* 27: 287-290, 2004.

36. Hausdorff W P, Hnatowich M, O'Dowd B F, Caron M G, and Lefkowitz R J. A mutation of $b_2$-adrenergic receptor impairs agonist activation of adenylyl cyclase without affecting high affinity agonist binding. Distinct molecular determinants of the receptor are involved in physical coupling to and functional activation of $G_s$. *J. Biol. Chem.* 265: 1388-1393, 1990.

37. Herrera V L M and Ruiz-Opazo N. Genetics of hypertension: A multidisciplinary challenge. *Trends in Cardiovascular Medicine* 1: 185-189, 1991.

38. Herrera V L M, Xiang X H, Lopez L V, Schork N J, and Ruiz-Opazo N. The a1 Na, K-ATPase gene is a susceptibility hypertension gene in the Dahl salt-sensitive rat. *J. Clin. Invest.* 102: 1102-1111, 1998.

39. Herrera V L M, Lopez L V, and Ruiz-Opazo N. α1 Na, K-ATPase and Na, K, 2Cl-cotransporter/D3Mit3 loci interact to increase susceptibility to salt-sensitive hypertension in Dahl S$^{HSD}$ rats. *Molecular Medicine* 7: 125-134, 2001.

40. Iwanaga Y, Kihara Y, Inagaki K, Onozawa Y, Yoneda T, Kataoka K, and Sasayama S. Differential effects of angiotensin II versus endothelin-1 inhibitions in hypertrophic left ventricular myocardium during transition to heart failure. *Circulation* 104: 606-612, 2001.

41. Jeffs B, Negrin C D, Graham D, Clark J S, Anderson N H, Gauguier D, and Dominiczak A F. Applicability of a "speed" congenic strategy to dissect blood pressure quantitative trait loci on rat chromosome 2. *Hypertension* 35: 179-187, 2000.

42. Jorgensen P L. Purification (Na$^+$ plus K$^+$)-ATPase: active site determinations and criteria of purity. *Ann. N.Y. Acad. Sci.* 242: 36-52, 1974.

43. Kaneko Y, Cloix J F, Herrera V L M, and Ruiz-Opazo N. Corroboration of Dahl S Q276L alpha1-Na, K-ATPase protein sequence: impact on affinities for ligands and on E1 conformation. *J Hypertension* 23: 745-752, 2005.

44. Kent R S, De Lean A, and Lefkowitz R J. A quantitative analysis of beta-adrenergic receptor interactions: resolution of high and low affinity states of the receptor by computer modeling of ligand binding data. *Mol. Pharmacol.* 17: 14-23, 1980.

45. Lavalle M, Takamura M, Parent R, and Thorin E. Crosstalk between endothelin and nitric oxide in the control of vascular tone. *Heart Fail. Rev.* 6: 265-276, 2001.

46. Manly K F, Cudmore Jr, R H, and Meer J M. Map Manager QTX, cross-platform software for genetic mapping. *Mammalian Genome* 12: 930-932, 2001.

47. Mukoyama M, Nakajima M, Horiuchi M, Sasamura H, Pratt R E, and Dzau V J. Expression cloning of type 2 angiotensin II receptor reveals a unique class of seven transmembrane receptors. *J. Biol. Chem.* 268: 24539-24542, 1993.

48. Murphy T J, Alexander R W, Griendling K K, Runge M S, and Bernstein K E. Isolation of a cDNA encoding the vascular type-1 angiotensin II receptor. *Nature* 351: 233-236, 1991.

49. Nuedling S, van Eickels M, Allera A, Doevendans P, Meyer R, Vetter H, and Grohe C. 17 Beta-estradiol regulates the expression of endothelin receptor type B in the heart. *Br J Pharmacol.* 140: 195-201, 2003.

50. Phalipou S, Seyer R, Cotte N, Breton C, Barberis C, Hibert M, and Mouillac B. Docking of linear peptide antagonists into the human V1a vasopressin receptor. *J. Biol. Chem.* 274: 23316-23327, 1999.

51. Pravenec M, Gauguier D, Schott J J, Buard J, Kren V, Bila V, Szpirer C, Szpirer J, Wang J M, Huanng H, St. Lezin E, Spence M A, Flodman P, Printz M, Lathrop G M, Vergnaud G, and Kurtz T W. Mapping of quantitative trait loci for blood pressure and cardiac mass in the rat by genome scanning of recombinant inbred strains. *J. Clin. Invest.* 96: 1973-1978, 1995.

52. Rapp J P and Dene H. Development and characteristics of inbred strains of Dahl salt-sensitive and salt-resistant rats. *Hypertension* 7: 340-349, 1985.

53. Rapp J P and Dene H. Failure of alleles at the Na+, K+-ATPase α1 locus to cosegregate with blood pressure in Dahl rats. *J Hypertension* 8: 457-462, 1990.

54. Rapp J P. Genetic analysis of inherited hypertension in the rat. *Physiological Reviews* 80: 135-172, 2000.

55. Rodbard D. Mathematics of hormone-receptor interaction. *Adv. Exp. Medicine* 36: 289-326, 1972.

56. Romero J C and Reckelhoff J F. Role of angiotensin and oxidative stress in essential hypertension. *Hypertension* 34: 943-949, 1999.

57. Ruiz-Opazo N, Akimoto K, and Herrera V L M. Identification of a novel dual AngiotensinII/Vasopressin receptor on the basis of molecular recognition theory. *Nature Medicine* 1:1074-1081, 1995.

58. Ruiz-Opazo N, Lopez L V, and Herrera V L M. The dual AngII/AVP receptor gene N119S/C163R variant exhibits 58. sodium-induced dysfunction and cosegregates with salt-sensitive hypertension in the Dahl salt-sensitive hypertensive rat model. *Molecular Medicine* 8: 24-32, 2002.

59. Samani N J, Gauguier D, Vincent M, Kaiser M A, Bihoreau M T, Lodwick D, Wallis R, Parent V, Kimber P, Rattray F, Thompson J R, Sassard J, and Lathrop M. Analysis of quantitative trait loci for blood pressure on rat chromosomes 2 and 13. Age-related differences in effect. *Hypertension* 28: 1118-1122, 1996.

60. Song Y, Herrera V L M, Filigheddu F, Troffa C, Lopez L V, Glorioso N, and Ruiz-Opazo N. Non-association of the thiazide-sensitive Na, Cl-cotransporter gene with polygenic hypertension in both rats and humans. *J Hypertension* 19: 1547-1551, 2001.

61. Tatchum-Talom R, Martel C, Labrie C, Labrie F, and Marette A. Gender differences in hemodynamic responses to endothelin-1. *J Cardiovasc Pharmacol*. 36: S102-S104, 2000.

62. Tsukamoto T, Shibagaki Y, Imajoh-Ohmi S, Murakoshi T, Suzuki M, Nakamura A, Gotoh H, and Mizumoto K. Isolation and characterization of the yeast mRNA capping enzyme b subunit gene encoding RNA 5'-triphosphatase, which is essential for cell viability. *Biochem. Biophy. Res. Commun*. 239: 116-122, 1997.

63. Wong C, Mahapatra N R, Chitbangonsyn S, Mahboubi P, Mahata M, Mahata S K, and O'Connor D T. The angiotensin II receptor (Agtr1a): functional regulatory polymorphisms in a locus genetically linked to blood pressure variation in the mouse. *Physiol Genomics* 14: 83-93, 2003.

64. Wright J W and Harding J W. Regulatory role of brain angiotensins in the control of physiological and behavioral responses. *Brain Research Reviews* 17: 227-262, 1992.

65. Zicha J, Negrin C D, Dobesova Z, Carr F, Vokurkova M, McBride M W, Kunes J, Dominiczak A F. Altered Na+-K+ pump activity and plasma lipids in salt-hypertensive Dahl rats: relationship to Atp1a1 gene. *Physiol Genomics* 6: 99-104, 2001.

66. Morris R G M, Garrud P, Rawlins J N P, O'Keefe J. Place navigation impaired in rats with hippocampal lesions. *Nature* 297: 681-683 (1982).

67. Richardson J C, Kendal C E, Anderson R, et al. Ultrastructural and behavioural changes precede amyloid deposition in a transgenic model of Alzheimer's disease. *Neuroscience* 122: 213-228 (2003).

68. Galef B G Jr. Socially-induced diet preference can partially reverse a LiCl-induced diet aversion. *Anim Learn Behav* 13: 415-418 (1985).

69. Kaneko Y, Herrera V L, Didishvili T, Ruiz-Opazo, N. Gender-specific effects of dual ET-1/AngII receptor (Dear) variants in Dahl salt-sensitive/resistant hypertension rat model. *Physiol Genomics* November 23; [Epub ahead of print], (2004).

70. Cronkite E P, Shellabarger C J, Bond V P, Lippincott S W. Studies on radiation-induced mammary gland neoplasia in the rat I. The role of the ovary in the neoplastic response of the breast tissue to total- or partial-body X-irradiation. *Radiation Research* 12: 81-93 (1960).

71. Long B J, Jelovac D, Handratta V, Thiantanawat A, MacPherson N, Ragaz J, Goloubeva O G, Brodie A M. Therapeutic strategies using the aromatase inhibitor letrozole and tamoxifen in a breast cancer model. *J Natl Cancer Inst* 96: 456-465 (2004).

72. Storkebaum E, et al. 2004. Treatment of motoneuron degeneration by intracerebroventricular delivery of VEGF in a rat model of ALS. *Nature Neuroscience* 8:85-92.

73. Rissanen et al. 2004. Gene transfer for therapeutic vascular growth in myocardial and peripheral ischemia. *Adv Genet*. 52:117-164.

74. Woodman, S. E. et al. Caveolin-1 knockout mice show an impaired angiogenic response to exogenous stimuli. *Am J Pathol* 162:2059-2068 (2003).

All references described herein are incorporated herein by reference in their entirety.

TABLE 1

Ligand affinities for Dear S44P/M74T and S44/M74 variants.

[$^{125}$I]Tyr$^{4}$-Angiotensin II

| Variant | $B_{max}$ | $K_H$ AngII (nM) | $K_L$ AngII (nM) | h |
|---|---|---|---|---|
| S44P/M74T | no binding | — | — | — |
| S44/M74 | 23.6 ± 0.92 | 0.23 ± 0.08 | 2.65 ± 0.11 | 2.63 ± 0.25 |

[$^{125}$I]Tyr$^{13}$-Endothelin I

| Variant | $B_{max}$ | $K_H$ ET-I (pM) | $K_L$ ET-I (pM) | h |
|---|---|---|---|---|
| S44P/M74T | 20.21 ± 1.59 | 12.0 ± 1.12 | 836 ± 38.1 | 1.45 ± 0.09 |
| S44/M74 | 26.25 ± 1.29 | *4.42 ± 0.89 | *450 ± 12.4 | 1.41 ± 0.12 |

Values are mean ± s.e.m.;
$B_{max}$, maximum ligand binding sites in pmol/mg membrane protein;
$K_H$, dissociation constant for high affinity binding site;
$K_L$, dissociation constant for low affinity binding site;
h, Hill coefficient.
*P < 0.01 (t-test).

TABLE 2

Chromosome-2 analysis of F2 [RxS] male and female cohorts.

| Locus Marker | ($^a$Distance: males/females) | F2[RxS]males LRS | % | P | F2[RxS]females LRS | % | P |
|---|---|---|---|---|---|---|---|
| MAP (mean ± sd) | | 134.3 ± 13.1 | | | 122.6 ± 10.4 | | |
| D2Rat124 | [0.0/0.0] | 1.8 | 2 | 0.40800 | 1.2 | 1 | 0.55024 |
| D2Rat196 | [9.1/7.2] | 0.7 | 1 | 0.71099 | 1.1 | 1 | 0.57694 |
| D2Rat19 | [14.1/13.5] | 0.9 | 1 | 0.62681 | 2.5 | 2 | 0.29225 |
| D2Rat21 | [8.4/6.1] | 1.3 | 1 | 0.52159 | 3.4 | 3 | 0.17980 |
| D2Rat143 | [12.3/14.9] | 1.6 | 1 | 0.45032 | 11.4 | 11 | 0.00332 |
| D2Rat161 | [25.2/10.8] | 0.2 | 0 | 0.91259 | 8.8 | 8 | 0.01247 |
| D2Rat34 | [25.8/12.4] | 4.3 | 4 | 0.11848 | 11.2 | 10 | 0.00376 |
| Dear | [14.8/14.6] | 6.1 | 6 | 0.04816 | 15.2 | 14 | 0.00050 |
| D2Mgh11/ATP1A1 | [2.9/6.1] | 7.7 | 7 | 0.02155 | 9.6 | 9 | 0.00840 |
| D2Rat169 | [7.8/4.5] | 6.2 | 6 | 0.04520 | 5.4 | 5 | 0.06632 |
| D2Rat59 | [10.1/8.8] | 2.7 | 3 | 0.26394 | 1.8 | 2 | 0.41202 |
| SBP (mean ± sd) | | 157.2 ± 14.2 | | | 145.0 ± 11.4 | | |
| D2Rat143 | | 1.3 | 1 | 0.50959 | 11.9 | 11 | 0.00255 |
| Dear | | 7.0 | 6 | 0.03082 | 13.1 | 12 | 0.00145 |
| D2Mgh11/ATP1A1 | | 8.4 | 8 | 0.01491 | 8.3 | 8 | 0.01609 |
| DBP (mean ± sd) | | 113.5 ± 11.8 | | | 102.4 ± 9.7 | | |
| D2Rat143 | | 1.5 | 1 | 0.47431 | 9.8 | 9 | 0.00763 |
| Dear | | 5.2 | 5 | 0.07525 | 14.9 | 14 | 0.00059 |
| D2Mgh11/ATP1A1 | | 7.1 | 6 | 0.02875 | 8.8 | 8 | 0.01204 |

$^a$Genetic distance in cM between markers, males, females; MAP, mean arterial pressure; SBP, systolic blood pressure; DBP, diastolic BP; LRS, likelihood ratio statistic for the association of the trait with loci; %, the amount of the total trait variance which would be explained by a QTL at these loci, as a percent; P, probability value for the association. Statistical values presented were derived from regression analysis based on a free regression model using the MapManager QTXb17 program (19). The localization of Dear and ATP1A1 genes are highlighted.

TABLE 3

Analysis of S-allele effects on blood pressure of Dear locus in F2 [RxS] intercross rats

| | BP (mmHg, mean ± sd) per Genotype | | | ANOVA | Tukey Test P | | | S-allele effect |
|---|---|---|---|---|---|---|---|---|
| | SS | SR | RR | P | SS vs RR | SS vs SR | SR vs RR | |
| FEMALES | | | | | | | | |
| MAP | 130 ± 13.1 | 122 ± 9.1 | 119 ± 8.3 | $6.2 \times 10^{-4}$ | $4.8 \times 10^{-4}$ | 0.01 | n.s. | ↑ |
| SBP | 152 ± 14.2 | 145 ± 10.0 | 141 ± 9.7 | $1.7 \times 10^{-3}$ | $1.0 \times 10^{-3}$ | 0.02 | n.s. | ↑ |
| DBP | 109 ± 12.0 | 102 ± 8.7 | 99 ± 7.6 | $7.3 \times 10^{4}$ | $5.5 \times 10^{4}$ | 0.01 | n.s. | ↑ |
| MALES | | | | | | | | |
| MAP | 139 ± 13.6 | 133 ± 13.4 | 131 ± 10.0 | 0.052 | n.a. | n.a. | n.a. | |
| SBP | 162 ± 14.4 | 156 ± 14.7 | 152 ± 10.9 | 0.034 | 0.04 | n.s. | n.s. | ↑ |
| DBP | 117 ± 12.6 | 113 ± 12.0 | 110 ± 9.2 | 0.085 | n.a. | n.a. | n.a. | |

Legend: MAP, mean arterial blood pressure; SBP, systolic blood pressure; DBP, diastolic blood pressure; ANOVA, analysis of variance; Tukey Test, all pairwise multiple comparison procedure; n.s., not significant; n.a., not applicable.

---

SEQUENCE LISTING

<160> NUMBER OF SEQ ID NOS: 24

<210> SEQ ID NO 1
<211> LENGTH: 3273
<212> TYPE: DNA
<213> ORGANISM: Rattus norvegicus

<400> SEQUENCE: 1

```
tttctaaatg attacttttc tagatacctg tttacaaaac agaagatcct cccttttgaaa      60 ccaaactaaa ctacacttga agaatataaa gtgcacaaag gaagaccacg atgaatcagt     120
accacccatc ttcccagcat tcaagaatgt tcagcgcaca ggaggtgcac agtaagtgtt     180
cctgagagga gtggatacaa cactcaatta tctgggcatg taatgctgat ctgcggtttc     240
ctttacatca gccggcctcc ttcccggttg ggatcaagga agtgaacaga tgcagactca     300
ctctggcagg caccactgag ccagccattt actctcactg catagcaaag ttattttgtc     360
aacttgtttc caggatcctc tgcttccaca gagcagaaac acctcgtcta ggggattctg     420
atccttaccc tcttctttac atttctctct ccagagaagg ttatcctcag ccaaaatcct     480
ccagtatcga cacgtctgag ccgcttgcag caggtctttg ggttccagga atgaaagtac     540
atagagtgcc agctatggaa aaggaaataa gggaggcaca ctcagacaca tcacagaaga     600
aaggttactc tacgaagggt gagcattgag ctgggactgc tggatttcag tgggctgaac     660
gaatcaagag aagcagcatt ttaagagcaa agaaaatgct catcattctc acattaggaa     720
tctgaggctt tactctgggt aacctgtgat tctattggta tttccttaca aagtgagaac     780
aatgccactt atcacaagtt tcttgtgtga gcccagtgct caagctctta gataatccaa     840
ataaatgttg ataaagagac tttatattgt tcataccaat tatcaaaaaa tacaagtaca     900
tttcatgtca gtgtggtaat aatgttttaa ataacacact tccctacagg gttaagtcta     960
tgccattatt cttccacgca gacataaagc acttcccaaa tgaagaacac cccagtagtc    1020
agaaacaaaa accatagctg atatgctaag acagggctct ctccttttgta acttcttttt    1080 tcctcaggaa gtctttgaaa gaacacagaa gccaagagaa tcttttgggg ttttaccttt    1140
tattaatcat ctgtgcttac ttcttaaaat tctaaaacac tttcaaattt gggggactgg    1200
tgatggctca gtcagtaagg tttcatgaag atgagggctc ggatcctggc agtcttggaa    1260
agtcaggcat ggcagttcta gctatagtca ctgctcactg gacagccagc caccgtagct    1320
aaaggcgtaa gctccagact cagtgaaaga cgacatggca aaaacaacat ggatcagctg    1380
```

```
agggatacac ctctggcctc cacgggcaca tacgtgcagg agcatctgaa tgtacttatg    1440
tatacccaca cgaatacata cacatcctac acacatacac actctacagg aggtatcggg    1500
catgtaagat aatccagacg aatattcact tcacgccctg atggcagcaa agggatctcg    1560
tgttactttc ataagtttag tcaaagagtt ctgatgtaga aaaagctcac aagagcaaac    1620
acttttcttc tgggacactg tcacctttaa aaagtactca aaaggggga aagtgccagg     1680 aaaaagatga tttatcaatt tgcttttcccc cagaattata ttttaattca tcaattttac   1740
tcaaatctaa tgccagattc taactaggac tatatttaat gccactagga ctttagagtg    1800
atcatctaag aaaggagaaa gcaagactct tcctgttcaa atgaggtttc gggatcatct    1860
gtatgaagga tgtggtagtt ttttgatgct gtctttttaa ctgctattta aacatgtgt     1920 atagtaattt gagaaaatat ggactatggg gcattatcta atatcacatt atttcttcct    1980
tttgataaaa attaagctat gaagtctaat gtcaatatgt gcattatatt taaaccatca    2040
gccacacatg gctgtatgac taagtgccta agaatccaat ttttttgtgg tatctctctc    2100
tctccctctc tccgtatgtg tgtgtctttc tctgtctctg tctctctctc tctttctctc    2160
tgacgaagga tgataagtag aaatgccata aaaacatata gataaatttt atatattggg    2220
ggctggagag atggctcagt ggttgagaac actgactgtt cttcagaggt cctgagttaa    2280
attcccagca accacatggt agctcacaac catctatatt gcatctgatg ccctcttctg    2340
gtgtgtctaa agacagctac cggtatactt acatataata aataaatctt taaaaaaatt    2400
ttttatatat taaaaaaaaa tcacataatg taataaccag gagaaatacg aacaatcgat    2460
aaaattactg gtcttgaagg ggcattaaat aattagcaaa ataaaaacaa aattaatatt    2520
gttgcttagt gaatccagaa ttttgaaaac atccactata tataataaac ataccaacta    2580
actaaagtca gcctttagat aacccaggga aaactgaaga gactcggcga cttcacatga    2640
agccttactt tatccaagcg gaagaaagca gcaccttggt atgagcacac tttatgtaac    2700
agctgtacca aaaagccaca gcagtttgcc aaagtgtcaa gccatgatga gcaggacact    2760
gcttacaggc atggctatgt atctggacag cagccatgcg ggtgctgcat ccatgcaggt    2820
gagctggccg cccttactca cctctttggg gagcaaggag atgaagtctc gctggaactg    2880
gggctcgatc acttgcatca tgtgcttcac ttgtgtgggt tcacagctat cgatgagctc    2940
atctaaggcc agcaacttct ctggtccact ccagctctac caaagaggaa ttggacacat    3000
tacaaatcca tacagaagac caccagcacc tgcatggcca tgttcgagca gtggaactac    3060
atgaaggggg accgtggaca gagaccttgt ctccagaagc caccagagcg atagcagttt    3120
ttagtttcag caagtttact cagtaccttt cccgcaaagc attaaaagtc atgactggca    3180
gaaaaataag tctgcattta tttttaatta taagacttat gctaacacca agacactggg    3240
agacacacaa tatccatctg ggttattgac tag                                 3273
```

<210> SEQ ID NO 2
<211> LENGTH: 127
<212> TYPE: PRT
<213> ORGANISM: Rattus norvegicus

<400> SEQUENCE: 2

Met Ser Thr Leu Tyr Val Thr Ala Val Pro Lys Ser His Ser Ser Leu
 1               5                  10                  15

Pro Lys Cys Gln Ala Met Met Ser Arg Thr Leu Leu Thr Gly Met Ala
             20                  25                  30

Met Tyr Leu Asp Ser Ser His Ala Gly Ala Ala Ser Met Gln Val Ser

```
                35              40                  45
Trp Pro Pro Leu Leu Thr Ser Leu Gly Ser Lys Glu Met Lys Ser Arg
        50                  55                  60

Trp Asn Trp Gly Ser Ile Thr Cys Ile Met Cys Phe Thr Cys Val Gly
65                  70                  75                  80

Ser Gln Leu Ser Met Ser Ser Ser Lys Ala Ser Asn Phe Ser Gly Pro
                85                  90                  95

Leu Gln Leu Tyr Gln Arg Gly Ile Gly His Ile Thr Asn Pro Tyr Arg
            100                 105                 110

Arg Pro Pro Ala Pro Ala Trp Pro Cys Ser Ser Ser Gly Thr Thr
            115                 120                 125
```

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aagaaagcag caccttggt                                              19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgtggacaga gaccttgtct                                             20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gctatgtatc tggacagcag c                                           21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agtgaagcac atgatgcaag t                                           21

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Pro Leu Leu Thr Ser Leu Gly Ser Lys Glu
 1               5                   10
```

<210> SEQ ID NO 8
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
agtgatagag ccccagttcc agcgagactt catctccttg c                        41

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgtgaggcta gaaggctgc                                                 19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gagcaaggtg agatgacagg                                                20

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aacttctctg gtccgctcc                                                 19

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
acttgctgaa actaaaacct gc                                             22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cacacaaagc cttactttat cc                                             22

```
<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aaagccagcc tttagataac c                                              21

<210> SEQ ID NO 15
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
agtgatagag ccccagttcc agcgagactt catctccttg c                        41

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Ser Lys Cys Asn His Asn Glu Gln Asp Thr Ala
 1               5                  10

<210> SEQ ID NO 17
<211> LENGTH: 15
<212> TYPE: DNA
<213> ORGANISM: Rattus norvegicus
<220> FEATURE:
<221> NAME/KEY: CDS
<222> LOCATION: (1)..(15)

<400> SEQUENCE: 17 gct gca tcc atg cag                                                  15
Ala Ala Ser Met Gln
 1               5

<210> SEQ ID NO 18
<211> LENGTH: 5
<212> TYPE: PRT
<213> ORGANISM: Rattus norvegicus

<400> SEQUENCE: 18

Ala Ala Ser Met Gln
 1               5

<210> SEQ ID NO 19
<211> LENGTH: 15
<212> TYPE: DNA
<213> ORGANISM: Rattus norvegicus
<220> FEATURE:
<221> NAME/KEY: CDS
<222> LOCATION: (1)..(15)

<400> SEQUENCE: 19 tgc atc atg tgc ttc                                                  15
Cys Ile Met Cys Phe
```

<210> SEQ ID NO 20
<211> LENGTH: 5
<212> TYPE: PRT
<213> ORGANISM: Rattus norvegicus

<400> SEQUENCE: 20

Cys Ile Met Cys Phe
1               5

<210> SEQ ID NO 21
<211> LENGTH: 15
<212> TYPE: DNA
<213> ORGANISM: Rattus norvegicus

<400> SEQUENCE: 21
gctgcaccca tccag                                            15

<210> SEQ ID NO 22
<211> LENGTH: 15
<212> TYPE: DNA
<213> ORGANISM: Rattus norvegicus

<400> SEQUENCE: 22
tgcatcagct gcttc                                            15

<210> SEQ ID NO 23
<211> LENGTH: 127
<212> TYPE: PRT
<213> ORGANISM: Rattus norvegicus

<400> SEQUENCE: 23

Met Ser Thr Leu Tyr Val Thr Ala Val Pro Lys Ser His Ser Ser Leu
1               5                   10                  15

Pro Lys Cys Gln Ala Met Met Ser Arg Thr Leu Leu Thr Gly Met Ala
            20                  25                  30

Met Tyr Leu Asp Ser Ser His Ala Gly Ala Ala Pro Met Gln Val Ser
        35                  40                  45

Trp Pro Pro Leu Leu Thr Ser Leu Gly Ser Lys Glu Met Lys Ser Arg
    50                  55                  60

Trp Asn Trp Gly Ser Ile Thr Cys Ile Thr Cys Phe Thr Cys Val Gly
65                  70                  75                  80

Ser Gln Leu Ser Met Ser Ser Ser Lys Ala Ser Asn Phe Ser Gly Pro
                85                  90                  95

Leu Gln Leu Tyr Gln Arg Gly Ile Gly His Ile Thr Asn Pro Tyr Arg
            100                 105                 110

Arg Pro Pro Ala Pro Ala Trp Pro Cys Ser Ser Ser Gly Thr Thr
        115                 120                 125

<210> SEQ ID NO 24
<211> LENGTH: 127
<212> TYPE: PRT
<213> ORGANISM: Mus musculus

<400> SEQUENCE: 24

Met Asn Ala Leu Tyr Val Thr Thr Val Pro Lys Gly Tyr Ser Ser Leu
1               5                   10                  15

Ser Lys Cys Asn His Asn Glu Gln Asp Thr Ala Tyr Arg Leu Trp Leu
            20                  25                  30

Cys Thr His Asn His Trp Thr Ala Pro Ser Gly Met Arg Leu Gln Pro

```
                    35                      40                      45
Leu Thr Ser Leu Gly Ser Lys Glu Met Lys Ser Arg Trp Asn Trp Gly
        50                      55                      60

Ser Ile Thr Cys Ile Ile Cys Phe Thr Cys Val Gly Ser Gln Leu Ser
 65             70                       75                      80

Met Ser Ser Ser Lys Ala Ser Asn Phe Ser Gly Pro Leu Gln Leu Tyr
                85                      90                      95

Gln Arg Gly Ile Gly His Ile Thr Asn Ser Tyr Lys Arg Pro Gln Ala
            100                     105                 110

Pro Ala Trp Pro Cys Leu Ser Ser Gly Thr Met Gly Arg Ser His
        115                     120                 125
```

We claim:

1. A method for inhibiting angiogenesis in an individual comprising administering to said patient an antibody or antibody fragment that can block binding to the Dual Endothelin-1/Angiotensin II Receptor (Dear) ET-1 domain.

2. The method of claim 1, wherein the antibody or antibody fragment is a humanized antibody or antibody fragment.

3. The method of claim 1, wherein the angiogenesis is associated with a disease or disorder selected from the group consisting of, immune and non-immune inflammation, chronic articular rheumatism, psoriasis, diabetic retinopathy, neovascular glaucoma, restenosis, macular degeneration, capillary proliferation in atherosclerotic plaques, osteoporosis, cancer, solid tumors, solid tumor metastases, angiofibromas, retrolental fibroplasia, hemangiomas, and Kaposi sarcoma.

4. The method of claim 1, wherein the antibody or antibody fragments blocks binding to the ET-1 domain of SEQ ID NO: 2.

5. The method of claim 1, wherein the ET-1 domain comprises amino acids 60-67 of SEQ ID NO: 2.

* * * * *